(12) United States Patent
Sugiyama et al.

(10) Patent No.: US 7,662,596 B2
(45) Date of Patent: Feb. 16, 2010

(54) ALDOLASE, AND METHOD FOR PRODUCING OPTICALLY ACTIVE IHOG AND MONATIN

(75) Inventors: Masakazu Sugiyama, Kawasaki (JP); Kunihiko Watanabe, Kawasaki (JP); Kenichi Mori, Kawasaki (JP); Hiroyuki Nozaki, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 223 days.

(21) Appl. No.: 11/953,372

(22) Filed: Dec. 10, 2007

(65) Prior Publication Data

US 2009/0258403 A1 Oct. 15, 2009

Related U.S. Application Data

(60) Continuation of application No. 11/362,915, filed on Feb. 28, 2006, now Pat. No. 7,371,549, which is a division of application No. 11/146,093, filed on Jun. 7, 2005, now Pat. No. 7,241,599.

(30) Foreign Application Priority Data

Jun. 7, 2004 (JP) ............................. 2004-169188
Dec. 27, 2004 (JP) ............................. 2004-375769

(51) Int. Cl.
*C12P 13/04* (2006.01)
*C12P 17/10* (2006.01)
*C12N 9/10* (2006.01)
*C12N 1/21* (2006.01)

(52) U.S. Cl. .................... 435/106; 435/121; 435/252.3; 435/189; 435/193

(58) Field of Classification Search ........................ None
See application file for complete search history.

(56) References Cited

U.S. PATENT DOCUMENTS

2005/0004394 A1 1/2005 Kawahara et al.
2005/0009153 A1 1/2005 Sugiyama et al.
2005/0153405 A1 7/2005 Sugiyama et al.
2005/0244939 A1 11/2005 Sugiyama et al.
2006/0003426 A1 1/2006 Sugiyama et al.

FOREIGN PATENT DOCUMENTS

| JP | 64-25757 | 1/1989 |
|---|---|---|
| WO | WO 03/056026 A1 | 7/2003 |
| WO | WO 03/059865 A1 | 7/2003 |
| WO | WO 03/091396 A2 | 11/2003 |
| WO | WO 2004/018672 A1 | 3/2004 |

OTHER PUBLICATIONS

J.M. Stringfellow, et al., "Sequence of the *Escherichia coli* C Homoprotocatechuic Acid Degradative Operon Completed With That of the 2,4-Dihydroxyhept-2-ene-1,7-Dioic Acid Aldolase-Encoding Gene (HPCH)", Gene, 166, 1995, pp. 73-76.
Database UniProt Online, "Putative Aldolase", Database Accession No. Q7WNI8, Oct. 1, 2003, XP-002352627.
Database CA Online, "Mutagenesis and Crystal Structure of Pseudomonas Taetrolens Aldolase and the use of the Enzyme for Production of Optically Activity IHOG", Database Accession No. 2005:1044726, Sep. 29, 2005, XP-002352628.
Whisstock, et al., Quarterly Rev. Biophy. 2003, 36, pp. 307-340.
Kaneko T., et al., "Complete genomic sequence of nitrogen-fixing symbiotic bacterium *Bradyrhizobium japonicum* USDA 110; putative aldolase [*Bradyrhizobium japonicum* USDA 110]", DNA Res. 9 (6), NCBI Reference Sequence: NP_772343.1, 2002, 2 pages.

*Primary Examiner*—Delia M Ramirez
*Assistant Examiner*—MD. Younus Meah
(74) *Attorney, Agent, or Firm*—Oblon, Spivak, McClelland, Maier & Neustadt, L.L.P.

(57) ABSTRACT

The present invention relates to a method for producing optically active IHOG, which can in turn be used for the production of monatin. The present invention further relates to a method for producing optically active monatin, and aldolase used for these methods. As such, the present invention enables the synthesis of 4-(Indole-3-ylmethyl)-4-hydroxy-2-oxoglutaric acid with high optical purity, which is useful as an intermediate in the synthesis of optically active monatin, from indole pyruvic acid and pyruvic acid (or oxaloacetic acid).

32 Claims, 7 Drawing Sheets

FIG.1

| | | | |
|---|---|---|---|
| ALD_AA.txt | 1 | MXXXRLNXXIRAXEXGKXAXXXXFXKXDKXTAXEXXDXPYDGXVFEMEHNPYDVXXLGDAL | 60 |
| SpALD_AA.txt | 1 | ..TQT....GI...L.A..P.FTC.S.V...L.Q.LT.A........AA..... | 60 |
| BuALD_AA.txt | 1 | .SNI....SI..F.S..A.HAA.A..L..I..MS.S........SA..... | 60 |
| SpALD2_AA.txt | 1 | .TDN....GV..W.Q..P.FAA.S.V...L.Q.MT.A........GG..... | 60 |

| | | | |
|---|---|---|---|
| ALD_AA.txt | 61 | QYMLXRKXIXEXXSVAXXXVTPXARIPANGXEMNQXXAKQVLDRGXYGVIXPHVXTVEQAX | 120 |
| SpALD_AA.txt | 61 | ....N...K.A..SG...PS...........G........FQ......V..T..S...Y | 120 |
| BuALD_AA.txt | 61 | ....S..Q.V..TA...TK..........I..........SF......A..W..A...Y | 120 |
| SpALD2_AA.txt | 61 | ....N..K.A..SG...PS..L.........A........FQ......V..T..S...W | 120 |

| | | | |
|---|---|---|---|
| ALD_AA.txt | 121 | NXVASXRYAXPXXAXLYEPKGXRGDGPAXAARYWGLSXXXXYYXXADVWPLAPXGEXLVGX | 180 |
| SpALD_AA.txt | 121 | M......A..K.TG.A................T.............QPE...AK....H.L.. | 180 |
| BuALD_AA.txt | 121 | .A....C..R.KS..P..........V......N.............MQE...DK....Q..I.. | 180 |
| SpALD2_AA.txt | 121 | .A....C..K.KG.A................T.............QPD...AR....H..L.. | 180 |

| | | | |
|---|---|---|---|
| ALD_AA.txt | 181 | MCESXXXAIXNLDDILXXXVPGIGXXXLIGEGDLSQXLGXPRQYXHPEVXXAMXXIVEXCXKH | 240 |
| SpALD_AA.txt | 181 | ......PE...E......AN....LV........A.Y........D...VS..NR..V.K.. | 240 |
| BuALD_AA.txt | 181 | ......TQ...E......AN....FI........E.F........E...VD..RQ..T.K.. | 240 |
| SpALD2_AA.txt | 181 | ......PE...D......SD....LV........A.Y........E...LD..RR..T.H.. | 240 |

| | | | |
|---|---|---|---|
| ALD_AA.txt | 241 | XIVXIVGXPHXXXAKNXXRLXXEGYXXLMSAPXRXIYGVVGXXXRXXAGY | 285 |
| SpALD_AA.txt | 241 | N.V...TN..VE..IG...RF....T.S......QG.EL | 285 |
| BuALD_AA.txt | 241 | D.V..H..VT..HR..ME...RY....Q.T......LA.DM | 285 |
| SpALD2_AA.txt | 241 | K.A..N..TN..VE..LG...KF....S.S......QG.EL | 285 |

ALD_AA : CORE SEQUENCE ( SEQ ID NO:2 3 )
SpALD_AA : SEQ ID NO:2
BuALD_AA : SEQ ID NO:1 5
SpALD2_AA : SEQ ID NO:1 3

SEQUENCE LISTING

<160> NUMBER OF SEQ ID NOS: 23

<210> SEQ ID NO 1
<211> LENGTH: 1449
<212> TYPE: DNA
<213> ORGANISM: Sphingomonas sp.
<220> FEATURE:
<221> NAME/KEY: CDS
<222> LOCATION: (210)..(1004)

<400> SEQUENCE: 1

```
ggatcccgc cttcgcgggg atgacggact gatttgttga gccgtgggtg atatttctcg      60
cggtcggacg ggagagtgag ggatcactcc cgggcaggtt ccaaaacgga cctgccggtt    120
tttcgatggc ggcggtcgcc ggatcaatcg cgcgatgccg cccgggacga ggtacgggca    180
gagcaagccc gaaaggaaag atccaagca atg acc cag acg cgc ctc aac ggc      233
                                  Met Thr Gln Thr Arg Leu Asn Gly
                                  1               5 atc atc cgc gct ctc gaa gcc ggc aag ccc gct ttc acc tgc ttc tcg      281
Ile Ile Arg Ala Leu Glu Ala Gly Lys Pro Ala Phe Thr Cys Phe Ser
    10              15                  20 aag gtc gac aag ctg acc gcg cag gaa ctg acc gat gcc ccc tat gac      329
Lys Val Asp Lys Leu Thr Ala Gln Glu Leu Thr Asp Ala Pro Tyr Asp
25              30                  35                  40 ggc gtg gtc ttc gag atg gag cac aac ccc tac gat gtc gcg gcg ctg      377
Gly Val Val Phe Glu Met Glu His Asn Pro Tyr Asp Val Ala Ala Leu
                45                  50                  55 ggt gat gct ctc cag tac atg ctc aac cgc aag aag atc gcc gaa agc      425
Gly Asp Ala Leu Gln Tyr Met Leu Asn Arg Lys Lys Ile Ala Glu Ser
            60                  65                  70 ggt tcg gtc gcg ccc tcg gtc acc ccc atc gcg cga atc ccg gcc aat      473
Gly Ser Val Ala Pro Ser Val Thr Pro Ile Ala Arg Ile Pro Ala Asn
        75                  80                  85 ggc ggt gag atg aac cag ttc caa gcc aag cag gtg ctg gat cgc ggc      521
Gly Gly Glu Met Asn Gln Phe Gln Ala Lys Gln Val Leu Asp Arg Gly
    90                  95                  100 gtc tac ggc gtg atc acg ccg cac gtt tcg acc gtg gag cag gcc tac      569
Val Tyr Gly Val Ile Thr Pro His Val Ser Thr Val Glu Gln Ala Tyr
105                 110                 115                 120 aac atg gtc gct tcc gcc cgc tat gcg aag ccg acc ggc gcc gcg ctc      617
Asn Met Val Ala Ser Ala Arg Tyr Ala Lys Pro Thr Gly Ala Ala Leu
                125                 130                 135 tac gaa ccc aag ggc att cgc ggc gac ggc ccg gcc acg gcc gcg cgc      665
Tyr Glu Pro Lys Gly Ile Arg Gly Asp Gly Pro Ala Thr Ala Ala Arg
```

```
                     140                 145                 150
tat tgg ggc ctg tcg cag ccg gaa tac tac gcc aag gcc gac gtc tgg      713
Tyr Trp Gly Leu Ser Gln Pro Glu Tyr Tyr Ala Lys Ala Asp Val Trp
        155                 160                 165 ccg ctg gcg ccg cat ggc gaa cta ctg gtg ggc atg atg tgc gag agt      761
Pro Leu Ala Pro His Gly Glu Leu Leu Val Gly Met Met Cys Glu Ser
    170                 175                 180 ccc gag gcg atc gag aac ctc gac gac att ctc gcc aat gtc ccc ggc      809
Pro Glu Ala Ile Glu Asn Leu Asp Asp Ile Leu Ala Asn Val Pro Gly
185                 190                 195                 200 atc ggc ctc gtg ctg atc ggt gag ggc gat ctc agc cag gcg ctg ggc      857
Ile Gly Leu Val Leu Ile Gly Glu Gly Asp Leu Ser Gln Ala Leu Gly
                205                 210                 215 tac ccg cgc cag tac gac cac ccg gaa gtg gtc agc gcg atg aac agg      905
Tyr Pro Arg Gln Tyr Asp His Pro Glu Val Val Ser Ala Met Asn Arg
            220                 225                 230 atc gtc gag gtc tgc aag aag cac aac gtc gtc gtc ggc aac ccg cac      953
Ile Val Glu Val Cys Lys Lys His Asn Val Val Val Gly Asn Pro His
        235                 240                 245 acc aac gcc aag aac gtc gag cgc ctg atc ggc gag ggc tac cgc ttc     1001
Thr Asn Ala Lys Asn Val Glu Arg Leu Ile Gly Glu Gly Tyr Arg Phe
    250                 255                 260 ctg atgtccgcgc gacgcgcag ctacggcgtg gtcggtcagg gccgcgaact            1054
Leu
265 ggcgggtac tgaccatggc caatggtgca gaaaccctcg tcaacacgct ggtcgacaac     1114
ggtgtggagg tttgcttcgc gaaccccggc acttcggaaa tgcacttcct ggcggcgctc    1174
gacaatccgc gcatgaagtc ggtgctgtgc ctttacgaag cgtctgcac cggcgcggcg     1234 gatggctggt accggatgaa ggacgtgccg gcatcgaccc tgctgcatct ggggccgggt    1294
ctcgccaacg gcctgtccaa catccacaac gccaagcgcg cctcgtccgg catggtcaac    1354
atcgtcggcg agcactcggc atcgcacctg aagtacgatc cgccgctgac ctccgacatc    1414 gagggggctgg ccgcccgctc agccactggg tgcgc                              1449
```

<210> SEQ ID NO 2
<211> LENGTH: 265
<212> TYPE: PRT
<213> ORGANISM: Sphingomonas sp.

<400> SEQUENCE: 2

```
Met Thr Gln Thr Arg Leu Asn Gly Ile Ile Arg Ala Leu Glu Ala Gly
1               5                   10                  15

Lys Pro Ala Phe Thr Cys Phe Ser Lys Val Asp Lys Leu Thr Ala Gln
            20                  25                  30

Glu Leu Thr Asp Ala Pro Tyr Asp Gly Val Val Phe Glu Met Glu His
        35                  40                  45

Asn Pro Tyr Asp Val Ala Ala Leu Gly Asp Ala Leu Gln Tyr Met Leu
    50                  55                  60

Asn Arg Lys Lys Ile Ala Glu Ser Gly Ser Val Ala Pro Ser Val Thr
65                  70                  75                  80

Pro Ile Ala Arg Ile Pro Ala Asn Gly Gly Glu Met Asn Gln Phe Gln
                85                  90                  95

Ala Lys Gln Val Leu Asp Arg Gly Val Tyr Gly Val Ile Thr Pro His
            100                 105                 110

Val Ser Thr Val Glu Gln Ala Tyr Asn Met Val Ala Ser Ala Arg Tyr
        115                 120                 125
```

```
Ala Lys Pro Thr Gly Ala Ala Leu Tyr Glu Pro Lys Gly Ile Arg Gly
    130                 135                 140

Asp Gly Pro Ala Thr Ala Arg Tyr Trp Gly Leu Ser Gln Pro Glu
145                 150                 155                 160

Tyr Tyr Ala Lys Ala Asp Val Trp Pro Leu Ala Pro His Gly Glu Leu
                165                 170                 175

Leu Val Gly Met Met Cys Glu Ser Pro Glu Ala Ile Glu Asn Leu Asp
            180                 185                 190

Asp Ile Leu Ala Asn Val Pro Gly Ile Gly Leu Val Leu Ile Gly Glu
        195                 200                 205

Gly Asp Leu Ser Gln Ala Leu Gly Tyr Pro Arg Gln Tyr Asp His Pro
    210                 215                 220

Glu Val Val Ser Ala Met Asn Arg Ile Val Glu Val Cys Lys Lys His
225                 230                 235                 240

Asn Val Val Gly Asn Pro His Thr Asn Ala Lys Asn Val Glu Arg
                245                 250                 255

Leu Ile Gly Glu Gly Tyr Arg Phe Leu
            260                 265

<210> SEQ ID NO 3
<211> LENGTH: 17
<212> TYPE: PRT
<213> ORGANISM: Sphingomonas sp.

<400> SEQUENCE: 3

Gly Val Tyr Gly Val Ile Thr Pro His Val Ser Thr Val Glu Gln Ala
1               5                   10                  15

Tyr

<210> SEQ ID NO 4
<211> LENGTH: 12
<212> TYPE: PRT
<213> ORGANISM: Sphingomonas sp.

<400> SEQUENCE: 4

Tyr Trp Gly Leu Ser Gln Pro Glu Tyr Tyr Ala Lys
1               5                   10

<210> SEQ ID NO 5
<211> LENGTH: 32
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (1)..(32)
<223> OTHER INFORMATION: y represents c or t/u; n represents a, c, g,
      t/u; w represents a, t/u; s represents c, g; b represents c, g,
      t/u; and r represents a, g.

<400> SEQUENCE: 5
atycanccnc aygtnwsbca ngtngarcar gc                                     32

<210> SEQ ID NO 6
<211> LENGTH: 28
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
```

```
<222> LOCATION: (1)..(28)
<223> OTHER INFORMATION: r represents a, g; y represents c or t/u; v
      represents a, c, g; s represents c, g; w represents a, t/u; and n
      represents a, c, g, t/u.

<400> SEQUENCE: 6
gcrtartayt cnggytgvsw varncccc                                      28

<210> SEQ ID NO 7
<211> LENGTH: 40
<212> TYPE: DNA
<213> ORGANISM: Artificial Sequence
<220> FEATURE:
<223> OTHER INFORMATION: Synthetic DNA

<400> SEQUENCE: 7
gtatcacgag gccctagctg tggtgtcatg gtcggtgatc                         40

<210> SEQ ID NO 8
<211> LENGTH: 40
<212> TYPE: DNA
<213> ORGANISM: Artificial Sequence
<220> FEATURE:
<223> OTHER INFORMATION: Synthetic DNA

<400> SEQUENCE: 8
ttcggggatt ccatatgata ccctttttac gtgaacttgc                         40

<210> SEQ ID NO 9
<211> LENGTH: 38
<212> TYPE: DNA
<213> ORGANISM: Artificial Sequence
<220> FEATURE:
<223> OTHER INFORMATION: Synthetic DNA

<400> SEQUENCE: 9
ggggggggca tatgcgacct ccttattacg tgaacttg                           38

<210> SEQ ID NO 10
<211> LENGTH: 37
<212> TYPE: DNA
<213> ORGANISM: Artificial Sequence
<220> FEATURE:
<223> OTHER INFORMATION: Synthetic DNA

<400> SEQUENCE: 10
ggccatatga cccagacgcg cctcaacggc atcatcc                            37

<210> SEQ ID NO 11
<211> LENGTH: 39
<212> TYPE: DNA
<213> ORGANISM: Artificial Sequence
<220> FEATURE:
<223> OTHER INFORMATION: Synthetic DNA

<400> SEQUENCE: 11
gcgctgcagt cagtaccccg ccagttcgcg gccctgacc                          39

<210> SEQ ID NO 12
<211> LENGTH: 2470
<212> TYPE: DNA
<213> ORGANISM: Sphingomonas sp.
<220> FEATURE:
<221> NAME/KEY: CDS
<222> LOCATION: (399)..(1253)

<400> SEQUENCE: 12
```

```
cggcaaggcg ctggtcgatg cggtgaaggc gtggaagagc gatgcccgcg tcgccatcat    60
cgcctcgggc gggctcaccc atttcgtctg cgacccggac ctcgacaagg tcttcatcga   120
tgcgctgggc agctatgatt tcgacacgct ggagggatc gacaaccgct cctaccagtc    180
gggcacgtcg gaggtgaagc tctattgctc ggtgctggtc gcgatgcagg aatccaacac   240
ccagatgacc ttggtcgact atgtcccctg cctgcgcacg gcggcgggca ccggcgaggg   300
catgggcttc atgtattgga gcccggcggc cgcctgatcc tgcaccctg atacaagatc    360 ccccggccgc atcgccgggc atgaaggaat gatctgag atg acc gac aat cgc ctc   416
                                          Met Thr Asp Asn Arg Leu
                                           1               5
```

```
aac ggc gtg atc cgc gcc tgg gaa cag ggc aag ccc gcc ttc gcc gcc    464
Asn Gly Val Ile Arg Ala Trp Glu Gln Gly Lys Pro Ala Phe Ala Ala
         10                  15                  20 ttt tcc aag gtc gac aag ctg acc gcc cag gaa atg acc gac gcc ccc    512
Phe Ser Lys Val Asp Lys Leu Thr Ala Gln Glu Met Thr Asp Ala Pro
     25                  30                  35 tat gac ggc atc gtc ttc gag atg gag cat aac ccc tat gat gtc ggg    560
Tyr Asp Gly Ile Val Phe Glu Met Glu His Asn Pro Tyr Asp Val Gly
 40                  45                  50 ggc ctg ggc gac gcg ctc cag tac atg ctc aac cgc aag aag atc gcc    608
Gly Leu Gly Asp Ala Leu Gln Tyr Met Leu Asn Arg Lys Lys Ile Ala
55                  60                  65                  70 gaa agc gga tcg gtc gcg ccc tcg gtc acg ccg ctg gcg cgc atc cct    656
Glu Ser Gly Ser Val Ala Pro Ser Val Thr Pro Leu Ala Arg Ile Pro
                 75                  80                  85 gct aat ggc gcg gaa atg aac cag ttt cag gcc aag cag gtg ctg gac    704
Ala Asn Gly Ala Glu Met Asn Gln Phe Gln Ala Lys Gln Val Leu Asp
             90                  95                 100 cgg ggc gtc tat ggc gtc atc acc ccc cat gtc tcg acc gtc gag cag    752
Arg Gly Val Tyr Gly Val Ile Thr Pro His Val Ser Thr Val Glu Gln
        105                 110                 115 gcg tgg aac gcg gtc gcc tcc tgc cgc tat gcc aag ccc aag ggc gcg    800
Ala Trp Asn Ala Val Ala Ser Cys Arg Tyr Ala Lys Pro Lys Gly Ala
    120                 125                 130 gcc ctc tac gaa ccc aag ggc att cgc ggc gat ggc ccg gcg acg gcg    848
Ala Leu Tyr Glu Pro Lys Gly Ile Arg Gly Asp Gly Pro Ala Thr Ala
135                 140                 145                 150 gca cgc tat tgg ggc ctg tcg cag ccc gat tat tat gcc agg gcc gac    896
Ala Arg Tyr Trp Gly Leu Ser Gln Pro Asp Tyr Tyr Ala Arg Ala Asp
                155                 160                 165 gtc tgg ccg ctc gcc ccg cat ggc gaa ttg ctg gtc ggc atg atg tgc    944
Val Trp Pro Leu Ala Pro His Gly Glu Leu Leu Val Gly Met Met Cys
            170                 175                 180 gaa agc ccc gag gcg atc gac aat ctc gac gat atc ctg tcc gac gta    992
Glu Ser Pro Glu Ala Ile Asp Asn Leu Asp Asp Ile Leu Ser Asp Val
        185                 190                 195 ccg ggc atc ggc ctg gtg ctg atc ggc gag ggc gac ctt agc cag gcg   1040
Pro Gly Ile Gly Leu Val Leu Ile Gly Glu Gly Asp Leu Ser Gln Ala
    200                 205                 210 ctc ggc tat ccc cgc cag tac gag cat ccc gag gtg ctc gat gcg atg   1088
Leu Gly Tyr Pro Arg Gln Tyr Glu His Pro Glu Val Leu Asp Ala Met
215                 220                 225                 230 cgc cgg atc gtc gag acc tgc cac aag cac aag gtc gcg gtc ggc aat   1136
Arg Arg Ile Val Glu Thr Cys His Lys His Lys Val Ala Val Gly Asn
                235                 240                 245 ccg cac acc aat gcc aag aat gtc gag cgc ctg ctg ggc gag ggc tac   1184
Pro His Thr Asn Ala Lys Asn Val Glu Arg Leu Leu Gly Glu Gly Tyr
```

-continued

```
                      250                   255                   260
aag ttc ctg atg tcc gcg ccc agc cgc agc tat ggc gtg gtc ggt cag     1232
Lys Phe Leu Met Ser Ala Pro Ser Arg Ser Tyr Gly Val Val Gly Gln
            265                   270                   275 ggt cgc gaa ctg gcg ggc tac tagagcctga tcgtctgagg tggaagcgct        1283
Gly Arg Glu Leu Ala Gly Tyr
        280                285 gcttccaccg atggcgtgaa tcaggctcta atcgtagatt cccgaatttc agcacgacga   1343
aaaacaccga ctccggagca gggcgctccg ggaaaggcgg tcggctgccg gtcatcgacc   1403
ggcgccgaag ctatcgccgc aggcggcttt ccgattggcg ggcgcgcgcg cggaatgga    1463
atgctccccc caagatcatg agaatgggat aggtagatga acggcgcaga gagcctggtg   1523
acgaccctgg tcgaccaagg cgtggatatt tgtttcgcca accccggcac atcggaaatg   1583
cacttcctgt ccgcgctgga aaatccgcgg atgaagagcg tgctctgcct gtatgagggc   1643
gtctgcaccg cgcggccga cggctggtat cggatgaagg acaagccggc atcgaccctg    1703
ctgcaccttg gccgggcct cgccaacggc ctgtccaata tccacaatgc caagcgcgcc    1763
agttggcgat ggtcaatatc gtcggcgaac attcggccag ccactcaaat atgatccgcc   1823
gctgacatcg gatatcgagg ggctggcccg gcccttgagc cattgggtgc gccgcgccga   1883
atcctccacc tcgatcgcct gggacacggc gacggcggtg gccaaggcgt cggaacatcc   1943
cggccagatc gcgaccctga tcctgccggg cgacaccgcc tggaaggatg cgggccaggc   2003
gatcaccccc gcgccgatca cgccggtgcg ccgggcgccc gacggcgcgc ggatcgatgc   2063
gatcgcgcag gttctgcgct cgggcgaacc ggcgctcatc atcctcgcca acaagggcac   2123
gcgtggccgg cgctggaac tggcgggggca ggtcgcggcc agcaccggct gtcgcttggg   2183
cacccaattc ttcaccgccc ggatcgagcg cggcgcgggc cgcgtgccgc tggaacgcat   2243
cccctatgcc gtgccgcagg cgccgcctt cctccagggc ttcaagcatc tcatcacggt    2303
cgagaccagg gaaccggtcg ccttcttcag ctatcccgac aagcccagcc tgctgaaggc   2363
cccgggcacg atcgtccatg aactctgcgc cgcggacgag gacagcacgc tggcgttcga   2423
gatgctggtc gatgcgctgg ggctgggcac cgccgcgccg atcctgc                 2470
```

<210> SEQ ID NO 13
<211> LENGTH: 285
<212> TYPE: PRT
<213> ORGANISM: Sphingomonas sp.

<400> SEQUENCE: 13

```
Met Thr Asp Asn Arg Leu Asn Gly Val Ile Arg Ala Trp Glu Gln Gly
1               5                   10                  15

Lys Pro Ala Phe Ala Ala Phe Ser Lys Val Asp Lys Leu Thr Ala Gln
            20                  25                  30

Glu Met Thr Asp Ala Pro Tyr Asp Gly Ile Val Phe Glu Met Glu His
        35                  40                  45

Asn Pro Tyr Asp Val Gly Gly Leu Gly Asp Ala Leu Gln Tyr Met Leu
    50                  55                  60

Asn Arg Lys Lys Ile Ala Glu Ser Gly Ser Val Ala Pro Ser Val Thr
65                  70                  75                  80

Pro Leu Ala Arg Ile Pro Ala Asn Gly Ala Glu Met Asn Gln Phe Gln
                85                  90                  95

Ala Lys Gln Val Leu Asp Arg Gly Val Tyr Gly Val Ile Thr Pro His
            100                 105                 110
```

```
Val Ser Thr Val Glu Gln Ala Trp Asn Ala Val Ala Ser Cys Arg Tyr
        115                 120                 125

Ala Lys Pro Lys Gly Ala Ala Leu Tyr Glu Pro Lys Gly Ile Arg Gly
    130                 135                 140

Asp Gly Pro Ala Thr Ala Ala Arg Tyr Trp Gly Leu Ser Gln Pro Asp
145                 150                 155                 160

Tyr Tyr Ala Arg Ala Asp Val Trp Pro Leu Ala Pro His Gly Glu Leu
                165                 170                 175

Leu Val Gly Met Met Cys Glu Ser Pro Glu Ala Ile Asp Asn Leu Asp
            180                 185                 190

Asp Ile Leu Ser Asp Val Pro Gly Ile Gly Leu Val Leu Ile Gly Glu
        195                 200                 205

Gly Asp Leu Ser Gln Ala Leu Gly Tyr Pro Arg Gln Tyr Glu His Pro
    210                 215                 220

Glu Val Leu Asp Ala Met Arg Arg Ile Val Glu Thr Cys His Lys His
225                 230                 235                 240

Lys Val Ala Val Gly Asn Pro His Thr Asn Ala Lys Asn Val Glu Arg
                245                 250                 255

Leu Leu Gly Glu Gly Tyr Lys Phe Leu Met Ser Ala Pro Ser Arg Ser
            260                 265                 270

Tyr Gly Val Val Gly Gln Gly Arg Glu Leu Ala Gly Tyr
        275                 280                 285

<210> SEQ ID NO 14
<211> LENGTH: 1458
<212> TYPE: DNA
<213> ORGANISM: Burkholderia sp.
<220> FEATURE:
<221> NAME/KEY: CDS
<222> LOCATION: (531)..(1385)

<400> SEQUENCE: 14
caaggcatgg gagatgctgg ccgaaactga agctgccgat gtgcatccag accgggccga      60
tcggcctgcc gcaagtgcgc atgctggctg aaacagtttc cggcggtgaa catcatcctc     120
gatcaccttg gccgccctga cgtgctggac ggtccgccgt atgcgaacgc cgccagcctg     180
ttcgcgctcg ccgatctgcc caacatctac ctcaagctca cgccgcgcat tttcggcgat     240
gtgaagaaag agaaggccag cgcagagacc ttctttccgc gtgtggtcga agccttcggc     300
gcgcagcgcc tcgcgtgggg ctcgaacttt ccgacttcgc ccggcacgct caaggagatc     360
ctggcgacgg ctgaagcagg attggccagc ctcggcgaag aagagcgtac ctggatattc     420
ggcaagaccg cgcagaagct gtatccggtt ctgagctgag cctagacaac atgccaaccg     480
cgcgagcggc cgactgaagc ggcgccgtgc agcgagaaag agagatccac atg tcc         536
                                                         Met Ser
                                                           1 aac att cgc ctc aac agc atc atc cgt gcg ttc gaa tcg ggc aag gct      584
Asn Ile Arg Leu Asn Ser Ile Ile Arg Ala Phe Glu Ser Gly Lys Ala
      5                  10                  15 gcg cac gct gcg ttc gcc aag ctc gac aag cag acg gcc atc gaa atg      632
Ala His Ala Ala Phe Ala Lys Leu Asp Lys Gln Thr Ala Ile Glu Met
     20                  25                  30 agc gat tcg ccc tat gac ggc atc gtc ttc gag atg gag cac aac ccg      680
Ser Asp Ser Pro Tyr Asp Gly Ile Val Phe Glu Met Glu His Asn Pro
 35                  40                  45                  50 tac gat gtg agc gcg ctc ggc gac gca ttg cag tac atg ctc agc cgc      728
Tyr Asp Val Ser Ala Leu Gly Asp Ala Leu Gln Tyr Met Leu Ser Arg
             55                  60                  65
```

-continued aag cag atc gtc gag acg gcg tcg gtg gcg acc aag gtg acg ccg att 776
Lys Gln Ile Val Glu Thr Ala Ser Val Ala Thr Lys Val Thr Pro Ile
70 75 80 gct cgc atc ccc gcc aac ggc atc gag atg aac cag agc ttt gcg aag 824
Ala Arg Ile Pro Ala Asn Gly Ile Glu Met Asn Gln Ser Phe Ala Lys
85 90 95 cag gtg ctc gat cgc ggc gct tac ggc gtg atc tgg cca cac gtg gcg 872
Gln Val Leu Asp Arg Gly Ala Tyr Gly Val Ile Trp Pro His Val Ala
100 105 110 acc gtc gag cag gcg tac aac gcg gtc gca tcg tgt cgc tac gcg cgg 920
Thr Val Glu Gln Ala Tyr Asn Ala Val Ala Ser Cys Arg Tyr Ala Arg
115 120 125 130 ccg aag agc gcg ccg ctg tac gag ccg aag ggc gtg cgc ggc gac ggt 968
Pro Lys Ser Ala Pro Leu Tyr Glu Pro Lys Gly Val Arg Gly Asp Gly
135 140 145 ccg gcc aat gcg gcg cgc tac tgg ggt ctg tcg atg cag gag tac tac 1016
Pro Ala Asn Ala Ala Arg Tyr Trp Gly Leu Ser Met Gln Glu Tyr Tyr
150 155 160 gac aag gct gac gta tgg ccg ctc gcg ccg cag ggc gaa att ctc gtc 1064
Asp Lys Ala Asp Val Trp Pro Leu Ala Pro Gln Gly Glu Ile Leu Val
165 170 175 ggc ctg atg tgc gag agc aca cag gcg atc gaa aac ctc gac gac atc 1112
Gly Leu Met Cys Glu Ser Thr Gln Ala Ile Glu Asn Leu Asp Asp Ile
180 185 190 ctc gcc aac gta ccc ggc atc ggc ttc atc ctg atc ggc gag ggc gac 1160
Leu Ala Asn Val Pro Gly Ile Gly Phe Ile Leu Ile Gly Glu Gly Asp
195 200 205 210 ctc agc cag gaa ctg ggc ttc ccg cgc cag tac gaa cac ccc gaa gtc 1208
Leu Ser Gln Glu Leu Gly Phe Pro Arg Gln Tyr Glu His Pro Glu Val
215 220 225 gtc gat gcg atg cgc cag atc gtc gag acc tgc aag aag cac gat gtc 1256
Val Asp Ala Met Arg Gln Ile Val Glu Thr Cys Lys Lys His Asp Val
230 235 240 gtc gtc ggt cat ccg cac gtg acg gcg aag aac cat cga cgt ctg atg 1304
Val Val Gly His Pro His Val Thr Ala Lys Asn His Arg Arg Leu Met
245 250 255 gaa gag ggc tac cgc tac ctg atg tcg gcg ccg cag cgg act tac ggc 1352
Glu Glu Gly Tyr Arg Tyr Leu Met Ser Ala Pro Gln Arg Thr Tyr Gly
260 265 270 gtg gtc ggt ctc gcg cgc gat atg gct ggc tac tgatgaacgg cgccgagacc 1405
Val Val Gly Leu Ala Arg Asp Met Ala Gly Tyr
275 280 285 ctcgtcgcga ctctggtcga ccagggcgtc gacatctgct tcgccaaccc ggg 1458

<210> SEQ ID NO 15
<211> LENGTH: 285
<212> TYPE: PRT
<213> ORGANISM: Burkholderia sp.

<400> SEQUENCE: 15

Met Ser Asn Ile Arg Leu Asn Ser Ile Ile Arg Ala Phe Glu Ser Gly
1 5 10 15

Lys Ala Ala His Ala Ala Phe Ala Lys Leu Asp Lys Gln Thr Ala Ile
20 25 30

Glu Met Ser Asp Ser Pro Tyr Asp Gly Ile Val Phe Glu Met Glu His
35 40 45

Asn Pro Tyr Asp Val Ser Ala Leu Gly Asp Ala Leu Gln Tyr Met Leu
50 55 60

```
Ser Arg Lys Gln Ile Val Glu Thr Ala Ser Val Ala Thr Lys Val Thr
 65                  70                  75                  80

Pro Ile Ala Arg Ile Pro Ala Asn Gly Ile Glu Met Asn Gln Ser Phe
             85                  90                  95

Ala Lys Gln Val Leu Asp Arg Gly Ala Tyr Gly Val Ile Trp Pro His
        100                 105                 110

Val Ala Thr Val Glu Gln Ala Tyr Asn Ala Val Ala Ser Cys Arg Tyr
    115                 120                 125

Ala Arg Pro Lys Ser Ala Pro Leu Tyr Glu Pro Lys Gly Val Arg Gly
130                 135                 140

Asp Gly Pro Ala Asn Ala Ala Arg Tyr Trp Gly Leu Ser Met Gln Glu
145                 150                 155                 160

Tyr Tyr Asp Lys Ala Asp Val Trp Pro Leu Ala Pro Gln Gly Glu Ile
                165                 170                 175

Leu Val Gly Leu Met Cys Glu Ser Thr Gln Ala Ile Glu Asn Leu Asp
            180                 185                 190

Asp Ile Leu Ala Asn Val Pro Gly Ile Gly Phe Ile Leu Ile Gly Glu
        195                 200                 205

Gly Asp Leu Ser Gln Glu Leu Gly Phe Pro Arg Gln Tyr Glu His Pro
    210                 215                 220

Glu Val Val Asp Ala Met Arg Gln Ile Val Glu Thr Cys Lys Lys His
225                 230                 235                 240

Asp Val Val Gly His Pro His Val Thr Ala Lys Asn His Arg Arg
                245                 250                 255

Leu Met Glu Glu Gly Tyr Arg Tyr Leu Met Ser Ala Pro Gln Arg Thr
            260                 265                 270

Tyr Gly Val Val Gly Leu Ala Arg Asp Met Ala Gly Tyr
        275                 280                 285

<210> SEQ ID NO 16
<211> LENGTH: 471
<212> TYPE: DNA
<213> ORGANISM: Sphingomonas sp.

<400> SEQUENCE: 16
tggagagttt gatcctggct cagaacgaac gctggcggca tgcctaacac atgcaagtcg      60
aacgagatct tcggatctag tggcgcacgg gtgcgtaacg cgtgggaatc tgcccttgc     120 ttcggaataa cagtgagaaa ttactgctaa taccggatga tgtcttcgga ccaaagattt     180
atcggcaaag gatgagcccg cgtaggatta gctagttggt ggggtaatgg cctaccaagg     240
cgacgatcct agctggtct gagaggatga tcagccacac tgggactgag acacggccca     300
gactcctacg ggaggcagca gtggggaata ttggacaatg ggcgaaagcc tgatccagca     360
atgccgcgtg agtgatgaag gccttagggt tgtaaagctc ttttaccagg gatgataatg     420
acagtacctg gagaataagc tccggctaac tccgtgccag cagccgcggt a              471

<210> SEQ ID NO 17
<211> LENGTH: 471
<212> TYPE: DNA
<213> ORGANISM: Sphingomonas sp.

<400> SEQUENCE: 17
tggagagttt gatcctggct cagaacgaac gctggcggca tgcctaatac atgcaagtcg      60
aacgaactct tcggagttag tggcgcacgg gtgcgtaacg cgtgggaatc tgcccttggg     120
ttcggaataa cttctggaaa cggaagctaa taccggatga tgacgtaagt ccaaagattt     180
```

```
atcgcccaag gatgagcccg cgtaggatta gctagttggt gaggtaaagg ctcaccaagg    240
cgacgatcct tagctggtct gagaggatgr tcagccacac tgggactgag acacggccca    300
gactcctacg ggaggcagca gtagggaata ttggacaatg ggcgaaagcc tgatccagca    360
atgccgcgtg agtgatgaag gccttagggt tgtaaagctc ttttacccgg gatgataatg    420
acagtaccgg gagaataagc tccggctaac tccgtgccag cagccgcggt a             471
```

<210> SEQ ID NO 18
<211> LENGTH: 522
<212> TYPE: DNA
<213> ORGANISM: Burkholderia sp.

<400> SEQUENCE: 18

```
tggagagttt gatcctggct cagattgaac gctggcggca tgccttacac atgcaagtcg    60
gacggcagcg cggggcaac cctggcggcg agtggcgaac gggtgagtaa tacatcggaa    120
cgtgtcctgg agtgggggat agcccggcga agccggatt aataccgcat acgctctatg     180
gaggaaagcg gggatcttc ggacctcgcg ctcaaggggc ggccgatggc agattagcta     240
gttggtgggg taaaggccta ccaaggcgac gatctgtagc tggtctgaga ggacgaccag    300
ccacactggg actgagacac ggcccagact cctacgggag gcagcagtgg ggaattttgg    360
acaatggggg caaccctgat ccagcaatgc cgcgtgtgtg aagaaggcct tcgggttgta    420
aagcactttt gtccggaaag aaaacctccg tcctaatacg gtgggggat gacggtaccg    480 gaagaataag caccggctaa ctacgtgcca gcagccgcgg ta                       522
```

<210> SEQ ID NO 19
<211> LENGTH: 30
<212> TYPE: DNA
<213> ORGANISM: Artificial Sequence
<220> FEATURE:
<223> OTHER INFORMATION: Synthetic DNA

<400> SEQUENCE: 19

```
atccatatgt ccaacattcg cctcaacagc                                      30
```

<210> SEQ ID NO 20
<211> LENGTH: 33
<212> TYPE: DNA
<213> ORGANISM: Artificial Sequence
<220> FEATURE:
<223> OTHER INFORMATION: Synthetic DNA

<400> SEQUENCE: 20

```
cgcctgcagt cagtagccag ccatatcgcg cgc                                  33
```

<210> SEQ ID NO 21
<211> LENGTH: 34
<212> TYPE: DNA
<213> ORGANISM: Artificial Sequence
<220> FEATURE:
<223> OTHER INFORMATION: Synthetic DNA

<400> SEQUENCE: 21

```
ccggaattcc atgaaggaat gatctgagat gacc                                 34
```

<210> SEQ ID NO 22
<211> LENGTH: 36
<212> TYPE: DNA
<213> ORGANISM: Artificial Sequence
<220> FEATURE:

<223> OTHER INFORMATION: Synthetic DNA

<400> SEQUENCE: 22
aaaaactgca gctagtagcc cgccagttcg cgaccc                    36

<210> SEQ ID NO 23
<211> LENGTH: 285
<212> TYPE: PRT
<213> ORGANISM: Artificial Sequence
<220> FEATURE:
<223> OTHER INFORMATION: Consensus Peptide Sequence
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (20)..(22)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (34)..(35)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (42)..(42)
<223> OTHER INFORMATION: Xaa can be any naturally occurring amino acid
<220> FEATURE:
<221> NAME/KEY: misc_feature
<222> LOCATION: (54)..(55)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid
<220> FEATURE:
<221> NAME/KEY: misc_feature
<222> LOCATION: (68)..(68)
<223> OTHER INFORMATION: Xaa can be any naturally occurring amino acid
<220> FEATURE:
<221> NAME/KEY: misc_feature -continued

```
<222> LOCATION: (70)..(70)
<223> OTHER INFORMATION: Xaa can be any naturally occurring amino acid
<220> FEATURE:
<221> NAME/KEY: misc_feature
<222> LOCATION: (72)..(73)
<223> OTHER INFORMATION: Xaa can be any naturally occurring amino acid
<220> FEATURE:
<221> NAME/KEY: misc_feature
<222> LOCATION: (77)..(78)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (90)..(90)
<223> OTHER INFORMATION: Xaa can be any naturally occurring amino acid
<220> FEATURE:
<221> NAME/KEY: misc_feature
<222> LOCATION: (95)..(96)
<223> OTHER INFORMATION: Xaa can be any naturally occurring amino acid
<220> FEATURE:
<221> NAME/KEY: misc_feature
<222> LOCATION: (105)..(105)
<223> OTHER INFORMATION: Xaa can be any naturally occurring amino acid
<220> FEATURE:
<221> NAME/KEY: misc_feature
<222> LOCATION: (110)..(110)
<223> OTHER INFORMATION: Xaa can be any naturally occurring amino acid
<220> FEATURE:
<221> NAME/KEY: misc_feature
<222> LOCATION: (114)..(114)
<223> OTHER INFORMATION: Xaa can be any naturally occurring amino acid
<220> FEATURE:
<221> NAME/KEY: misc_feature
<222> LOCATION: (120)..(120)
<223> OTHER INFORMATION: Xaa can be any naturally occurring amino acid
<220> FEATURE:
<221> NAME/KEY: misc_feature
<222> LOCATION: (122)..(122)
<223> OTHER INFORMATION: Xaa can be any naturally occurring amino acid
<220> FEATURE:
<221> NAME/KEY: misc_feature
<222> LOCATION: (126)..(126)
<223> OTHER INFORMATION: Xaa can be any naturally occurring amino acid
<220> FEATURE:
<221> NAME/KEY: misc_feature
<222> LOCATION: (130)..(130)
<223> OTHER INFORMATION: Xaa can be any naturally occurring amino acid
<220> FEATURE:
<221> NAME/KEY: misc_feature
<222> LOCATION: (132)..(133)
<223> OTHER INFORMATION: Xaa can be any naturally occurring amino acid
<220> FEATURE:
<221> NAME/KEY: misc_feature
<222> LOCATION: (135)..(135)
<223> OTHER INFORMATION: Xaa can be any naturally occurring amino acid
<220> FEATURE:
<221> NAME/KEY: misc_feature
<222> LOCATION: (142)..(142)
<223> OTHER INFORMATION: Xaa can be any naturally occurring amino acid
<220> FEATURE:
<221> NAME/KEY: misc_feature
<222> LOCATION: (149)..(149)
<223> OTHER INFORMATION: Xaa can be any naturally occurring amino acid
<220> FEATURE:
<221> NAME/KEY: misc_feature
<222> LOCATION: (158)..(160)
<223> OTHER INFORMATION: Xaa can be any naturally occurring amino acid
<220> FEATURE:
<221> NAME/KEY: misc_feature
<222> LOCATION: (163)..(164)
<223> OTHER INFORMATION: Xaa can be any naturally occurring amino acid
<220> FEATURE:
<221> NAME/KEY: misc_feature
<222> LOCATION: (173)..(173)
<223> OTHER INFORMATION: Xaa can be any naturally occurring amino acid
<220> FEATURE:
```

```
<221> NAME/KEY: misc_feature
<222> LOCATION: (176)..(176)
<223> OTHER INFORMATION: Xaa can be any naturally occurring amino acid
<220> FEATURE:
<221> NAME/KEY: misc_feature
<222> LOCATION: (180)..(180)
<223> OTHER INFORMATION: Xaa can be any naturally occurring amino acid
<220> FEATURE:
<221> NAME/KEY: misc_feature
<222> LOCATION: (185)..(186)
<223> OTHER INFORMATION: Xaa can be any naturally occurring amino acid
<220> FEATURE:
<221> NAME/KEY: misc_feature
<222> LOCATION: (189)..(189)
<223> OTHER INFORMATION: Xaa can be any naturally occurring amino acid
<220> FEATURE:
<221> NAME/KEY: misc_feature
<222> LOCATION: (196)..(197)
<223> OTHER INFORMATION: Xaa can be any naturally occurring amino acid
<220> FEATURE:
<221> NAME/KEY: misc_feature
<222> LOCATION: (203)..(204)
<223> OTHER INFORMATION: Xaa can be any naturally occurring amino acid
<220> FEATURE:
<221> NAME/KEY: misc_feature
<222> LOCATION: (214)..(214)
<223> OTHER INFORMATION: Xaa can be any naturally occurring amino acid
<220> FEATURE:
<221> NAME/KEY: misc_feature
<222> LOCATION: (217)..(217)
<223> OTHER INFORMATION: Xaa can be any naturally occurring amino acid
<220> FEATURE:
<221> NAME/KEY: misc_feature
<222> LOCATION: (222)..(222)
<223> OTHER INFORMATION: Xaa can be any naturally occurring amino acid
<220> FEATURE:
<221> NAME/KEY: misc_feature
<222> LOCATION: (227)..(228)
<223> OTHER INFORMATION: Xaa can be any naturally occurring amino acid
<220> FEATURE:
<221> NAME/KEY: misc_feature
<222> LOCATION: (231)..(232)
<223> OTHER INFORMATION: Xaa can be any naturally occurring amino acid
<220> FEATURE:
<221> NAME/KEY: misc_feature
<222> LOCATION: (236)..(236)
<223> OTHER INFORMATION: Xaa can be any naturally occurring amino acid
<220> FEATURE:
<221> NAME/KEY: misc_feature
<222> LOCATION: (238)..(238)
<223> OTHER INFORMATION: Xaa can be any naturally occurring amino acid
<220> FEATURE:
<221> NAME/KEY: misc_feature
<222> LOCATION: (241)..(241)
<223> OTHER INFORMATION: Xaa can be any naturally occurring amino acid
<220> FEATURE:
<221> NAME/KEY: misc_feature
<222> LOCATION: (243)..(243)
<223> OTHER INFORMATION: Xaa can be any naturally occurring amino acid
<220> FEATURE:
<221> NAME/KEY: misc_feature
<222> LOCATION: (246)..(246)
<223> OTHER INFORMATION: Xaa can be any naturally occurring amino acid
<220> FEATURE:
<221> NAME/KEY: misc_feature
<222> LOCATION: (249)..(250)
<223> OTHER INFORMATION: Xaa can be any naturally occurring amino acid
<220> FEATURE:
<221> NAME/KEY: misc_feature
<222> LOCATION: (254)..(255)
<223> OTHER INFORMATION: Xaa can be any naturally occurring amino acid
<220> FEATURE:
<221> NAME/KEY: misc_feature
<222> LOCATION: (258)..(259)
<223> OTHER INFORMATION: Xaa can be any naturally occurring amino acid
<220> FEATURE:
<221> NAME/KEY: misc_feature
<222> LOCATION: (263)..(264)
<223> OTHER INFORMATION: Xaa can be any naturally occurring amino acid
```

```
<220> FEATURE:
<221> NAME/KEY: misc_feature
<222> LOCATION: (270)..(270)
<223> OTHER INFORMATION: Xaa can be any naturally occurring amino acid
<220> FEATURE:
<221> NAME/KEY: misc_feature
<222> LOCATION: (272)..(272)
<223> OTHER INFORMATION: Xaa can be any naturally occurring amino acid
<220> FEATURE:
<221> NAME/KEY: misc_feature
<222> LOCATION: (278)..(279)
<223> OTHER INFORMATION: Xaa can be any naturally occurring amino acid
<220> FEATURE:
<221> NAME/KEY: misc_feature
<222> LOCATION: (281)..(282)
<223> OTHER INFORMATION: Xaa can be any naturally occurring amino acid

<400> SEQUENCE: 23

Met Xaa Xaa Xaa Arg Leu Asn Xaa Xaa Ile Arg Ala Xaa Glu Xaa Gly
1               5                   10                  15

Lys Xaa Ala Xaa Xaa Xaa Phe Xaa Lys Xaa Asp Lys Xaa Thr Ala Xaa
            20                  25                  30

Glu Xaa Xaa Asp Xaa Pro Tyr Asp Gly Xaa Val Phe Glu Met Glu His
        35                  40                  45

Asn Pro Tyr Asp Val Xaa Xaa Leu Gly Asp Ala Leu Gln Tyr Met Leu
    50                  55                  60

Xaa Arg Lys Xaa Ile Xaa Glu Xaa Xaa Ser Val Ala Xaa Xaa Val Thr
65                  70                  75                  80

Pro Xaa Ala Arg Ile Pro Ala Asn Gly Xaa Glu Met Asn Gln Xaa Xaa
            85                  90                  95

Ala Lys Gln Val Leu Asp Arg Gly Xaa Tyr Gly Val Ile Xaa Pro His
            100                 105                 110

Val Xaa Thr Val Glu Gln Ala Xaa Asn Xaa Val Ala Ser Xaa Arg Tyr
        115                 120                 125

Ala Xaa Pro Xaa Xaa Ala Xaa Leu Tyr Glu Pro Lys Gly Xaa Arg Gly
    130                 135                 140

Asp Gly Pro Ala Xaa Ala Ala Arg Tyr Trp Gly Leu Ser Xaa Xaa Xaa
145                 150                 155                 160

Tyr Tyr Xaa Xaa Ala Asp Val Trp Pro Leu Ala Pro Xaa Gly Glu Xaa
            165                 170                 175

Leu Val Gly Xaa Met Cys Glu Ser Xaa Xaa Ala Ile Xaa Asn Leu Asp
            180                 185                 190

Asp Ile Leu Xaa Xaa Val Pro Gly Ile Gly Xaa Xaa Leu Ile Gly Glu
            195                 200                 205

Gly Asp Leu Ser Gln Xaa Leu Gly Xaa Pro Arg Gln Tyr Xaa His Pro
    210                 215                 220

Glu Val Xaa Xaa Ala Met Xaa Xaa Ile Val Glu Xaa Cys Xaa Lys His
225                 230                 235                 240

Xaa Val Xaa Val Gly Xaa Pro His Xaa Xaa Ala Lys Asn Xaa Xaa Arg
            245                 250                 255

Leu Xaa Xaa Glu Gly Tyr Xaa Xaa Leu Met Ser Ala Pro Xaa Arg Xaa
            260                 265                 270

Tyr Gly Val Val Gly Xaa Xaa Arg Xaa Xaa Ala Gly Tyr
            275                 280                 285
```

ALDOLASE, AND METHOD FOR PRODUCING OPTICALLY ACTIVE IHOG AND MONATIN

CROSS-REFERENCE TO RELATED APPLICATIONS

The present application is a continuation of U.S. application Ser. No. 11/362,915, filed on Feb. 28, 2006, now U.S. Pat. No. 7,371,549, which is a divisional of U.S. application Ser. No. 11/146,093, filed on Jun. 7, 2005, now U.S. Pat. No. 7,241,599, and claims priority to Japanese Patent Application No. 2004-169188, filed on Jun. 7, 2004, and Japanese Patent Application No. 2004-375769, filed on Dec. 27, 2004, the entire contents of which are incorporated herein by reference.

BACKGROUND OF THE INVENTION

1. Field of the Invention

The present invention relates to a novel aldolase that produces 4-(indol-3-ylmethyl)-4-hydroxy-2-oxoglutaric acid (IHOG), which is a precursor of monatin, and methods for producing 4R-IHOG and 4R-monatin by the use thereof.

2. Discussion of the Background 4-(Indole-3-ylmethyl)-4-hydroxy-2-glutamic acid(3-(1-amino-1,3-dicarboxy-3-hydroxy-butane-4-yl)indole (hereinafter referred to as monatin) represented by the following structural formula is found in the root of the plant, *Schlerochiton ilicifolius*, and because of its remarkably high sweetness intensity is a compound that is anticipated to be a sweetener with a low caloric value (see JP-P-64-25757-A).

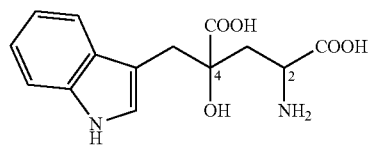

4-(Indol-3-ylmethyl)-4-hydroxy-glutamic acid

As shown in the foregoing structure, monatin has two asymmetric carbon atoms at positions 2 and 4. The naturally occurring stereoisomer thereof was reported to be a (2S,4S) isomer. Three additional stereoisomers are possible, and it has been confirmed that each of them has sweetness intensity that is several ten to several thousand times greater than that of sucrose (Table 1).

TABLE 1

| Optical Isomer | Sweetness (vs. Sucrose) |
|---|---|
| 2R,4R | 2700 times |
| 2R,4S | 1300 times |
| 2S,4R | 300 times |
| 2S,4S | 50 times |

As is shown in Table 1, in addition to the naturally occurring (2S,4S)-monatin the other stereoisomers have the sweetness intensity with high scale factor. Particularly, (2R,4R)-monatin has a remarkably high sweetness intensity, which is 2,700 times greater than that of sucrose. As such, the (2R,4R) stereoisomer is particularly promising as a sweetening agent or a sweetening agent ingredient (sweetener). Therefore, a critical demand exists for the development of a method for efficiently producing monatin with high content of (2R,4R)-monatin.

To address this demand, the present inventors have developed a new method for synthesizing monatin by performing the following reactions (a) and (b) using commercially available indole pyruvic acid and pyruvic acid as reagents (International Publication No. 03/056026 Pamphlet).

(a) Reaction step of synthesizing a precursor keto acid (IHOG) by aldol condensation of indole pyruvic acid and pyruvic acid (or oxaloacetic acid).

(b) Reaction step of aminating position 2 of IHOG.

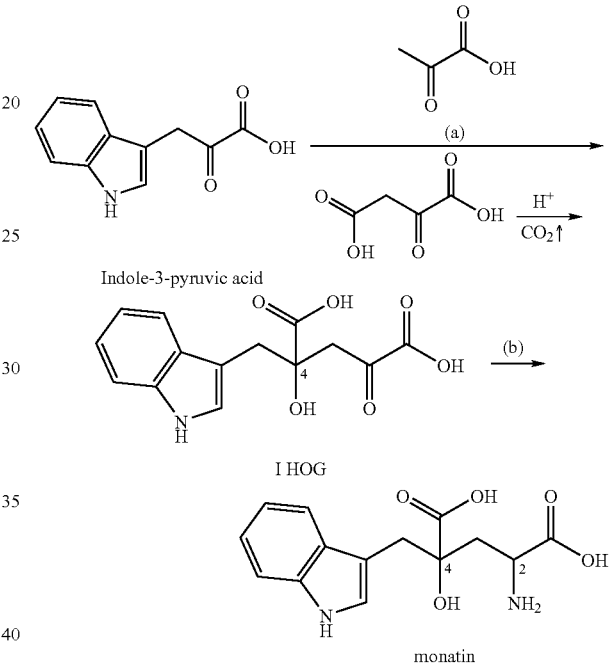

International Publication No. 04/018672 Pamphlet discloses aldolases derived from *Pseudomonas taetrolens* and *Pseudomonas coronafaciens* as enzymes that are useful for producing the precursor keto acid (IHOG) from indole pyruvic acid and pyruvic acid (or oxaloacetic acid) in the aldol condensation of (a) in the aforementioned synthetic route of monatin. These aldolases have also been found to catalyze a reaction for the production of a keto acid such as 4-phenylmethyl-4-hydroxy-2-oxoglutaric acid (PHOG) in addition to IHOG.

There are two isomers, 4R-isomer and 4S-isomer in IHOG. In order to efficiently produce the (2R,4R)-monatin (i.e., the isomer with highest sweetness), it is desirable to preferentially produce IHOG of a 4R-isomer (4R-IHOG) (4S-isomer is referred to as 4S-IHOG) in the aldol condensation reaction of (a) in the aforementioned synthetic route of monatin, and obtain 4R-isomer-rich IHOG. A chiral molecule often exhibits a physiological activity that is different by each isomer, and it is also likely that IHOG exhibits different characteristics by each isomer. Thus, separately produced 4R- and 4S-isomers may be utilized for uses other than the use as the monatin precursor. Therefore, it would be highly beneficial to industry to develop a method for producing preferentially one isomer of IHOG (e.g., one of 4R-IHOG and 4S-IHOG).

SUMMARY OF THE INVENTION

However, in previous chemical synthetic systems, the IHOG produced was a mixture of the 4R- and 4S-isomers (racemate). The present inventors have obtained an aldolase derived from *Pseudomonas taetrolens* to use as an aldolase for the synthesis of IHOG, however, it has been demonstrated that IHOG produced by said aldolase is not 4R-isomer-rich and rather slightly 4S-isomer-rich depending on a reaction condition (International Publication No. 03/056026 Pamphlet and International Publication No. 04/018672 Pamphlet). Heretofore, an aldolase that preferentially produces 4R-IHOG has not been reported. Therefore currently, no method for efficiently producing the 4R-IHOG, particularly the 4R-isomer-rich IHOG has been established.

The present invention has been made in light of the above, and it is an object of the invention to provide a novel aldolase that produces PHOG and IHOG. In particular, it is an object of the present invention to provide a novel aldolase that produces 4R-IHOG, and methods for producing IHOG and monatin by the use thereof.

As a result of extensive studies to satisfy the above goal, the present inventors have found that an aldolase suitable for use in the synthesis of 4R-IHOG exists in a certain microorganism, and by the use thereof a method for producing 4R-IHOG and 4R-monatin may be provided.

That is, the present invention includes at least the following embodiments:

[1]
A method for producing (4R)-4-(indole-3-ylmethyl)-4-hydroxy-2-oxoglutaric acid (4R-IHOG) or a salt thereof of formula (1):

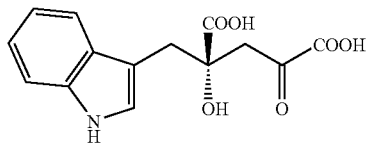

(1)

by reacting indole-3-pyruvic acid with pyruvic acid or oxaloacetic acid to produce 4R-IHOG with an optical purity of 70% or more, in the presence of a protein or a microorganism containing the protein,
wherein the protein is selected from the group consisting of (a) and (b):
  (a) a protein comprising the amino acid sequence in SEQ ID NO:2,
  (b) a protein that is a least 70% homologous to the amino acid sequence in SEQ ID NO:2 and has a 4R-aldolase activity.

[2]
A method for producing 4R-monatin or a salt thereof comprising:
reacting indole-3-pyruvic acid with pyruvic acid or oxaloacetic acid in the presence of a protein or a microorganism containing the protein to preferentially produce 4R-IHOG or a salt thereof,
wherein the protein is selected from the group consisting of (a) and (b):
  (a) a protein comprising an amino acid sequence in SEQ ID NO:2,
  (b) a protein that is a least 70% homologous to the amino acid sequence in SEQ ID NO:2 and has a 4R-aldolase activity; and
converting a carbonyl group of 4R-IHOG or the salt thereof to an amino group to produce 4R-monatin, or a salt thereof, of the formula (2) with an optical purity of at least 90%,

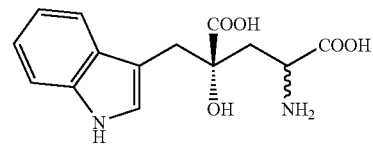

(2)

wherein a bond of a wavy line represents that both R- and S-configurations are included.

[3]
The method for producing 4R-monatin or the salt thereof according to item [2],
wherein said converting is by amination in the presence of an enzyme acting on 4R-IHOG.

[4]
A method for producing 4R-monatin or a salt thereof according to item [2] or [3],
wherein said converting is by a process comprising,
reacting 4-(indole-3-ylmethyl)-4-hydroxy-2-oxoglutaric acid contained in a reaction mixture with an amine compound or a salt thereof of formula (3):

$$H_2N-O-R \qquad (3)$$

wherein R represents a hydrogen atom, an alkyl, aryl or aralkyl group, under a neutral or alkali conditions to produce 4-hydroxy-4-(3-indolylmethyl)-2-hydroxyiminoglutaric acid (IHOG-oxime) or a salt thereof of formula (4):

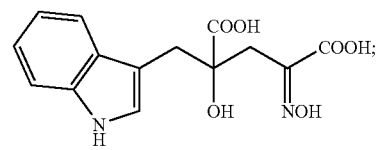

(4)

and
crystallizing a 4R-isomer of the produced IHOG-oxime or the salt thereof; and
reducing the crystallized 4R-isomer of IHOG-oxime or the salt thereof to produce 4R-monatin or the salt thereof with an optical purity of at least 90%.

[5]
The method for producing 4R-monatin according to item [4],
wherein the amine compound of the formula (3) is at least one amine compound selected from the group consisting of hydroxylamine, methoxyamine and benzyloxyamine.

[6]
The method for producing 4R-monatin according to item [4] or [5], wherein the 4R-isomer of IHOG-oxime or the salt thereof is reduced in the presence of hydrogen and a hydrogenated catalyst.

[7]
The method for producing 4R-monatin or the salt thereof according to any one of items [4] to [6],
wherein (2R,4R)-monatin is recovered by crystallization during said crystallizing.

[8]
The method for producing 4R-monatin or the salt thereof according to any one of items [4] or [7],
wherein during said crystallizing, crystallization is performed with a crystallization solvent selected from the group consisting of water, an alcohol solvent and an aqueous alcohol solvent.

[9]
The method according to any one of items [1] to [8],
wherein the protein used in the method is derived from a microorganism selected from bacteria belonging to genus *Sphingomonas* or *Burkholderia*.

[10]
The method according to item [9],
wherein the microorganism is selected from the group consisting of *Sphingomonas* sp. AJ110329 strain, *Sphingomonas* sp. AJ110372 strain, and *Burkholderia* sp. AJ110371 strain.

[11]
A protein selected from the group consisting of the following (a) to (c):
   (a) a protein comprising an amino acid sequence in SEQ ID NO:2;
   (b) a protein that is at least 70% homologous to the amino acid sequence in SEQ ID NO:2 and has a 4R-aldolase activity; and
   (c) a protein comprising an amino acid sequence containing a mutation selected from the group consisting of substitution, deletion, insertion, addition and inversion of one or several amino acid residues in the amino acid sequence in SEQ ID NO:2, and having an aldolase activity.

[12]
The protein according to item [11],
wherein the protein that is at least 70% homologous to the amino acid sequence in SEQ ID NO:2 and has the 4R-aldolase activity is a protein comprising an amino acid sequence described in SEQ ID NO:13 or 15.

[13]
A DNA encoding the protein described in item [11] or [12].

[14]
A DNA of the following (d) or (e):
   (d) a DNA composed of a nucleotide sequence in SEQ ID NO:1 or a nucleotide sequence of nucleotide Nos. 210 to 1004 in SEQ ID NO:1; and
   (e) a DNA that hybridizes with a DNA comprising a nucleotide sequence complementary to the nucleotide sequence in SEQ ID NO:1 or to a DNA comprising a nucleotide sequence complementary to the nucleotide sequence of nucleotide Nos. 210 to 1004 in SEQ ID NO:1 under stringent conditions, and encodes a protein having an aldolase activity.

[15]
The DNA according to item [14],
wherein the DNA that hybridizes with a DNA comprising a nucleotide sequence complementary to the nucleotide sequence in SEQ ID NO:1 or to a DNA comprising a nucleotide sequence complementary to the nucleotide sequence of nucleotide Nos. 210 to 1004 in SEQ ID NO:1 under stringent conditions and encodes the protein having aldolase activity, is any one of
   (f) a DNA composed a nucleotide sequence of SEQ ID NO:12 or a nucleotide sequence of nucleotide Nos. 399 to 1253 in SEQ ID NO:12, or
   (g) a DNA composed of a nucleotide sequence of SEQ ID NO:14 or a nucleotide sequence of nucleotide Nos. 531 to 1385 in SEQ ID NO:14.

[16]
A recombinant DNA obtained by linking the DNA selected from the group consisting of item [14] and [15] to a vector DNA.

[17]
A cell transformed with the recombinant DNA according to item [16].

[18]
A method for producing a protein having an aldolase activity comprising:
   cultivating the cells according to claim 17 in a medium; and
   accumulating the protein having the aldolase activity in the medium and/or the cells.

By the use of aldolase of the present invention, 4R-IHOG may be preferentially produced from indole pyruvic acid and pyruvic acid (or oxaloacetic acid). Since 4R-monatin may be synthesized by aminating the produced 4R-IHOG, the aldolase may also be used highly advantageously for the production of monatin with high sweetness.

Conventionally, when the 4R-isomer is isolated from racemic IHOG (4R,4S-IHOG), it has been necessary that the racemic IHOG is oximated and the yielded 4-hydroxy-4-(3-indolylmethyl)-2-hydroxyiminoglutaric acid (IHOG-oxime) is reacted with chiral amines to crystallize IHOG-oxime of the 4R-isomer (4R-IHOG-oxime). On the contrary, in accordance with the present invention, no optical resolution using the chiral amines is required upon the crystallization because 4R-isomer-rich IHOG may be produced in a stage of the aldol condensation. After the oximation, 4R-IHOG-oxime may be crystallized directly. Therefore, it becomes possible to diminish the purification process of 4R-IHOG.

The above objects highlight certain aspects of the invention. Additional objects, aspects and embodiments of the invention are found in the following detailed description of the invention.

BRIEF DESCRIPTION OF THE FIGURES

A more complete appreciation of the invention and many of the attendant advantages thereof will be readily obtained as the same becomes better understood by reference to the following Figures in conjunction with the detailed description below.

FIG. 1 shows a homology comparison of aldolases of the present invention.

DETAILED DESCRIPTION OF THE INVENTION

Figure 2:
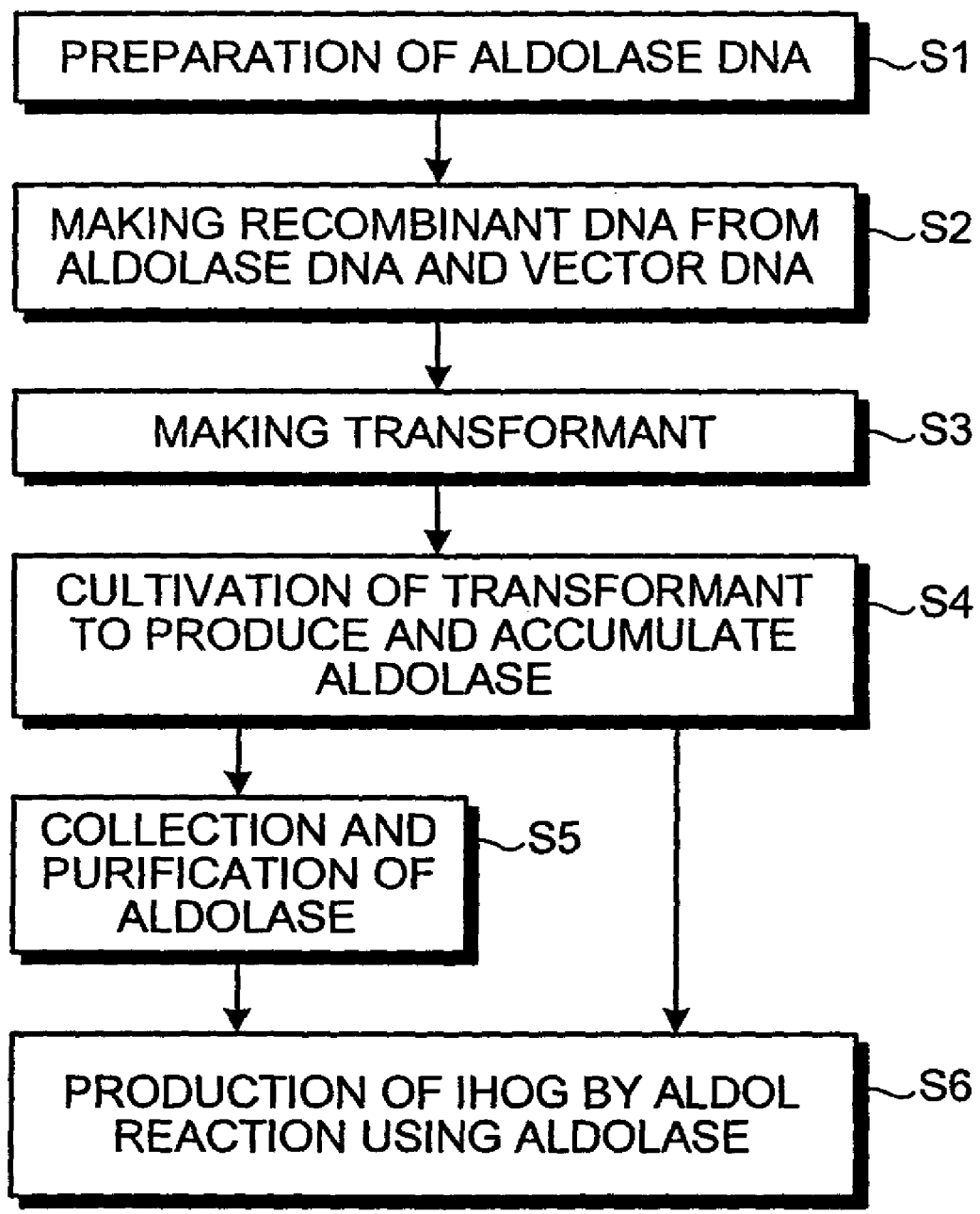
FIG. 2 presents a flowchart showing production steps of the aldolase of the present invention.

Unless specifically defined, all technical and scientific terms used herein have the same meaning as commonly understood by a skilled artisan in enzymology, biochemistry, cellular biology, molecular biology, and the food sciences.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will control. Further, the materials, methods, and examples are illustrative only and are not intended to be limiting, unless otherwise specified.

Based on their studies, the present inventors have determined that some bacterial strains which produce aldolase having an activity which preferentially synthesizes 4R-IHOG exist, and have established methods for producing 4R-IHOG and 4R-monatin.

To this end, the present invention will be described in detail in the order of

[I] method for producing optically active IHOG, and

[II] method for producing optically active monatin, with reference to the appended drawings.

[I] Method for Producing Optically Active IHOG (1) Reaction

The method for producing 4R-IHOG of the present invention involves preferentially producing 4R-IHOG represented by formula (1):

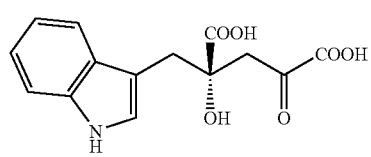

(1)

by reacting indole pyruvic acid represented by formula (5):

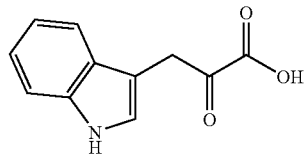

(5)

with pyruvic acid or oxaloacetic acid represented by formula (6):

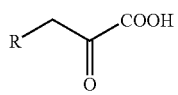

(6)

wherein R represents a hydrogen atom or a carboxyl group. The reaction above is performed in the presence of a protein that catalyzes the reaction.

The aforementioned phrase "protein that catalyzes the reaction" is preferably a protein having 4R-aldolase activity, and may be obtained from a microorganism or chemically synthesized. The 4R-aldolase activity refers to catalytic activity of a reaction in which 4R-IHOG represented by formula (1) is preferentially produced by aldol condensation of indole pyruvic acid of formula (5) with pyruvic acid or oxaloacetic acid represented by formula (6), and/or a reaction in which 4R-PHOG is preferentially produced from phenyl pyruvic acid and pyruvic acid. The protein is not particularly limited and any protein meeting the aforementioned criteria may be used in the present invention.

As used herein, producing "4R-IHOG preferentially" indicates that an optical purity of an R-isomer is greater than that of an S-isomer at position 4, and that a reaction efficiency where the optical purity of the R-isomer is preferably at least 70% and particularly preferably at least 90% may be accomplished. Depending on reaction conditions, the optical purity value varies, but those skilled in the art may easily set optimal conditions of the reaction. Thus, any method in which the aforementioned optical purity is accomplished at around the optimal condition is included in the present invention, even if there may be some cases where the above optical purity has not been accomplished when the reaction condition is changed. A reaction involving employment of the protein capable of being applied for the invention may be performed to obtain the optical purity equal to or less than the above by controlling the reaction condition for the purpose of adjusting to a desired mixture ratio of the 4R- and 4S-isomers. Such a case is also included in the method of the present invention. The optical purity of 4R-IHOG may be determined as an enantiomeric excess (% e.e.) by ([4R-IHOG]-[4S-IHOG])/([4R-IHOG]+[4S-IHOG])×100.

An aldolase described later in the section titled "(2) Protein having an aldolase activity" is preferable to catalyze the aforementioned reaction. Upon identifying the presence of reaction, the aldolase may be obtained by cultivating microbial cells that produce the protein (aldolase), which catalyzes the reaction. Alternatively, the aldolase may be obtained by making a transformant that produces the protein that catalyzes the reaction by a recombinant DNA technique and cultivating the transformant.

The protein that catalyzes the reaction may be added to the reaction system in any form as long as the protein can catalyze the reaction in which 4R-IHOG is preferentially synthesized. More specifically, the protein that catalyzes the reaction may be added to the reaction system alone, or a composition having the aldolase activity comprising the protein (aldolase) may be added to the reaction system.

As used herein, the "composition having the aldolase activity" may be those containing the protein (aldolase) that catalyzes the reaction, and this term includes specifically a culture, a medium (culture from which microbial cells have been removed), microbial cells (including cultured microbial cells and washed microbial cells), a treated microbial cell product obtained by disrupting or lysing the microbial cells, or a composition (crude enzyme solution, purified enzyme) having the aldolase activity obtained by purifying the medium and/or the cells. For example, when the optically active IHOG is produced using aldolase-producing microorganisms or cells transformed with the recombinant DNA, a substrate may be directly added into the medium with cultivating, and the microbial cells harvested from the medium or the washed microbial cells may be used. Treated microbial cells obtained by disrupting or lysing the microbial cells may be used directly, or the aldolase may be collected from the treated microbial cell products and used as the crude enzyme solution, or furthermore a purified enzyme may be used. That is, it is possible to use a fraction having the aldolase activity in any form for the method for producing 4R-IHOG of the present invention.

To facilitate the aldol reaction using the aldolase or the composition having the aldolase activity, a reaction mixture containing indole pyruvic acid and pyruvic acid or oxaloacetic acid, and the protein that catalyzes the reaction or an aldolase-containing product may be statically incubated, shaken or stirred at an appropriate temperature of 20 to 50° C. for 30 minutes to 5 days while maintaining the pH at 6 to 12.

Herein, to produce IHOG more stereoselectively, the objective 4R-IHOG may be produced with higher stereoselectivity by suppressing spontaneous aldol condensation. The case where IHOG is produced by aldol condensation of indole-3-pyruvic acid and pyruvic acid is shown as an example (infra). In this reaction, the aldol condensation occurs spontaneously by maintaining an alkali pH, e.g., around pH 9 to 12. IHOG produced by this spontaneous aldol condensation is a mixture of the 4R- and 4S-isomers (racemate), and the stereoselectivity for the position 4 is low. Thus, in one aspect of the present invention, pH upon the reaction of the protein which catalyzes the reaction is controlled to pH 9 to 7, preferably around pH 8.7 to 8 to suppress the spontaneous IHOG production while the aldol condensation is performed selectively for the 4R-IHOG by the aforementioned protein. Consequently, the 4R selectivity of the resulting IHOG may be enhanced. Those skilled in the art may determine such a reaction condition by a simple preliminary examination.

The aldolase disclosed in the present invention belongs to a so-called class II aldolase whose enzyme activity is increased by adding bivalent cation. The bivalent cation added to the reaction system sometimes affects the spontaneous aldol condensation, and thus, sometimes affects the stereoselectivity of the position 4 in the resulting IHOG. Those skilled in the art may determine suitable conditions by simple preliminary examination for the type and the concentration of the bivalent cation added to the reaction system.

The reaction rate may also be enhanced by adding the bivalent cation to the reaction mixture, such as $Mg^{2+}$, $Mn^{2+}$, $Ni^{2+}$, and $Co^{2+}$. In terms of cost, preferably $Mg^{2+}$ is used.

When the bivalent cation is added to the reaction mixture, any salts may be used as long as the salt does not inhibit the reaction, and preferably $MgCl_2$, $MgSO_4$ and $MnSO_4$ are used. Those skilled in the art may determine the concentration of the bivalent cation to be added by the simple preliminary examination. For example, when $Mg^{2+}$ is added, the spontaneous condensation rate of IHOG is suppressed by keeping the concentration of added $Mg^{2+}$ at 1 mM or less, preferably 0.5 mM or less and more preferably 0.1 mM or less. Consequently, the 4R selectivity of IHOG produced via the aldolase may increase.

One example of the preferable reaction condition when the method for producing substituted 4R-IHOG of the present invention is performed is shown below. 4-(Indole-3-ylmethyl)-4-hydroxy-2-oxoglutaric acid (IHOG) is obtained by adding washed microbial cells of aldolase-expressing E. coli as an enzyme source at 10% (w/v) to a reaction mixture composed of 100 mM buffer, 300 mM indole-3-pyruvic acid, 600 mM pyruvic acid, 0.1 mM $MgCl_2$ and 1% (v/v) toluene, and reacting with shaking at 37° C. for 4 hours.

The IHOG produced may be isolated and purified by generally known methods. For example, a method in which IHOG is contacted with an ion exchange resin to absorb basic amino acids, which is then eluted followed by being crystallized. An alternative would be a method in which the eluent is decolorized by filtration through an active charcoal before crystallization is mentioned. The reaction mixture containing the produced IHOG may be used directly for the next step.

In one example, for a production ratio of the 4S-IHOG and the 4R-IHOG when IHOG is produced according to the method of the present invention, it has been confirmed that 4S-IHOG and 4R-IHOG are produced at a ratio of about 4:96 using SpALD in the presence of 0.1 mM $MgCl_2$ at pH of 8.7 to 8.0 adding 300 mM indole-3-pyruvic acid and 600 mM pyruvic acid as substrate (see Example 12). Furthermore, an optical purity of at least 90% at position 4 of 4R-IHOG-oxime may be accomplished by crystallizing the reaction mixture containing the 4R-IHOG obtained in this way after an oximation reaction described later. The measurement of the optical purity is equivalent when measured in any form because the reaction in which IHOG is converted to IHOG-oxime using hydroxylamine has no optical selectivity for the position 4.

4R-IHOG obtained in this manner is highly useful as an intermediate for the production of 4R-monatin.

(2) Protein (Aldolase) Having Aldolase Activity

The protein (sometimes simply referred to as "4R-aldolase") having the 4R-aldolase activity used for the method of the present invention has a characteristic to catalyze the aforementioned reaction. The 4R-aldolase may also be obtained from a microorganism having the 4R-aldolase activity, and the microorganism may be obtained by the following screening method.

(i) Microorganism Having 4R-Aldolase Activity (a) Screening Method for Microorganism Having 4R-Aldolase Activity The microorganism having 4R-aldolase activity may be obtained from the natural environment such as soil and water. That is, it is desirable to add monatin, IHOG, IHOG-oxime, PHG, PHOG or PHOG-oxime, which is the substrate of the objective aldolase, as a carbon source or a nitrogen source, preferably as a sole carbon source or a sole nitrogen source, into the medium, and inoculate a sample as a microorganism source, which is then followed by cultivation. As the additive, a racemic mixture may be used, but preferably the 4R-isomer is used, and more preferably (2R,4R)-monatin is desirable.

Organic nutrients other than the carbon source may be appropriately selected from usual medium ingredients. Examples of the nitrogen source include, an ammonium salt of an organic acid, a nitrate salt, and organic nitrogen compounds such as peptone, yeast extract and meat extract or mixtures thereof. Additionally, nutrients usually used, such as inorganic salts, trace metals and vitamins, may be appropriately mixed. The microorganism capable of growing in such an enriched cultivation environment abundantly contains aldolase active bacteria.

Subsequently, a single colony is obtained from enriched microorganisms in the aforementioned medium, and the colony is regrown on a cultivation plate using the objective substrate as the single carbon source, and the aldolase activity thereof is evaluated. A usual cultivation condition other than the carbon source may be used for the cultivation condition upon the screening. Examples thereof include the conditions described in (c) "Method for culturing microorganism having aldolase activity" (infra).

In a method of evaluating the aldolase activity produced by the microorganism, it is desirable to purify the enzyme from the microbial cells and evaluate an enzymatic reaction using the purified enzyme. Specific examples include i) a method for detecting liberated pyruvic acid from IHOG or PHOG as the substrate (degradation activity detection) and ii) a method for detecting IHOG or PHOG produced by the aldol condensation using indole pyruvic acid or phenyl pyruvic acid and pyruvic acid (or oxaloacetic acid) as the substrates by high performance liquid chromatography (HPLC) measurement (synthetic activity detection). Furthermore, it is desirable to evaluate the 4R selectivity by confirming the molecular asymmetry at position 4 in IHOG or PHOG produced by the aldol condensation in ii) using HPLC.

Specifically, the aldolase activity may be estimated by adding the aldolase to a reaction mixture containing 100 mM buffer, 300 mM indole-3-pyruvic acid, 600 mM pyruvic acid, 0.1 mM MgCl$_2$ and 1% (v/v) toluene, reacting with shaking at 37° C. for 4 hours, and quantifying an amount of produced IHOG by HPLC.

IHOG may be analyzed quantitatively by HPLC equipped with, for example, "Inertsil ODS-2" (5 μm, 4.6×250 mm) supplied from GL Sciences Inc. One example of analysis conditions is shown below.

Mobile phase: 40% (v/v) acetonitrile/5 mM tetrabutylammonium dihydrogen phosphate solution Flow rate: 1 mL/min Column temperature: 40° C.

Detection: UV 210 nm (b) Microorganisms Obtained by Screening

The present inventors have selected microorganisms belonging to genus *Sphingomonas* and microorganisms belonging to genus *Burkholderia* from the enriched microorganisms as a result of their screening, and found that the aldolase usable in the present invention is produced from the microorganisms belonging to both genera and related microorganisms thereof. Therefore, the microorganisms having the aldolase activity usable for the present invention include the microorganisms belonging to genus *Sphingomonas*, genus *Burkholderia* or related genera thereof. Examples of the related genera of *Sphingomonas* may include genera *Rhizomonas*, *Blastomonas*, *Erythromicrobium*, *Porphyrobacter*, *Agrobacterium*, and *Erythrobacter*. Recently, reclassification has been proposed for the genus *Sphingomonas*, and the microorganisms are also sometimes referred to as genera *Sphingobium*, *Novosphingobium* or *Sphingopixis* (International Journal of Systematic and Evolutionary Microbiology (2001), 51, 1405-1417), but the term *Sphingomonas* used herein includes these.

Examples of the microorganisms belonging to genus *Sphingomonas* include *Sphingomonas* sp., *Sphingomonas trueperi*, *Sphingomonas parapaucimobilis*, *Sphingomonas sanguinis*, *Sphingomonas paucimobilis*, *Sphingomonas adhaesiva*, *Sphingomonas pruni*, *Sphingomonas mali*, *Sphingomonas asaccharolytica*, *Sphingomonas echinoids*, *Sphingomonas yanoikuyae*, *Sphingomonas herbicidovorans*, *Sphingomonas chlorophenolica*, *Sphingomonas agrestis*, *Sphingomonas rosa*, *Sphingomonas subarctica*, *Sphingomonas stygia*, *Sphingomonas subterranean*, *Sphingomonas aromaticivorans*, *Sphingomonas capsulate*, *Sphingomonas macrogoltabidus*, *Sphingomonas terrae*, *Rhizomonas suberifaciens*, *Blastomonas natatoria*, *Blastomonas ursincola*, *Agrobacterium sanguineum*, *Erythrobacter longus*, *Erythrobacter litoralis*

Examples of the microorganisms belonging to genus *Burkholderia* include *Burkholderia* sp., *Burkholderia phenazinium*, *Burkholderia caribensis*, *Burkholderia graminis*, *Burkholderia kururiensis*, *Burkholderia brasilensis*, *Burkholderia caryophylli*, *Burkholderia glathei*, *Burkholderia plantarii*, *Burkholderia vandii*, *Burkholderia glumae*, *Burkholderia cocovenenans*, *Burkholderia gladioli*, *Burkholderia vietnamiensis*, *Burkholderia multivorans*, *Burkholderia cepacia*, *Burkholderia pyrrocinia*, *Burkholderia thailandensis*, *Burkholderia pseudomallei*, *Burkholderia mallei*, *Burkholderia andropogonis* (Current Microbiology Vol. 42 (2001), pp. 269-275).

In a particular preferred embodiment of the present invention, the following microorganisms are included. Deposit addresses of these microorganisms are shown below.

*Sphingomonas* sp. AJ110329 strain (C77 strain)
(i) Accession number: FERM BP-10027
(ii) Accepted date of original deposit application: May 21, 2004
(iii) Deposit address: International Patent Organism Depositary, National Institute of Advanced Industrial Science and Technology (Central No. 6, 1-1-1 Higashi, Tsukuba-shi, Ibaraki Prefecture, Japan)

*Sphingomonas* sp. AJ110372 strain (C43 strain)
(i) Accession number: FERM BP-10156
(ii) Accepted date of original deposit application: Oct. 28, 2004
(iii) Deposit address: International Patent Organism Depositary, National Institute of Advanced Industrial Science and Technology (Central No. 6, 1-1-1 Higashi, Tsukuba-shi, Ibaraki Prefecture, Japan)

*Burkholderia* sp. AJ 110371 strain (C24 strain)
(i) Accession number: FERM BP-10155
(ii) Accepted date of original deposit application: Oct. 28, 2004
(iii) Deposit address: International Patent Organism Depositary, National Institute of Advanced Industrial Science and Technology (Central No. 6, 1-1'-1 Higashi, Tsukuba-shi, Ibaraki Prefecture, Japan)

AJ110329 strain (C77 strain, FERM BP-10027) was identified as the aforementioned *Sphingomonas* sp. as a result of the following classification experiments.

A region of about 500 bp at 5' end in 16S ribosomal RNA gene (16S rDNA) was amplified by PCR from genomic DNA of AJ110329 strain, and sequenced (SEQ ID NO:16). Homology of the resulting sequence was determined using MicroSeq Bacterial 500 Library v. 0023 (Applied Biosystems, CA, USA) as the database and using MicroSeq Microbial Identification System Software V. 1.4.1. As a result, there was no known sequence that matched to the nucleotide sequence of 16S rDNA of AJ110329, which exhibited the highest homology of 96.6% to 16S rDNA of *Sphingomonas capsulata*. In a molecular phylogenetic tree, the 16S rDNA of AJ110329 strain was included in a cluster formed by the 16S rDNA of *Sphingomonas*. Its bacteriological characteristics shown in Table 2 are also consistent with the analysis result of the 16S rDNA nucleotide sequence. Accordingly, AJ110329 strain was determined to be *Sphingomonas* sp.

AJ110372 strain (C43 strain, FERM BP-10156) was identified as the aforementioned *Sphingomonas* sp. as a result of the following classification experiment.

A region of about 500 bp at 5' end in 16S ribosomal RNA gene (16S rDNA) was amplified by PCR from genomic DNA of AJ110372 strain, and sequenced (SEQ ID NO:17). Homology of the resulting sequence was determined using MicroSeq Bacterial 500 Library v. 0023 (Applied Biosystems, CA, USA) as the database and using MicroSeq Microbial Identification System Software V. 1.4.1. As a result, there was no known sequence that matched to the nucleotide sequence of 16S rDNA of AJ10372, which exhibited the highest homology of 98.94% to 16S rDNA of *Sphingomonas yanoikuyae*. In a molecular phylogenetic tree, the 16S rDNA of AJ110372 strain was included in a cluster formed by the 16S rDNA of *Sphingomonas*. Accordingly, AJ110372 strain was determined to be *Sphingomonas* sp.

AJ110371 strain (C24 strain, FERM BP-10155) was identified as the aforementioned *Burkholderia* sp. as a result of the following classification experiments.

A region of about 500 bp at 5' end in 16S ribosomal RNA gene (16S rDNA) was amplified by PCR from genomic DNA of AJ110371 strain, and sequenced (SEQ ID NO:18). Homology of the resulting sequence was determined using MicroSeq Bacterial 500 Library v. 0023 (Applied Biosystems, CA, USA) as the database and using MicroSeq Microbial Identification System Software V. 1.4.1. As a result, there was no known sequence that matched to the nucleotide sequence of 16S rDNA of AJ110371 strain, which exhibited the highest homology of 95.21% to 16S rDNA of *Burkholderia phenazinium*. In a molecular phylogenetic tree, the 16S rDNA of AJ110371 strain was included in a cluster formed by the 16S rDNA of *Burkholderia*. Its bacteriological characteristics shown in Table 3 are also consistent with the analysis result of the 16S rDNA nucleotide sequence. Accordingly, AJ110371 strain was determined to be *Burkholderia* sp.

The bacteriological nature of *Sphingomonas* AJ110329 strain (FERM BP-10027) are as described in the following Table 2-1 and Table 2-2.

TABLE 2-1

| 1. MORPHOLOGICAL CHARACTERS | |
|---|---|
| CULTIVATION CONDITION | Nutrient agar (Oxoid, Hampshire, England) 30° C. |
| SIZE OF CELL | (0.8-1.0 × 1.5-3.0 μm) |
| PRESENCE OR ABSENCE OF POLYMORPHISM IN CELLS | − |
| MOTILITY (ADHESION OF FLAGELLA) | − |
| PRESENCE OR ABSENCE OF SPORES(PORTION OF SPORES) | − |
| 2. CULTURAL CHARACTERS | |
| CULTIVATION CONDITION | Nutrient agar medium 30° C. |
| COLOR | Yellow |
| GLOSS | + |

TABLE 2-1-continued

| PIGMENT PRODUCTION | + |
|---|---|
| CULTIVATION CONDITION | Nutrient broth (Oxoid, Hampshire, England) 30° C. |
| PRESENCE OR ABSENCE OF SURFACE GROWTH | − |
| PRESENCE OR ABSENCE OF OPAQUE MEDIUM | + |
| CULTIVATION CONDITION | GELATIN STAB CULTURE 30° C. |
| GROWTH STATE | − |
| GELATIN LIQUEFACTION | − |
| CULTIVATION CONDITION | LITMUS MILK 30° C. |
| COAGULATION | − |
| LIQUEFACTION | − |

TABLE 2-2

| 3. PHYSIOLOGICAL CHARACTERS | | |
|---|---|---|
| GLAM STAINING | | − |
| REDUCTION OF NITRATE | | − |
| NITROGEN REMOVAL REACTION | | − |
| MR TEST | | − |
| VP TEST | | + |
| INDOLE PRODUCTION | | − |
| PRODUCTION OF HYDROGEN SULFIDE | | − |
| HYDROLYSIS OF STARCH | | − |
| UTILIZATION OF CITRIC ACID | (Koser) (Christensen) | − − |
| UTILIZATION OF INORGANIC NITROGEN SOURCE | NITRATE AMMONIUM SALT | + + |
| UREASE ACTIVITY | | − |
| CATALASE | | + |
| OXIDASE | | + |
| GROWTH RANGE; pH | 4 7 8 | − + +w |
| GROWTH RANGE; TEMPERATURE | 20 25 30 37 | + + + − |
| ANAEROBIC GROWTH | | − |
| O—F TEST(OXIDIZATION/ FERMENTATION) | | −/− |
| 4. ACID PRODUCTION/GAS PRODUCTION FROM SUGARS | | |
| L-ARABINOSE | | −/− |
| D-GLUCOSE | | −/− |
| D-FRUCTOSE | | −/− |
| MALTOSE | | −/− |
| LACTOSE | | −/− |
| D-SORBITOL | | −/− |
| INOSITOL | | −/− |
| D-XYLOSE | | −/− |
| D-MANNOSE | | −/− |
| D-GALACTOSE | | +/− |
| SUCROSE | | −/− |
| TREHALOSE | | −/− |
| D-MANNITOL | | −/− |
| GLYCERINE | | −/− |
| 5. OTHER PHYSIOLOGICAL CHARACTERS | | |
| β-GALACTOSIDASE ACTIVITY | | − |
| ARGININE DIHYDRORASE ACTIVITY | | − |
| LYSINE DECARBOXYLASE ACTIVITY | | − |
| TRYPTOPHAN DEAMINASE ACTIVITY | | − |
| GELATINASE ACTIVITY | | − |

The bacteriological nature of *Burkholderia* AJ110371 strain (FERM BP-10155) are as described in the following Table 3-1 and 3-2.

TABLE 3-1

1. MORPHOLOGICAL CHARACTERS

| | |
|---|---|
| CULTIVATION CONDITION | Nutrient agar (Oxoid, Hampshire, England) 30° C. |
| SIZE OF CELL | (0.5-0.6 × 0.8-1.0 μm) |
| PRESENCE OR ABSENCE OF POLYMORPHISM IN CELLS | − |
| MOTILITY (ADHESION OF FLAGELLA) | + (polar flagellum) |
| PRESENCE OR ABSENCE OF SPORES(PORTION OF SPORES) | − |

2. CULTURAL CHARACTERS

| | |
|---|---|
| CULTIVATION CONDITION | Nutrient agar (Oxoid, Hampshire, England) 30° C. |
| COLOR | Cream |
| GLOSS | + |
| PIGMENT PRODUCTION | − |
| CULTIVATION CONDITION | Nutrient broth (Oxoid, Hampshire, England) 30° C. |
| PRESENCE OR ABSENCE OF SURFACE GROWTH | − |
| PRESENCE OR ABSENCE OF OPAQUE MEDIUM | + |
| CULTIVATION CONDITION | GELATIN STAB CULTURE 30° C. |
| GROWTH STATE | − |
| GELATIN LIQUEFACTION | − |
| CULTIVATION CONDITION | LITMUS MILK 30° C. |
| COAGULATION | − |
| LIQUEFACTION | − |

TABLE 3-2

3. PHYSIOLOGICAL CHARACTERS

| | | |
|---|---|---|
| GLAM STAINING | | − |
| REDUCTION OF NITRATE | | − |
| NITROGEN REMOVAL REACTION | | − |
| MR TEST | | − |
| VP TEST | | − |
| INDOLE PRODUCTION | | − |
| PRODUCTION OF HYDROGEN SULFIDE | | − |
| HYDROLYSIS OF STARCH | | − |
| UTILIZATION OF CITRIC ACID | (Koser) | + |
| | (Christensen) | + |
| UTILIZATION OF INORGANIC NITROGEN SOURCE | NITRATE | + |
| | AMMONIUM SALT | + |
| UREASE ACTIVITY | | + |
| CATALASE | | + |
| OXIDASE | | − |
| GROWTH RANGE; pH | 5.0 | + |
| | 7.0 | + |
| | 8.0 | − |
| GROWTH RANGE; TEMPERATURE | 20 | + |
| | 25 | + |
| | 30 | + |
| | 37 | − |
| ANAEROBIC GROWTH | | +w |
| O—F TEST(OXIDIZATION/FERMENTATION) | | −/− |

4. ACID PRODUCTION/GAS PRODUCTION FROM SUGARS

| | |
|---|---|
| L-ARABINOSE | +/− |
| D-GLUCOSE | −/− |
| D-FRUCTOSE | −/− |
| MALTOSE | −/− |
| LACTOSE | −/− |
| D-SORBITOL | −/− |
| INOSITOL | −/− |
| D-XYLOSE | −/− |
| D-MANNOSE | −/− |
| D-GALACTOSE | −/− |
| SUCROSE | −/− |
| TREHALOSE | −/− |
| D-MANNITOL | −/− |
| GLYCERINE | −/− |

5. OTHER PHYSIOLOGICAL CHARACTERS

| | |
|---|---|
| β-GALACTOSIDASE ACTIVITY | + |
| ARGININE DIHYDRORASE ACTIVITY | + |
| LYSINE DECARBOXYLASE ACTIVITY | + |
| TRYPTOPHAN DEAMINASE ACTIVITY | − |
| GELATINASE ACTIVITY | − |

References and kit used:

1) BARROW, (G. I.) and FELTHAM, (R. K. A): Cowan and Steel's Manual for the Identification of Medical Bacteria. $3^{rd}$ edition. 1993, Cambridge University Press.
2) Toshikazu Sakazaki, Etsuro Yoshizaki and Kanji Miki: Shin Saikin Baichigaku Kouza II (2nd edition), 1988, Kindai Shuppan, Tokyo.
3) Kit for bacterial identification: API20, NE (bioMerieux, France: http://www.biomerieux.fr/home_en.htm)

(c) Method for Culturing Microorganism Having Aldolase Activity

A culture method for the microorganism that are a source of aldolase may be a liquid culture or a solid culture, but a method for submerged culture with stirring and aeration is industrially advantageous. As nutrient sources in a nutrient medium, carbon sources, nitrogen sources, inorganic salts and trace nutrient sources usually used for the cultivation of microorganisms may be used. All may be used as long as they may be utilized by the strain employed.

An aerobic condition is employed as an aeration condition. The cultivation temperature may fall into the range where the bacteria grow and the aldolase is produced. Therefore, there is no strict condition, and the temperature is typically 10 to 50° C., preferably 30 to 40° C. The cultivation time varies depending on the other cultivation condition. For example, cultivation may be performed until the aldolase is most abundantly produced, and typically for 5 hours to 7 days, and preferably for about 10 hours to 3 days.

(d) Method for Isolating Aldolase from Microorganism

After the cultivation of the microorganism having the aldolase activity, microbial cells are collected by centrifugation (e.g., 10,000×g, 10 min). Disrupting or lysing the microbial cells, because most aldolase is present in the microbial cells, can be used to solubilize the aldolase. Processes such as ultrasonic disruption, French press disruption or glass beads disruption may be employed to disrupt the microbial cells. Treating with egg white lysozyme or peptidase or an appropriate combination thereof may be used to lyse the microbial cells.

When the aldolase derived from aldolase-producing bacteria is purified, the purification is performed using an enzyme solution as a starting material. If undisrupted or unlysed cell debris is present, it is desirable to remove the precipitated debris by centrifuging the solution again.

The aldolase may be purified by standard method for the usual purification of the enzyme, e.g., ammonium sulfate salting out, gel filtration chromatography, ion exchange chromatography, hydrophobic chromatography, and hydroxyapatite chromatography. As a result, a fraction containing the aldolase with higher specific activity may be obtained.

The amino acid sequence at amino-terminal domain may be determined by applying the purified aldolase preparation to a protein sequencer by an Edman degradation method (Edman, P., Acta Chem. Scand. 4, 227 (1950)). An internal amino acid sequence may be determined by preparing and purifying a peptide preparation by reverse phase HPLC subsequent to peptidase treatment, and applying it to the protein sequencer by the Edman degradation method.

Based on the shown amino acid sequence, a nucleotide sequence of DNA encoding it may be deduced. The nucleotide sequence of the DNA may be deduced by employing universal codons.

Based on the deduced nucleotide sequence, a DNA molecule of about 30 base pairs is synthesized. A method for synthesizing the DNA molecule is disclosed in Tetrahedron Letters, 22:1859 (1981). The DNA molecule may also be synthesized using a synthesizer supplied from Applied Biosystems. The DNA molecule may be utilized as a probe when full length DNA encoding the aldolase is isolated from a chromosomal gene library of the aldolase-producing bacteria. Alternatively, the DNA molecule may be utilized as a primer when the DNA encoding the aldolase of the present invention is amplified by PCR. But, when the DNA amplified by PCR does not contain the full length DNA encoding the aldolase, using the DNA amplified by PCR as a probe, the full length DNA encoding the aldolase is isolated from the chromosomal gene library of the aldolase-producing bacteria.

The PCR procedure is described in White, T. J. et al., Trends Genet., 5:185 (1989). A method for preparing chromosomal DNA, and a method for isolating an objective DNA molecule from a gene library using a DNA molecule as a probe are described in Molecular Cloning, 2nd edition, Cold Spring Harbor press (1989).

A method for determining a nucleotide sequence of the isolated DNA encoding the aldolase is described in A Practical Guide to Molecular Cloning, John Wiley & Sons, Inc. (1985). Alternatively, a DNA sequencer supplied from Applied Biosystems may determine the nucleotide sequence.

A method for producing the DNA encoding the aldolase from the aldolase-producing bacteria also includes a method for obtaining DNA which hybridizes with the full length or a partial sequence of the DNA encoding the aldolase of the present invention as a probe.

To obtain the DNA encoding the aldolase from the aldolase-producing bacteria, a DNA sequence deduced from a highly conservative amino acid sequence region by alignment of the amino acid sequence of the present invention may be utilized as the probe, or the primer of PCR. When the DNA amplified by PCR does not contain the full length DNA encoding the aldolase, using the DNA amplified by PCR as the probe, the full length DNA encoding the aldolase is isolated from the chromosomal gene library of the aldolase-producing microorganisms.

In this manner, the microorganism having the aldolase activity is obtained, and the aldolase and the DNA encoding the aldolase may be obtained from the microorganism.

(ii) Aldolase

The present inventors obtained aldolase from C77 strain (*Sphingomonas* sp. AJ110329 strain) isolated by the aforementioned screening method, and designated it as SpALD. A sequence of DNA encoding the SpALD of the present invention specified by the aforementioned methods is shown in SEQ ID NO:1 (CDS: nucleotide Nos. 210 to 1004), and an amino acid sequence of the SpALD is shown in SEQ ID NO:2.

The present inventors further screened microorganisms (detailed in Examples), obtained novel aldolase genes from C43 strain (*Sphingomonas* sp. AJ110372 strain) and C24 strain (*Burkholderia* sp. AJ110371 strain) (SEQ ID NOS:12 and 14) by Southern analysis and colony hybridization using partial nucleotide sequences in SEQ ID NO:1 as probes, and obtained a protein (SpALD2) having an amino acid sequence of SEQ ID NO:13 and a protein (BuALD) having an amino acid sequence of SEQ ID NO:15. A comparison of the sequences of SpALD, SpALD2 and BuALD is shown in FIG. 1. A core sequence (SEQ ID NO:23) of the aldolase which is common to three aldolases was shown on an upper lane in the figure. The number of amino acid residues common to the three aldolases is 200 which occupies 70.2% in the total residues. The number of amino acid residues common to two of the three aldolases is 76 residues, and occupies 96.8% in conjunction with the core sequence in the total residues. The homology between the SpALD and the SpALD2 is 88.4%, and the homology between the SpALD and the BuALD is 74.7%.

Furthermore, the homology to the other sequences known publicly was surveyed. As a result, the amino acid sequence of SEQ ID NO:2 has 20% homology to 2,4-dihydroxyhept-2-ene-1,7-dioic acid aldolase (HpcH) derived from *Escherichia coli* C strain (Stringfellow J. M. et al., Gene. 1995 166 (1):73-6). The homology to the other known aldolases such as IHOG aldolase (gene name: PtALD) derived from *Pseudomonas taetrolens*, IHOG aldolase (gene name: PcALD) derived from *Pseudomonas coronafaciens* (International Publication Pamphlet No. 03/056026), 4-Hydroxy-4-methyl-2-oxoglutarate aldolase (gene name: proA) derived from *Comamonas testeroni* ATCC 49249 or 4-Hydroxy-4-methyl-2-oxoglutarate aldolase (gene name: proA) derived from *Pseudomonas straminea* is as low as 10% or less with being almost no homology, indicating that the aldolases found in the present invention are quite novel proteins. The three aldolases found by the present inventors also configure a part of the present invention, and are sometimes collectively referred to as the "aldolase of the present invention".

The homology was analyzed using gene analysis software "Genetyx ver. 6" (Genetyx Corporation), and values were calculated using default parameters.

Any of the protein having at least 70% homology, preferably at least 74% homology, still preferably at least 80% homology, still more preferably at least 85% homology and particularly preferably at least 95% homology to the amino acid sequence of SEQ ID NO:2 has the similar enzyme activity and may be used for the present invention. A protein having at least 70% homology to the amino acid sequence of SEQ ID NO:2 and having the core sequence according to SEQ ID NO:23 may be used highly suitably.

Therefore, the protein having the 4R-aldolase activity used in the method of the present invention comprises the aldolase of the present invention, and includes the following proteins (a) and (b):

(a) the protein comprising the amino acid sequence of SEQ ID NO:2, and (b) the protein having at least 70% homology to the amino acid sequence of SEQ ID NO:2 and having the 4R-aldolase activity.

Additionally, the protein (b) comprises the following protein (c):

(c) the protein comprising the amino acid sequence according to any of SEQ ID NO:13 or 15.

The aldolase of the present invention comprises the following proteins:

(d) the protein comprising the amino acid sequence according to any of SEQ ID NO:2, 13 or 15, and
(e) the protein comprising the amino acid sequence containing mutation selected from the group consisting of substitution, deletion, insertion, addition and inversion of one or several amino acid residues in the amino acid sequence according to any of SEQ ID NO:2, 13 or 15.

As used herein, "one or several" are in the range where a three dimensional structure of the protein with amino acid residues and the aldolase activity are not significantly impaired, and specifically from 1 to 90, preferably 1 to 75, more preferably 1 to 57, still more preferably 1 to 43, and particularly preferably 1 to 15 amino acid residues may be altered. But it is desirable that the protein having the amino acid sequence comprising one or several substituted, deleted, inserted, added or inverted amino acid residues in the amino acid sequence according to any of SEQ ID NO:2, 13 or 15 retains not less than 10%, preferably not less than 30%, more preferably not less than 50% and still more preferably not less than 70% of the aldolase activity, preferably the 4R-aldolase activity of the protein having the amino acid sequence according to any of SEQ ID NO:2, 13 or 15 under a condition at 33° C. and pH 9 under a condition at 33° C. and pH 9.

The above substitution, deletion, insertion or addition includes a conservative mutation so that the aldolase activity is retained. The conservative mutation is typically a conservative substitution. Substitution of amino acids regarded as the conservative substitution includes the substitution of Ala with Ser or Thr, the substitution of Arg with Gln, H is or Lys, the substitution of Asn with Glu, Gln, Lys, H is or Asp, the substitution of Asp with Asn, Glu or Gln, the substitution of Cys with Ser or Ala, the substitution of Gln with Asn, Glu, Lys, H is, Asp or Arg, the substitution of Glu with Asn, Gln, Lys or Asp, the substitution of Gly with Pro, the substitution of His with Asn, Lys, Gln, Arg or Tyr, the substitution of Ile with Leu, Met, Val or Phe, the substitution of Leu with Ile, Met, Val or Phe, the substitution of Lys with Asn, Glu, Gln, His or Arg, the substitution of Met with Ile, Leu, Val or Phe, the substitution of Phe with Trp, Tyr, Met, Ile or Leu, the substitution of Ser with Thr or Ala, the substitution of Thr with Ser or Ala, the substitution of Trp with Phe or Tyr, the substitution of Tyr with His, Phe or Trp and the substitution of Val with Met, Ile, or Leu.

The aldolase activity when used in the method of the present invention refers to the 4R-aldolase activity, and the optical selectivity is not strictly required for the aldolase (protein) of the invention, but the 4R-aldolase activity is more preferable. In the following context, the term "aldolase activity" used in the method of the present invention indicates the 4R-aldolase activity, and is the activity that can catalyze the reaction in which 4R-IHOG is preferentially produced by the aldol condensation of indole pyruvic acid and pyruvic acid or oxaloacetic acid as described in the above section (1) Reaction. As used herein, producing "4R-IHOG preferentially" indicates that the optical purity for the R-isomer is greater than that for the S-isomer at position 4 of produced IHOG, and preferably indicates that the R-isomer is efficiently produced at the optical purity of at least 70%, and particularly preferably at least 90%.

Meanwhile, when the "aldolase activity" means the activity of the protein of the present invention, the activity means the aldolase activity that requires no optical selectivity. The aldolase activity that requires no optical activity means the activity that produces IHOG from indole pyruvic acid and pyruvic acid (or oxaloacetic acid), and no optical selectivity is required because the aldolase of the present invention is useful regardless of optical selectivity levels.

Subsequently, enzyme chemical nature of purified SpALD and BuALD will be described below.

The SpALD and the BuALD catalyze a reaction in which 4R-IHOG is preferentially produced by allowing indole pyruvic acid to react with pyruvic acid or oxaloacetic acid.

Optimal pH of the SpALD is around 7.1 to 8.0 at 37° C. The SpALD has pH stability at pH 8 or below, and temperature stability at 50° C. or below and the excellent temperature stability particularly at 30° C. or below.

The molecular weight of the SpALD was about 155 kDa when determined by gel filtration, and was about 30 kDa when determined by SDS-PAGE. Thus, it is estimated that the SpALD has a hexamer structure with subunit of about 30 kDa molecular weight.

Therefore, another aspect of the protein of the present invention is a protein having the following characteristics:

(A) having an activity which catalyzes a reaction in which 4-(indole-3-ylmethyl)-4-hydroxy-2-oxoglutaric acid is produced by the aldol condensation of indole-3-pyruvic acid and pyruvic acid and/or an activity which catalyzes a reaction in which 4-phenylmethyl-4-hydroxy-2-oxoglutaric acid is produced by the aldol condensation of phenyl pyruvic acid and pyruvic acid;
(B) having an optimal pH of about 7.5 to 8.0 at 37° C. for the activity according to (A);
(C) having a pH stability at pH 8 or below;
(D) having a temperature stability at 50° C. or below; and
(E) having a molecular weight of about 155 kDa when determined by the gel filtration and a molecular weight of about 30 kDa per subunit when determined by SDS-PAGE.

The BuALD has an optimal pH of about 6.5 to 7.5 at 37° C., a pH stability at pH 7.5 or below, a temperature stability at 37° C. or below, and particularly, the excellent temperature stability at 30° C. or below.

A molecular weight of the BuALD was about 160 kDa when determined by gel filtration, and was about 30 kDa when determined by SDS-PAGE. Thus, it is estimated that the BuALD has a hexamer structure with subunit of about 30 kDa molecular weight.

Therefore, another aspect of the protein of the present invention is a protein having the following characteristics:

(A) having an activity which catalyzes a reaction in which 4-(indole-3-ylmethyl)-4-hydroxy-2-oxoglutaric acid is produced by the aldol condensation of indole-3-pyruvic acid and pyruvic acid and/or an activity which catalyzes a reaction in which 4-phenylmethyl-4-hydroxy-2-oxoglutaric acid is produced by the aldol condensation of phenyl pyruvic acid and pyruvic acid;
(B) having an optimal pH of about 6.5 to 7.5 at 37° C. for the activity according to (A);
(C) having a pH stability at pH 8.5 or below;
(D) having a temperature stability at 37° C. or below; and
(E) having a molecular weight of about 160 kDa when determined by the gel filtration and a molecular weight of about 30 kDa per subunit when determined by SDS-PAGE.

As used herein, the term "about" includes 20% deviations from the recited value, more preferably 10% deviations from the recited value, still more preferably 5% deviations from the recited value, and most preferably 2.5% deviations from the recited value.

(iii) DNA which Encodes Aldolase

The present inventors have obtained an aldolase gene of the present invention having the nucleotide sequence of SEQ ID NO:1, an aldolase gene of the present invention having the nucleotide sequence of SEQ ID NO:12, and an aldolase gene of the present invention having the nucleotide sequence of SEQ ID NO:14 from *Sphingomonas* sp. AJ11372 strain (C77 strain), *Sphingomonas* sp. AJ110329 strain (C43 strain) and *Burkholderia* sp. AJ110371 strain (C24 strain), respectively. These strains were aldolase-producing bacteria isolated by the present inventors as described in the above (i) and (ii). These genes encode the aldolases of the present invention, which catalyze the reaction in which IHOG is synthesized from indole pyruvic acid and pyruvic acid (or oxaloacetic acid), and make up part of the present invention.

DNA encoding the aldolase are not only the DNA shown in SEQ ID NOS:1, 12 and 14. That is, because the difference of nucleotide sequences should be observed with respect to each species and strain of bacteria belonging to genera *Sphingomonas* and *Burkholderia*, which produce the aldolase which catalyzes the reaction in which IHOG is synthesized from indole pyruvic acid and pyruvic acid (or oxaloacetic acid).

That is, the DNA encodes a protein are at least 70% homologous, preferably at least 74% homologous, more preferably at least 80% homologous, still more preferably at least 85% homologous and particularly preferably at least 95% homologous to the amino acid sequence of SEQ ID NO:2 and having the aldolase activity, preferably the 4R-aldolase activity, or a protein having at least 70% homology to the amino acid sequence of SEQ ID NO:2 and having the core sequence of aldolase of SEQ ID NO:23 and having the aldolase activity, preferably the 4R-aldolase activity is included in the DNA of the present invention.

The DNA of the present invention are not only the DNA encoding the isolated aldolase, and of course, even if the DNA encoding the aldolase isolated from the chromosomal DNA of the aldolase-producing microorganisms is artificially mutated, when the DNA encodes the aldolase, the DNA is the DNA of the present invention. A method for producing an artificial mutation, which is frequently used includes a method for site-directed mutagenesis described in Method in Enzymol, 154 (1987).

A DNA which hybridizes with a DNA comprising a nucleotide sequence complementary to the nucleotide sequence according to SEQ ID NO:1, 12 or 14 under stringent conditions, and encodes the protein having the aldolase activity, preferably the 4R-aldolase activity is also included in the DNA of the invention.

As used herein, the term "stringent conditions" refers to conditions where a so-called specific hybrid is formed whereas no non-specific hybrid is formed. Although it is difficult to clearly quantify this condition, examples thereof may include a condition where a pair of DNA sequences with high homology, e.g., DNA sequences having a homology of at least 50%, more preferably at least 80%, still more preferably at least 90% homology and particularly preferably at least 95% homology are hybridized whereas DNA with lower homology than that are not hybridized, and a washing condition of an ordinary Southern hybridization, i.e., hybridization at salt concentrations equivalent to 0.1×SSC and 0.1% SDS at 37° C., preferably 0.1×SSC and 0.1% SDS at 60° C., and more preferably 0.1×SSC and 0.1 SDS at 65° C.

Herein, the "aldolase activity" or the "4R-aldolase activity" is the same as defined in the above section (ii) Aldolase. But, in the case of the nucleotide sequence which hybridizes with the complementary nucleotide sequence to the nucleotide sequence of SEQ ID NO:1, 12 or 14 under the stringent condition, it is desirable that the protein derived from the sequence retains the aldolase activity, preferably the 4R-aldolase activity at least 10%, preferably at least 30%, more preferably at least 50%, and still more preferably at least 70% of the protein having the amino acid sequence of SEQ ID NO:2, 13 or 15 under the condition at 33° C. at pH 9.

Additionally, a DNA molecule encoding the substantially same protein as the aldolase encoded by the DNA of SEQ ID NO:1, 12 or 14 is also the DNA of the present invention. That is,
  (a) a DNA comprising a nucleotide sequence of nucleotide Nos. 210 to 1004 in the nucleotide sequence of SEQ ID NO: 1,
  (b) a DNA comprising a nucleotide sequence of nucleotide Nos. 399 to 1253 in the nucleotide sequence of SEQ ID NO:12,
  (c) a DNA comprising a nucleotide sequence of nucleotide Nos. 531 to 1385 in the nucleotide sequence of SEQ ID NO:14,
  (d) a DNA which hybridizes with a DNA comprising a nucleotide sequence complementary to the nucleotide sequence of SEQ ID NO:1 or the nucleotide sequence of nucleotide Nos. 210 to 1004 of SEQ ID NO:1, the nucleotide sequence of SEQ ID NO:12 or the nucleotide sequence of nucleotide Nos. 399 to 1253 of SEQ ID NO:12, or the nucleotide sequence of SEQ ID NO:14 or the nucleotide sequence of nucleotide Nos. 531 to 1385 of SEQ ID NO:14, and encodes the protein having aldolase activity,
  (e) a DNA molecule encoding a protein comprising the amino acid sequence of SEQ ID NO:2, 13 or 15,
  (f) a DNA molecule encoding a protein having the amino acid sequence containing mutation selected from the group consisting of substitution, deletion, insertion, addition or inversion of one or several amino acid residues in the amino acid sequence of SEQ ID NO:2, 13 or 15 and having aldolase activity, and
  (g) a DNA molecule encoding a protein composed of the amino acid sequence having at least 70% homology to the amino acid sequence of SEQ ID NO:2, 13 or 15 and having aldolase activity,
are also included in the DNA of the present invention.

Herein, a significance of "one or more" is the same as defined in the above section (ii) Aldolase.

(3) Method for Producing Aldolase

Preferred methods for producing the aldolase will now be described. As the method for producing the aldolase of the present invention, there are two methods, i.e., (i) a method in which the aldolase is produced and accumulated by cultivating the aldolase-producing microorganism, and (ii) a method in which an aldolase-producing transformant is made by recombinant DNA technology and the aldolase is produced and accumulated by culturing the transformant. The method (i) was described as the method for obtaining the aldolase-producing microorganism and the method for cultivating the aldolase-producing microorganism in the above section (2) (i). The method (ii) will be described below.

(ii) Process by Recombinant DNA Technology

Numerous examples have been reported for producing useful proteins, such as enzymes and physiologically active substances, by taking advantage of recombinant DNA technology. By the use of the recombinant DNA technology, it is possible to perform mass production of the useful protein that is naturally present in a trace amount.

FIG. 2 is a flowchart of production steps of the aldolase of the present invention.

First, a DNA molecule encoding the aldolase of the present invention is prepared (Step S1). Then, the prepared DNA molecule is ligated to a vector DNA to make a recombinant DNA (Step S2), and cells are transformed with the recombinant DNA to make transformants (Step S3). Subsequently, the aldolase is produced and accumulated in a medium and/or the cells by cultivating the transformants in the medium (Step S4).

Thereafter, the purified aldolase is produced in Step S5 by recovering and purifying the enzyme.

The objective optically active IHOG may be produced on a large scale by using the purified aldolase produced in Step S5 or the medium and/or the cells in which the aldolase has been accumulated in Step S4 for the aldol reaction (Step S6).

The DNA molecule ligated to the vector DNA may be capable of expressing the aldolase of the present invention.

As an aldolase gene ligated to the vector DNA, any of the DNA molecules described in the above section (2) Aldolase (iii) DNA may be used.

When producing a protein on a large scale using recombinant DNA technology, a preferable mode thereof may include formation of an inclusion body of the protein. The advantages of this expression production method includes protection of the objective protein from digestion by proteases present in the microbial cells, and ready purification of the objective protein that may be performed by disruption of the microbial cells and the following centrifugation.

The protein inclusion body obtained in this manner may be solubilized by a protein denaturing agent, which is then subjected to activation regeneration mainly by eliminating the denaturing agent, thus restoring the correctly refolded and physiologically active protein. There are many examples of such procedures, such as activity regeneration of human interleukin 2 (JP 61-257931 A).

In order to obtain the active protein from the protein inclusion body, a series of the manipulations such as solubilization and activity regeneration is required, and thus the manipulation is more complicate than those in the case of directly producing the active protein. However, when a protein that affects microbial cell growth is produced on a large scale in the microbial cells, effects thereof may be suppressed by accumulating the protein as the inactive inclusion body in the microbial cells.

The methods for producing the objective protein on a large scale as the inclusion body may include methods of expressing the protein alone under control of a strong promoter, as well as methods of expressing the objective protein as a fusion protein with a protein that is known to be expressed in a large amount.

It is effective to arrange a recognition sequence of restriction protease at an appropriate position, for cleaving out the objective protein after the expression of the fusion protein.

When the protein is produced on a large scale using recombinant DNA technology, the host cells to be transformed may include bacterial cells, actinomycetal cells, yeast cells, fungal cells, plant cells or animal cells. The microorganism having a host-vector system may include genus *Escherichia*, genus *Pseudomonas*, genus *Corynebacterium* and genus *Bacillus*, and preferably *Escherichia coli* is used because there are many findings for technology to produce the protein on a large scale using *Escherichia coli*. A method for producing the aldolase using transformed *Escherichia coli* (*E. coli*) will be described below.

As promoters for expressing the DNA encoding, promoters usually used for the production of foreign proteins in *E. coli* may be used, and examples thereof may include strong promoters such as T7 promoter, trp promoter, lac promoter, tac promoter and PL promoter.

In order to produce an aldolase as a fusion protein inclusion body, a gene encoding other protein, preferably a hydrophilic peptide is ligated to an upstream or downstream of the aldolase gene, whereby a fusion protein gene may be produced. Such a gene encoding the other protein may be the one that increases the accumulation amount of the fusion protein and enhances solubility of the fusion protein after steps of modification and regeneration, and example thereof may include T7 gene 10, β-galactosidase gene, dehydrofolate reductase gene, interferon γ gene, interleukin-2 gene, prochymosin gene and the like as candidates.

These genes are ligated to the gene encoding the aldolase so that reading frames of codons are matched. Such a ligation may be performed by ligation at an appropriate restriction enzyme site, or by utilization of synthetic DNA with appropriate sequence.

In order to increase the production amount of the aldolase, it is preferable to ligate a terminator, i.e., a transcription termination sequence to the downstream of the fusion protein gene. This terminator may include T7 terminator, fd phage terminator, T4 terminator, terminator of tetracycline resistant gene, and terminator of *Escherichia coli* trpA gene.

As a vector to introduce the gene encoding the aldolase or the fusion protein of the aldolase and the other protein into *E. coli*, so-called multi-copy types are preferable. Preferable plasmids may include those having a replication origin derived from ColE1, such as pUC type plasmids, pBR322 type plasmids or derivatives thereof. As used herein, the "derivatives" may include those in which modification is given to the plasmids by substitution, deletion, insertion, addition and/or inversion of nucleotides. The modification as referred to herein may also include modification by mutations by mutagens and UV irradiation or spontaneous mutation.

It is preferred that the vector has a marker such as an ampicillin resistant gene for transformant selection. As such a plasmid, an expression vector carrying the strong promoter is commercially available (pUC types (supplied from Takara Shuzo Co., Ltd.), pPROK types (supplied from Clontech), pKK233-2 (supplied from Clontech) and the like).

A recombinant DNA is obtained by ligating a DNA fragment where the promoter, the gene encoding the aldolase gene or the fusion protein of the aldolase and the other protein, and the terminator are sequentially ligated, to the vector DNA.

*E. coli* is transformed using the recombinant DNA and this transformed *E. coli* is cultivated, thereby the aldolase or the fusion protein of the aldolase and the other protein is expressed and produced. For a transformed host, a microorganism usually used for the expression of the foreign gene may be used, and in particular, *E. coli*, JM109 (DE3) and JM109 strains are preferable. Methods for the transformation and for selecting the transformant are described in Molecular Cloning, 2nd edition, Cold Spring Harbor Press (1989).

When expressed as a fusion protein, the aldolase may be cleaved out using a restriction protease recognizing a sequence that is not present in the aldolase. The restriction protease includes blood coagulation factor Xa, kallikrein or the like.

The production media to be used may include the media usually used for cultivating *E. coli*, such as M9-casamino acid medium and LB medium. Culture conditions and production induction conditions may be appropriately selected depending on types of the marker of vector, the promoter of vector, the host microorganism and the like.

The aldolase or the fusion protein of the aldolase and the other protein may be harvested by the following method: when the aldolase or the fusion protein thereof is solubilized in the microbial cells, the microbial cells may be harvested and then disrupted or lysed, to obtain a crude enzyme solution. If necessary, the aldolase or the fusion protein may be further subjected to purification in accordance with ordinary methods such as precipitation, filtration and column chromatography. In this case, the purification may also be performed in accordance with methods utilizing an antibody against the aldolase or the fusion protein.

Where the protein inclusion body is formed, the protein inclusion body may be solubilized with a denaturing agent. The inclusion body may be solubilized together with the microbial cells. However, considering the following purification process, it is preferable to harvest the inclusion body before solubilization. Harvest of the inclusion body from the microbial cells may be performed in accordance with conventionally and publicly known methods. For example, the microbial cells are broken, and the inclusion body is recovered by centrifugation and the like. The denaturing agent that solubilizes the inclusion body of the protein may include guanidine-hydrochloric acid (e.g., 6 M, pH 5 to 8), urea (e.g., 8 M).

As a result of removal of the denaturing agent by dialysis and the like, the protein may be regenerated as having the activity. Dialysis solutions used for the dialysis may include Tris hydrochloric acid buffer, phosphate buffer and the like. The concentration thereof may be 20 mM to 0.5 M, and pH thereof may be 5 to 8.

It is preferred that the protein concentration at a regeneration step is maintained at about 500 µg/ml or less. In order to inhibit self-crosslinking of the regenerated aldolase, it is preferred that dialysis temperature be maintained at 5° C. or below. Methods for removing the denaturing agent may include a dilution method and an ultrafiltration method in addition to this dialysis method. The regeneration of the activity is anticipated by using any of these methods.

When the DNA shown in SEQ ID NO:1, 12 or 14 is used as the DNA encoding the aldolase, the aldolase having the amino acid sequence according to SEQ ID NO:2, 13 or 15 is produced, respectively.

[II] Method for Producing Optically Active Monatin

In a method for producing optically active monatin of the present invention, optically active IHOG is produced by a method described in the section [I] Method for producing optically active IHOG, and subsequently the IHOG is converted to monatin. In IHOG produced in accordance with the method of the present invention, 4R-IHOG is preferentially produced. Therefore, optically active 4R-monatin, i.e., (2R,4R)-monatin and (2S,4R)-monatin are preferentially produced from IHOG produced in the present invention [(2R,4R)-monatin and (2S,4R)-monatin are collectively referred to as 4R-monatin].

In order to efficiently produce (2R,4R)-monatin that is the isomer with highest sweetness in 4 types of the monatin isomers, it is preferable to use 4R-isomer-rich IHOG. In this case, the percentage of 4R-IHOG based on total IHOG is preferably at least 55%, more preferably at least 60%, still more preferably at least 70%, and particularly preferably at least 80%.

A method for converting IHOG into monatin is not particularly limited, and a publicly known method, such as chemical reaction method or enzyme method may be used.

(1) Chemical Reaction Method

The method in which optically active monatin is produced from optically active IHOG by the chemical reaction method may include a method in which optically active IHOG is oximated and corresponding IHOG-oxime described in the following formula (4) or a salt thereof is chemically reduced to produce optically active monatin.

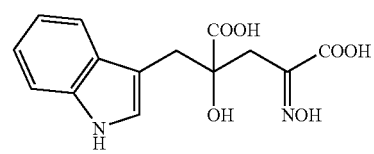

(4)

Preferably, 4R-isomer-rich IHOG is oximated, 4R-IHOG-oxime or the salt thereof is isolated by crystallizing a solution containing the 4R-isomer-rich IHOG, and the 4R-IHOG-oxime or the salt thereof is chemically reduced to produce 4R-monatin.

IHOG is oximated by reacting IHOG under a neutral or alkali condition with an amine compound represented by the following formula (3):

$$H_2N-O-R \qquad (3)$$

wherein R represents a hydrogen atom, an alkyl group, an aryl group or an aralkyl group, or a salt thereof. As used herein, when R is the alkyl, aryl or aralkyl group, R is preferably the alkyl group having 1 to 3 carbon atoms, the aryl or aralkyl group which may have a substituent on a side chain, and R is more preferably selected from methyl, ethyl or benzyl group in terms of crystallization.

This oximation reaction may be performed by directly adding the amine of formula (3) to an aldolase reaction mixture containing IHOG. The 4R-isomer may be isolated by crystallizing 4R-IHOG-oxime or the salt thereof from the solution containing the 4R-isomer-rich IHOG-oxime. A preferable crystallization solvent may include water, an alcohol solvent, or an aqueous alcohol solvent.

4R-monatin may be obtained by reducing 4R-IHOG-oxime or the salt thereof obtained by the crystallization. 4R-IHOG-oxime or the salt thereof is reduced in the presence of hydrogen and a hydrogenated catalyst. As the hydrogenated catalyst, a metal catalyst where a metal catalyst such as platinum, rhodium, palladium, nickel and cobalt is supported on a carrier such as silica, alumina, titania, magnesia, zirconia and active charcoal is preferred.

Conventionally, optically active IHOG could not be efficiently produced. Therefore, in order to isolate 4R-IHOG from the racemate of IHOG (4R,4S-IHOG), it was necessary to oximate 4R,4S-IHOG, subsequently react with chiral amine and crystallize 4R-IHOG-oxime. On the contrary, in accordance with the present invention, 4R-isomer-rich IHOG can be produced at the step of the aldol condensation. Therefore, it is not necessary to optically resolute using the chiral amine before the crystallization, and after the oximation of 4R-isomer-rich IHOG, 4R-IHOG-oxime may be directly crystallized. Thus, it becomes possible to decrease the cost required for the purification of 4R-IHOG.

4R-Monatin obtained by the chemical reduction is a racemic mixture of (2R,4R)-monatin and (2S,4R)-monatin. In order to isolate (2R,4R)-monatin, (2R,4R)-monatin may be crystallized. Specifically, the method described in International Publication Pamphlet WO03/059865 may be used.

(2) Enzymatic Method

When 4R-monatin is produced from 4R-IHOG by an enzymatic method, position 2 of 4R-IHOG may be aminated in the presence of an enzyme which aminates the position 2 of 4R-IHOG. Examples of the enzyme that catalyzes this reaction may include aminotransferase that catalyzes an amino group transfer reaction in 4R-IHOG or dehydrogenase that catalyzes a reductive amination reaction of 4R-IHOG. It is more preferable to use the aminotransferase.

When the aminotransferase is used, 4R-monatin may be produced by reacting 4R-IHOG in the presence of the aminotransferase and an amino group donor. Specifically, the method described in International Publication Pamphlet WO03/056026 may be used.

At that time, it is possible to use either L-aminotransferase or D-aminotransferase. When the L-aminotransferase is used, 2S-monatin may be produced selectively by transferring an amino group of an L-amino acid to position 2 of IHOG. When the D-aminotransferase is used, 2R-monatin may be produced selectively by transferring an amino group of a D-amino acid to position 2 of IHOG. Therefore, to selectively produce (2R,4R)-monatin with high sweetness, it is preferable to react 4R-IHOG with the D-aminotransferase.

The reaction to produce monatin using the aminotransferase may be performed after the aldol condensation and subsequent isolation of produced 4R-IHOG, or may be performed in the same reaction solution by allowing the aldolase and the aminotransferase to coexist. When the reactions are performed in the same reaction solution, a microorganism which co-expresses the DNA encoding the aldolase and the DNA encoding the aminotransferase may be used, or the enzymes may be prepared separately and added into the reaction solution. The microorganism (host cell) that co-expresses the DNA encoding the aldolase and the DNA encoding the aminotransferase may be prepared by co-transfection of the expression vector functionally containing the DNA which encodes the aldolase and the expression vector functionally containing the DNA which encodes the aminotransferase, or the transformation with the expression vector which contains the DNA encoding the aldolase and the DNA encoding the aminotransferase in the form capable of expressing in the host cell with activities.

The above written description of the invention provides a manner and process of making and using it such that any person skilled in this art is enabled to make and use the same, this enablement being provided in particular for the subject matter of the appended claims, which make up a part of the original description.

As used above, the phrases "selected from the group consisting of," "chosen from," and the like include mixtures of the specified materials.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only, and are not intended to be limiting unless otherwise specified.

EXAMPLES

The present invention will be specifically described with reference to the following Examples, but the invention is not limited to these Examples. IHOG, PHOG and (2R,4R)-monatin used in Examples were synthesized by methods according to Reference Examples 1, 2 and 3.

In the present Examples, IHOG and PHOG were quantified by HPLC analysis using "Inertsil ODS-2" (5 µm, 4.6×250 mm) supplied from GL Sciences Inc. The analysis conditions were as follows.

Mobile phase: 40% (v/v) acetonitrile/5 mM tetrabutylammonium dihydrogen phosphate solution
Flow rate: 1 mL/min
Column temperature: 40° C.
Detection: UV 210 nm Asymmetry of produced IHOG or PHOG was analyzed by the HPLC analysis where "Inertsil ODS-2" (5 µm, 4.6×160 mm) supplied from GL Sciences Inc was directly connected with "SUMICHIRAL OA-7100" (5 µm, 4.6×250 mm) supplied from Sumika Chemical Analysis Service Ltd in this order. The analysis condition is as follows.

Mobile phase A: 5% (v/v) acetonitrile, 20 mM potassium phosphate buffer (pH 6.8)
Mobile phase B: 50% (v/v) acetonitrile, 20 mM potassium phosphate buffer (pH 6.8)
Eluted with the mobile phase A from 0 to 90 min, and from 90 to 120 min and washed with the mobile phase B.
Flow rate: 0.4 mL/min
Column temperature: 17° C.
Detection: UV 210 nm Example 1

Screening of Bacteria Having IHOG Aldolase Activity from the Natural World

A bacterial strain having an aldolase activity with optical selectivity for 4R-IHOG was isolated and obtained from its native environment by performing an enrichment cultivation using a medium in which (2R,4R)-monatin (RR-monatin) was a single carbon source.

A soil sample was inoculated into a test tube containing 1 mL of the medium using RR-monatin as the single carbon source (0.4 g/L of RR-monatin monopotassium salt, 0.67 g/L of Yeast Nitrogen base without amino acid (supplied from Difco)), and shaking culture was conducted at 37° C. for 7 days. Again, 0.1 mL of the obtained culture broth was inoculated into the test tube containing 1 mL of the medium using RR-monatin as the single carbon source, and the shaking culture was conducted again at 37° C. for 7 days. The obtained culture broth was appropriately diluted with sterile saline, subsequently applied on a CM2G flat medium (5 g/L of glucose, 10 g/L of yeast extract, 10 g/L of peptone, 5 g/L of NaCl, 20 g/L of agar powder, pH 7.0), and cultivated at 30° C. for 24 hours to isolate a colony.

A strain having the aldolase activity was selected from accumulated microbial strains. The obtained microorganisms were inoculated on a bouillon agar plate (supplied from Eiken Chemical Co., Ltd.), and cultivated at 30° C. for 24 hours. This was inoculated in a plate containing an enzyme-producing medium (5 g/L of glycerol, 5 g/L of fumaric acid, 3 g/L of yeast extract, 2 g/L of peptone, 3 g/L of ammonium sulfate, 3 g/L of $K_2HPO_4$, 1 g/L of $KH_2PO_4$, 0.5 g/L of $MaSO_4 7H_2O$, 2.5 g/L of sodium phthalate, 20 g/L of agar powder, pH 6.5), and cultivated at 30° C. for 24 hours. Obtained microbial cells were inoculated into a reaction mixture composed of 100 mM Tris-HCl (pH 8.0), 50 mM PHOG, 1 mM $MgCl_2$, 5 mM potassium phosphate solution (KPi) and 1% (v/v) toluene. The inoculated concentration of cells was about 1% by wet microbial cell weight. The mixture was reacted at 30° C. for 24 hours. A concentration of free pyruvic acid in the reaction mixture was quantitatively determined by an enzyme method using lactate dehydrogenase (LDH). 10 μL of the reaction mixture was added to 200 μL of a solution composed of 100 mM Tris-HCl (pH 8.0), 1.5 mM NADH, 5 mM $MgCl_2$ and 25 U/mL LDH. The mixed solution was incubated at 30° C. for 10 min. An absorbance at 340 nm was measured after the reaction, and an amount of pyruvic acid in the sample was quantitatively determined with a decreased amount of NADH.

The amount of produced phenyl pyruvic acid was quantitatively determined by the HPLC analysis using "Inertsil ODS-2" (5 μm, 4.6×250 mm) supplied from GL Sciences Inc. The analysis conditions were as follows.

Mobile phase: 20% (v/v) acetonitrile/aqueous solution of 0.05% (v/v) trifluoroacetic acid Flow rate: 1 mL/min Column temperature: 40° C.

Detection: UV 210 nm

Under the present condition, PHOG and phenyl pyruvic acid were eluted at a retention time of about 9.8 min and about 12 min, respectively, and could be identified and quantitatively determined.

The amount produced by the aldolase was calculated by subtracting the amount in a control without the microbial cells from the amount of pyruvic acid or phenyl pyruvic acid produced from PHOG with microbial cells. As a result, bacterial strains were found to have the aldolase activity whose substrate was PHOG.

Subsequently, IHOG was synthesized using the harvested microbial cells having the aldolase activity. The microbial cells were inoculated to the test tube containing 3 mL of the enzyme-producing medium (5 g/L of glycerol, 5 g/L of fumaric acid, 3 g/L of yeast extract, 2 g/L of peptone, 3 g/L of ammonium sulfate, 3 g/L of $K_2HPO_4$, 1 g/L of $KH_2PO_4$, 0.5 g/L of $MaSO_4 7H_2O$, 2.5 g/L of sodium phthalate, pH 6.5). The medium was cultivated at 30° C. for 16 hours. The obtained microbial cells were suspended at 1% (w/v) by wet weight of the microbial cells into the following IHOG synthetic reaction mixture.

IHOG synthetic reaction mixture: 100 mM Hepes-KOH (pH 8.5), 300 mM indole pyruvic acid, 750 mM pyruvic acid sodium salt, 1 mM $MgCl_2$, 5 mM potassium phosphate buffer (pH 8.5).

The reaction mixture was incubated at 37° C. for 16 hours, subsequently produced IHOG was quantitatively determined, and the chirality at position 4 of the reaction product was analyzed. As a result, an aldol condensation activity that produced 4R-IHOG preferentially was found in a selected bacterial strain C77 as shown in Table 4.

TABLE 4

IHOG synthetic reaction by microbial cell reaction of C77 strain

| | 4R-IHOG (mM) | 4S-IHOG (mM) | 4R e.e. (%) |
|---|---|---|---|
| C77 Strain | 32.5 | 22.1 | 19 |
| No Microbial Cell | 15.6 | 15.6 | 0 |

Example 2

Purification of IHOG Aldolase (SpALD) Derived from C77 Strain (*Sphingomonas* sp. AJ110329 Strain)

The IHOG aldolase was purified from a soluble fraction of C77 strain (*Sphingomonas* sp. AJ110329 strain) as follows. As the aldolase activity, an aldol degradation activity was detected using PHOG as the substrate under the following conditions.

Reaction conditions: 50 mM Hepes-KOH (pH 8.5), 2 mM PHOG, 0.25 mM NADH, 0.2 mM KPi, 1 mM $MgCl_2$, 16 U/mL lactate dehydrogenase, 3 μL of enzyme per 600 μL of reaction mixture, 30° C., an absorbance at 340 nm was measured.

(1) Preparation of Soluble Fraction

One platinum loop of the microbial cells of C77 strain (*Sphingomonas* sp. AJ110329 strain) obtained by cultivation in the bouillon agar plate at 30° C. for 24 hours was inoculated to a 500 mL flask containing 50 mL of the enzyme-producing medium (5 g/L of glycerol, 5 g/L of fumaric acid, 5 g/L of ammonium sulfate, 3 g/L of $K_2HPO_4$, 1 g/L of $KH_2PO_4$, 0.5 g/L of $MaSO_4 7H_2O$, 3 g/L of yeast extract, 2 g/L of peptone, 2.5 g/L of sodium phthalate (supplied from Sigma), adjusted to pH 6.5 with KOH), and the shaking culture was conducted at 30° C. for 24 hours. Subsequently, 0.5 mL of the culture broth was inoculated to 20 of 500 mL flasks containing 50 mL of the enzyme-producing medium, and the shaking culture was conducted at 30° C. for 24 hours. The microbial cells were harvested from the obtained culture broth by centrifugation. The collected microbial cells were suspended in and washed with buffer A (20 mM Hepes-KOH, pH 7.6). The microbial cells were then collected again by the centrifugation. The obtained washed microbial cells were suspended in 80 mL of the buffer A, and disrupted by ultrasonic at 4° C. for 30 min. Microbial cell debris was removed by centrifugation for a disruption suspension (×8000 rpm 10 min, twice) to yield a supernatant as a soluble fraction.

(2) Anion Exchange Chromatography: Q-Sepharose FF

The soluble fraction (40 mL) was applied on an anion exchange column Q-Sepharose FF 26/10 (supplied from Pharmacia, CV=20 mL) equilibrated with the buffer A to absorb to a carrier. Proteins which had not been absorbed to the carrier (unabsorbed proteins) were washed out using the buffer A. Subsequently, an absorbed protein was eluted with linear gradient of a KCl concentration from 0 M to 0.7 M (total 140 mL). A PHOG aldolase activity was measured for each eluted fraction, and consequently a peak of the PHOG aldolase activity was detected in the fraction corresponding to about 0.4 M. The same chromatographic procedure was repeated twice.

(3) Hydrophobic Chromatography: Phenyl Sepharose HP HR 16/10

A solution in which the aldolase activity had been detected was dialyzed against buffer B (20 mM Hepes-KOH, 1 M ammonium sulfate, pH 7.6) at 4° C. overnight, and filtered through a filter with a pore size of 0.45 μm. The obtained filtrate was applied on a hydrophobic chromatography column, Phenyl Sepharose HP HR 16/10 (supplied from Pharmacia) pre-equilibrated with the buffer B. This procedure allowed the aldolase to absorb to the carrier.

Unabsorbed proteins to the carrier were washed out using the buffer B, and then the aldolase was eluted with linear gradient of the concentration of ammonium sulfate from 1 M to 0 M. The aldolase activity was measured for each eluted fraction, and the aldolase activity was detected in eluted positions where the concentration of ammonium sulfate was about 0.4 to 0.5M.

(4) Gel Filtration Chromatography: Sephadex 200 HP 16/60

Fractions containing the aldolase were collected, dialyzed against the buffer A, and filtered through the filter with a pore size of 45 μm. The obtained filtrate was concentrated using an ultrafiltration membrane, centriprep 10. The obtained concentrated solution was applied on a gel filtration Sephadex 200 HP 16/60 (supplied from Pharmacia) pre-equilibrated with buffer C (20 mM Hepes-KOH, 0.1 M KCl, pH 7.6), and eluted at a flow rate of 1 mL/min. This procedure allowed the aldolase to be eluted in fractions of about 66 mL. A molecular weight of the aldolase was estimated to be about 155 kDa by the eluted position of the activity peak.

(5) Anion Exchange Chromatography: Mono Q HR 5/5

The obtained fraction was filtered through the filter with a pore size of 0.45 μm. The obtained filtrate was applied on an anion exchange chromatography column Mono-Q HR 5/5 (supplied from Pharmacia) pre-equilibrated with the buffer A. This manipulation allowed the aldolase to absorb to the carrier. Unabsorbed proteins were washed out with the buffer A, and subsequently the protein was eluted with linear gradient of the concentration of KCl from 0 mM to 700 mM (total 24 mL). The aldolase activity was measured for each fraction, and the aldolase activity was detected in the eluted positions where the concentration of KCl was about 0.4 M.

The obtained fractions were subjected to SDS-PAGE, and consequently about 10 bands were observed in an active fraction. Among them, the band of about 30 kDa where an activity profile corresponded to a band intensity profile of SDS-PAGE was present, the band was cut out from SDS-PAGE as a candidate of the aldolase, and was subjected to amino acid sequence.

TABLE 5

Partial purification of IHOG aldolase from C77 strain (*Sphingomonas* sp. AJ110329 strain)

|  | protein (mg) | activity (U) | specific activity (U/mg) | purification (fold) | yield (%) |
|---|---|---|---|---|---|
| crude | 964 | 78.7 | 0.082 | 1 | 100 |
| Q-Sepharose HP 26/10 | 58 | 39.9 | 0.69 | 8 | 51 |
| Phenyl sepharose HP 16/10 | 1.3 | 13.1 | 9.8 | 119 | 17 |
| Sephadex 200 HP 16/60 | 0.28 | 6.9 | 24.7 | 302 | 9 |
| monoQ HR 5/5 | 0.10 | 3.7 | 39.1 | 477 | 5 |

Example 3

Determination of Internal Amino Acid Sequence of IHOG Aldolase

The purified fraction containing aldolase was subjected to SDS-PAGE, then the band corresponding to 30 kDa was cut out, and a sample in SDS-PAGE gel was treated with trypsin (pH 8.5, 35° C., 20 hours) and subjected to a reverse phase HPLC to separate fragmented peptides. Among fractionated fractions, two fractions were analyzed, and 17 and 12 residues of amino acid sequences (SEQ ID NOS:3 and 4) were determined as shown in the following Table 6.

TABLE 6

| Determined internal amino acid sequences | |
|---|---|
| SEQ ID NO. 3 | GVYGV I TPHV STVEQ AY |
| SEQ ID NO. 4 | YWGLS QPEYY AK |

Example 4

Cloning of IHOG Aldolase Gene Derived from C77 Strain (*Sphingomonas* sp. AJ110329 Strain)

(1) Preparation of Chromosomal DNA

C77 strain (*Sphingomonas* sp. AJ110329 strain) was cultivated using 50 mL of CM2G medium at 30° C. overnight (pre-cultivation). A main cultivation was performed using 5 mL of this culture as an inoculum and using 50 mL of the medium. After cultivation until a late logarithmic growth phase, 50 mL of the culture was subjected to the centrifugation (12000×g, 4° C., 15 min) to harvest cells. Using these microbial cells, chromosomal DNA was prepared in accordance with standard methods.

(2) Acquisition of Internal Sequence by PCR

Based on the determined internal amino acid sequences of the IHOG aldolase, mix primers (SEQ ID NO:5 and 6) described in Table 7 were synthesized.

TABLE 7

| Mix primers designed from internal amino acid sequences and synthesized | |
|---|---|
| SEQ ID NO. 5 | ATY CAN CCN CAY GTN WSB CAN GTN GAR CAR GC |
| SEQ ID NO. 6 | GCR TAR TAY TCN GGY TGV SWV ARN CCC C |

Using the mix primers made above, amplification by PCR was performed using the chromosomal DNA of C77 strain (*Sphingomonas* sp. AJ110329 strain) as a template. A PCR reaction was performed using PCR Thermal PERSONEL (supplied from TaKaRa Holdings Inc.) by 30 cycles of the following conditions.

| 94° C. | 30 seconds |
|---|---|
| 55° C. | 30 seconds |
| 72° C. | 1 minute |

A PCR product was subjected to agarose gel electrophoresis, and the amplification of an about 200 bp fragment was observed. The DNA fragment was cloned in pT7Blue (supplied from Novagen), and a nucleotide sequence was determined. Consequently, an amino acid sequence deduced from the obtained DNA fragment corresponded to the internal amino acid sequence of the IHOG aldolase. Thus, it was confirmed that the objective aldolase gene had been obtained.

(3) Acquisition of Full-Length Gene by Colony Hybridization

Using the DNA fragment amplified by PCR, the full-length gene was obtained by Southern analysis and colony hybridization. A DNA probe was prepared using DIGHigh Prime (supplied from Roche Diagnostics), and labeled by overnight incubation at 37° C. in accordance with instructions. The Southern analysis was performed by completely digesting 1 μg of the chromosomal DNA with various restriction enzymes, electrophoresing on 0.8% agarose gel, blotting onto a nylon membrane, and then followed by the steps in accordance with a manual.

Hybridization was performed using DIG Easy Hyb (supplied from Roche Diagnostics), prehybridization was performed at 50° C. for one hour, and subsequently the probe was added to perform the overnight hybridization. Bands were detected using DIG Nucleotide Detection Kit. As a result, a PstI/BamHI fragment of about 3.2 kbp that had strongly hybridized with the probe of the PCR fragment was detected. Subsequently, this PstI/BamHI fragment was obtained by the colony hybridization.

The chromosomal DNA (20 μg) was treated with PstI/BamHI, and subjected to the agarose gel electrophoresis to obtain a fragment of about 3.2 kbp. This was ligated to pUC19, and the library was made in *E. coli* JM109. Colonies were transferred onto a nylon membrane filter (Hybond-N, supplied from Amersham), and alkali modification, neutralization and fixation were given thereto. The hybridization was performed using DIG Easy Hyb. The filter was immersed in the buffer, and prehybridized at 42° C. for one hour. Subsequently, the labeled probe was added for hybridization at 42° C. for 16 hours. After washing with SSC, the colony that had hybridized with the probe was detected using DIG Nucleotide Detection Kit (supplied from Roche Diagnostics). As a result, the clone that had strongly hybridized with the probe was obtained.

The nucleotide sequence of the plasmid DNA of the obtained clone was determined, and consequently it was demonstrated that the plasmid DNA had the nucleotide sequence of SEQ ID NO:1. ORF of 855 bp including the nucleotide sequences corresponding to the determined internal amino acid sequences was found (Nos. 519 to 569 and 666 to 701 in SEQ ID NO:1), and thus the full-length of the objective aldolase was obtained.

Example 5

Large-Scale Expression of IHOG Aldolase (SpALD) in *E. coli*

(1) Construction of Plasmid pTrp4 Containing trp Promoter and rrnB Terminator

A promoter region of trp operon on chromosomal DNA of *E. coli* W3110 was amplified by PCR using oligonucleotides shown in Table 8 (combination of SEQ ID NOS:7 and 8) as primers, and the obtained DNA fragment was ligated to pGEM-Teasy vector (supplied from Promega). *E. coli* JM109 was transformed with a solution containing this ligation product, and strains having the objective plasmid in which a trp promoter had been inserted in an opposite direction to that of a lac promoter were selected among ampicillin resistant strains. Subsequently, a DNA fragment containing the trp promoter obtained by treating this plasmid with EcoO109i/EcoRI was ligated to pUC19 (supplied from Takara) that had been treated with EcoO109i/EcoRI. *E. coli* JM109 was transformed with a solution containing this ligation product, and a strain having the objective plasmid was selected among ampicillin resistant strains. The plasmid was designated as pTrp 1.

Subsequently, pKK223-3 (supplied from Amersham Pharmacia) was treated with HindIII/HincII, and the DNA fragment obtained thereby containing an rrnB terminator was ligated to pTrp 1 that had been treated with HindIII/HincII. *E. coli* JM109 was transformed with a solution containing this ligation product, and a strain having the objective plasmid was selected among ampicillin resistant strains. The plasmid was designated as pTrp2.

Subsequently, the trp promoter region was amplified by PCR with pTrp2 as a template and oligonucleotides shown in Table 8 (combination of SEQ ID NOS 7 and 9) as the primers. This DNA fragment was treated with EcoO109i/NdeI, and ligated to pTrp2 that had been treated with EcoO109i/NdeI. *E. coli* JM109 was transformed with a solution containing this ligation product, and a strain having the objective plasmid was selected among ampicillin resistant strains. The plasmid was designated as pTrp4.

TABLE 8

| Primer sequences | |
|---|---|
| (1) 5' GTATCACG<u>AGGCCCT</u>AGCTGTGGTGTCATGGTGGGTGATC<br>    EcoO109I | SEQ ID NO. 7 |
| (2) 3' TTCGGGGATTC<u>CATATG</u>ATACCCTTTTTAGGTGAACTTGC<br>    NdeI | SEQ ID NO. 8 |
| (3) 3' GGGGGGGG<u>CATATG</u>GGACCTCCTTATTACGTGAACTTG<br>    NdeI | SEQ ID NO. 9 |

(2) Construction of Aldolase Gene-Expressing Plasmid ptrpSpALD and Expression Thereof in *E. coli*

A fragment obtained by amplifying from the chromosomal DNA of C77 strain (*Sphingomonas* sp. AJ110329 strain) using primers (SEQ ID NOS:10 and 11)) shown in Table 9 was digested with NdeI/PstI, and inserted into NdeI/PstI site of pTrp4 to construct a plasmid ptrpSpALD. This plasmid expresses the aldolase gene composed of the amino acid sequence of SEQ ID NO:2 obtained by translating from ATG at 210th as a translation initiation codon to 1004th in the nucleotide sequence of SEQ ID NO:1.

TABLE 9

| Primer sequences for construction of ptrpSpALD | |
|---|---|
| C77ALD Nde 5' (SEQ ID NO. 10): | GGC CAT ATG AGC CAG<br>ACG GGC CTC AAC GGC<br>ATC ATC C |

TABLE 9-continued

Primer sequences for construction of ptrpSpALD

C77ALD Pst 3' (SEQ ID NO. 11):  GCG CTG CAG TCA GTA
                                CCC CGC CAG TTC GCG
                                GCC CTG ACC

25 E. coli JM109 was transformed with the constructed expression plasmid, and one platinum loop of the resulting transformant was inoculated to 50 mL of LB medium containing 100 µg/mL ampicillin and shaken at 37° C. for 16 hours. After the cultivation, microbial cells were collected from 1 mL of the resulting culture, washed, and suspended in 1 mL of 20 mM Hepes-KOH (pH 7.6), and then microbial cells were disrupted ultrasonically. A supernatant was obtained by centrifuging a disruption suspension at 15000 rpm for 10 min to use as a crude enzyme solution.

The aldolase activity was measured using the crude enzyme solution. The aldolase activity was measured by measuring an aldole cleavage activity using PHOG as the substrate under the following conditions.

Reaction conditions: 50 mM Hepes-KOH (pH 8.5), 2 mM PHOG, 0.25 mM NADH, 0.2 mM KPi, 1 mM $MgCl_2$, 16 U/mL lactate dehydrogenase, 3 µL of enzyme per 600 µL of reaction mixture, 30° C., an absorbance at 340 nm was measured.

As a result of measuring, no aldolase activity was detected in E. coli (control) transformed with pTrp4 whereas 33.6 U/mg protein of the aldolase activity was detected in the strain transformed with ptrpSpALD. This confirmed that the objective aldolase gene was certainly cloned and that the plasmid containing SpALD was constructed with high expression.

Example 6

Purification of Recombinant Aldolase Enzyme Derived from C77 Strain (Sphingomonas sp. AJ110329 Strain)

Recombinant SpALD was purified from a soluble fraction of E. coli which had resulted in high expression of the aldolase (SpALD) derived from C77 strain (Sphingomonas sp. AJ110329 strain) as follows. The aldolase activity was measured as the aldole cleavage activity using PHOG as the substrate under the following conditions.

Reaction conditions: 50 mM Hepes-KOH (pH 8.5), 2 mM PHOG, 0.25 mM NAD, 1 mM $MgCl_2$, 16 U/mL lactate dehydrogenase, 3 µL of enzyme per 600 µL of reaction mixture, 30° C., an absorbance at 340 nm was measured.

(1) Preparation of Soluble Fraction

One platinum loop of microbial cells of E. coli/ptrpSpALD cultivated in LB-amp agar plate at 37° C. for 16 hours was inoculated 10 of 500 mL flasks containing 50 mL of the LB-amp medium. Then, the shaking culture was conducted at 37° C. for 16 hours. Microbial cells were harvested from the obtained culture by the centrifugation, suspended in and washed with the buffer A (20 mM Hepes-KOH, pH 7.6), and subsequently centrifuged again to collect the bacterial cells. The obtained washed microbial cells were suspended in 20 mL of the buffer A, and disrupted ultrasonically at 4° C. for 30 min. Microbial cell debris was removed by centrifuging a disruption suspension (×8000 rpm, 10 min, twice), and the resulting supernatant was used as a crude extraction fraction.

(2) Anion Exchange Chromatography: Q-Sepharose FF

The crude extraction fraction (20 mL) obtained above was applied on an anion exchange chromatography column Q-Sepharose FF 26/10 (supplied from Pharmacia, CV=20 mL) pre-equilibrated with the buffer A to absorb to the carrier. Proteins that had not been absorbed to the carrier (unabsorbed proteins) were washed out using the buffer A. Subsequently, an absorbed protein was eluted with a linear gradient of a KCl concentration from 0 M to 0.7 M (total 140 mL). A PHOG aldolase activity was measured for each eluted fraction, and consequently a peak of the PHOG aldolase activity was detected in the fraction corresponding to about 0.4 M.

(3) Hydrophobic Chromatography: Phenyl Sepharose HP HR 16/10

A solution in which the aldolase activity had been detected was dialyzed against buffer B (20 mM Hepes-KOH, 1 M ammonium sulfate, pH 7.6) at 4° C. overnight, and filtered through a filter with a pore size of 0.45 µm. The obtained filtrate was applied on a hydrophobic chromatography column, Phenyl Sepharose HP HR 16/10 (supplied from Pharmacia) pre-equilibrated with the buffer B. This procedure allowed the aldolase to absorb to the carrier.

Unabsorbed proteins onto the carrier were washed out using the buffer B, and then the aldolase was eluted with a linear gradient of the concentration of ammonium sulfate from 1 M to 0 M. The aldolase activity was measured for each eluted fraction, and the aldolase activity was detected in eluted positions where the concentration of ammonium sulfate was about 0.4 to 0.5 M.

(4) Gel Filtration Chromatography: Sephadex 200 HP 16/60

Fractions containing the aldolase were gathered, dialyzed against the buffer A, and filtered through the filter with a pore size of 45 µm. The obtained filtrate was concentrated using an ultrafiltration membrane, centriprep 10. The obtained concentrated solution was applied on a gel filtration Sephadex 200 HP 16/60 (supplied from Pharmacia) pre-equilibrated with buffer C (20 mM Hepes-KOH, 0.1 M KCl, pH 7.6), and eluted at a flow rate of 1 mL/min. This procedure allowed the aldolase to be eluted in fractions of about 66 mL.

(5) Anion Exchange Chromatography: Mono Q HR 5/5

The obtained fraction was filtered through the filter with a pore size of 0.45 µm. The obtained filtrate was applied on an anion exchange chromatography column Mono-Q HR 5/5 (supplied from Pharmacia) pre-equilibrated with the buffer A. This procedure allowed the aldolase to absorb to the carrier. Unabsorbed proteins were washed out with the buffer A, and subsequently the protein was eluted with a linear gradient of the concentration of KCl from 0 mM to 700 mM (total 24 mL). The aldolase activity was measured for each fraction, and the aldolase activity was detected in the eluted positions where the concentration of KCl was about 0.4 M.

The fractions purified by the above column chromatography were subjected to SDS-PAGE, and then a single band at a position corresponding to about 30 kDa was detected by CBB staining. The obtained solution of the recombinant SpALD was dialyzed against the buffer A at 4° C. overnight. This procedure allowed to obtain 1.5 mL of the solution containing 452 U/mL of SpALD.

Example 7

Synthesis of 4-(indole-3-ylmethyl)-4-hydroxy-2-oxoglutaric acid (IHOG) from indole-3-pyruvic acid and pyruvic acid using SpALD 4-(Indole-3-ylmethyl)-4-hydroxy-2-oxoglutaric acid (IHOG) was synthesized from indole-3-pyruvic acid and pyruvic acid using SpALD prepared in Example 6 as an enzyme source. A reaction mixture composed of 100 mM Hepes-KOH (pH 8.5), 300 mM indole-3-pyruvic acid, 750 mM pyruvic acid and 1 mM $MgCl_2$ was reacted at 37° C. for 3 min by adding 7.9 mg/mL SpALD. An enzyme reaction mixture was appropriately diluted and subjected to HPLC analysis to quantitatively determine the produced IHOG. As a result, IHOG production by the aldolase was confirmed. An initial synthetic activity of IHOG under the condition was estimated to be 451 U/mg.

Example 8

Enzymological Characters of SpALD

The following was investigated using the SpALD prepared in Example 6.

Primary measurement condition: 50 mM Hepes-KOH (pH 8.5), 2 mM PHOG, 5 mM $MgCl_2$, 16 U/mL lactate dehydrogenase, the decreased of the absorbance at 340 nm was measured at 30° C.

(1) Kinetics Constant Using PHOG as Substrate

Figure 3A:
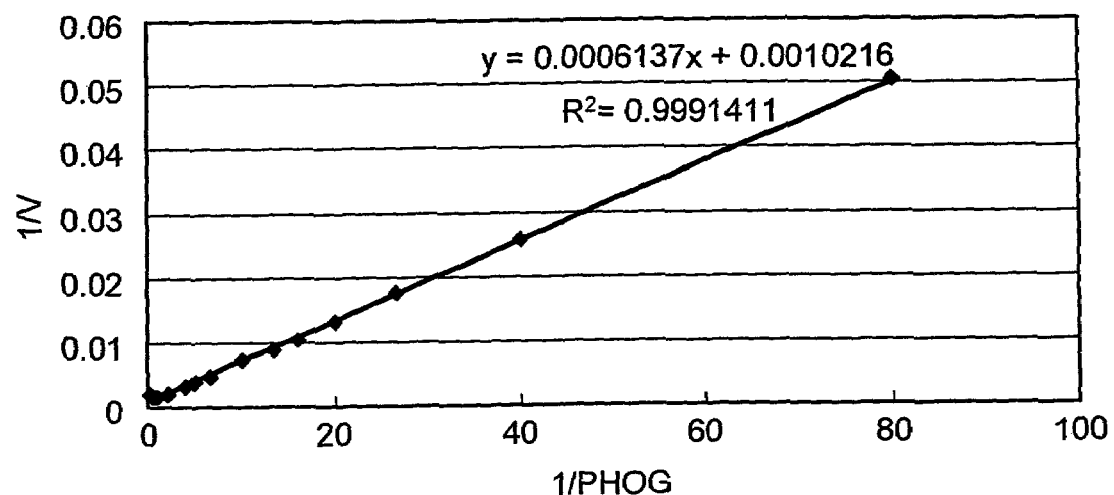
FIG. 3A presents a graph showing reaction rates of SpALD using PHOG as a substrate.
Figure 3B:
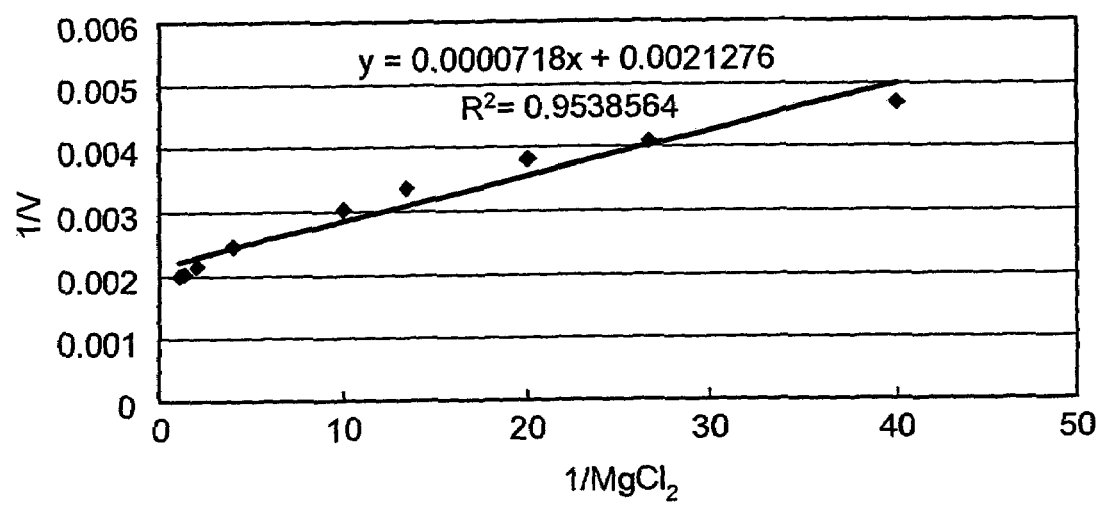
FIG. 3B presents a graph showing reaction rates of SpALD versus MgCl$_2$ concentrations.

From the results shown in FIG. 3, the followings were determined: Vmax (for PHOG)=979 μmol/min/mg, Km (for PHOG)=0.06 mM, Km (for $MgCl_2$)=0.034 mM. No increase of the aldolase activity by the addition of KPB solution was observed.

(2) pH Stability

Figure 4:
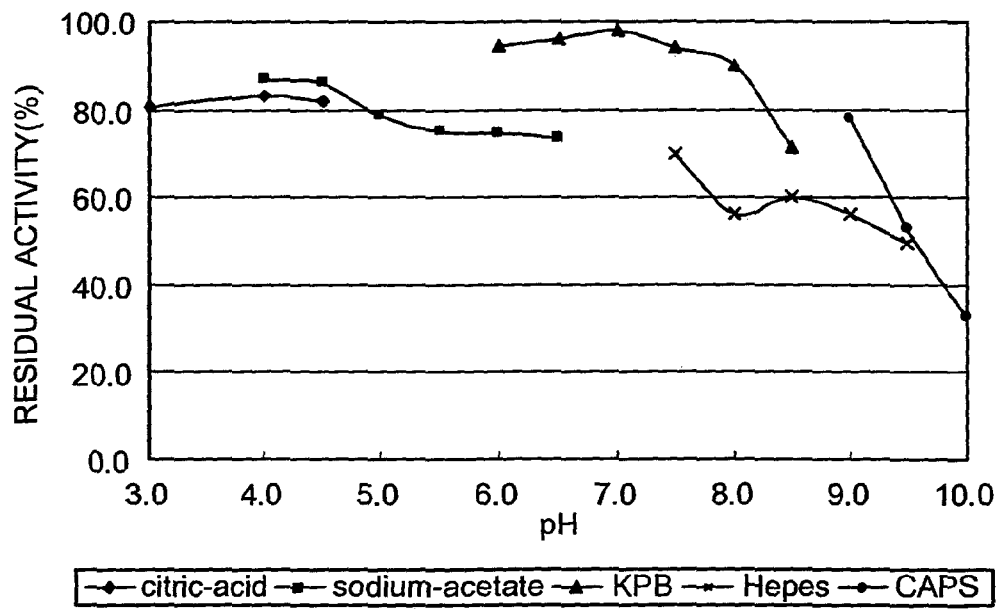
FIG. 4 presents a graph showing results of measuring pH stability of SpALD.

The pH stability in the range of pH 3 to 10 was measured. Buffers used for the measurement were as follows. Sodium citrate buffer (pH 3, 4, 4.5), sodium acetate buffer (pH 4, 4.5, 5, 5.5, 6, 6.5), potassium phosphate buffer (pH 6, 6.5, 7, 7.5, 8, 8.5), Hepes-KOH buffer (pH 7.5, 8, 8.5, 9, 9.5), CAPS-NAOH buffer (pH 9, 9.5, 10). After the SpALD was incubated in 100 mM of each buffer at 37° C. for 30 min, a residual activity was measured under the primary measurement condition. The results are shown in FIG. 4.

(3) Temperature Stability

Figure 5:
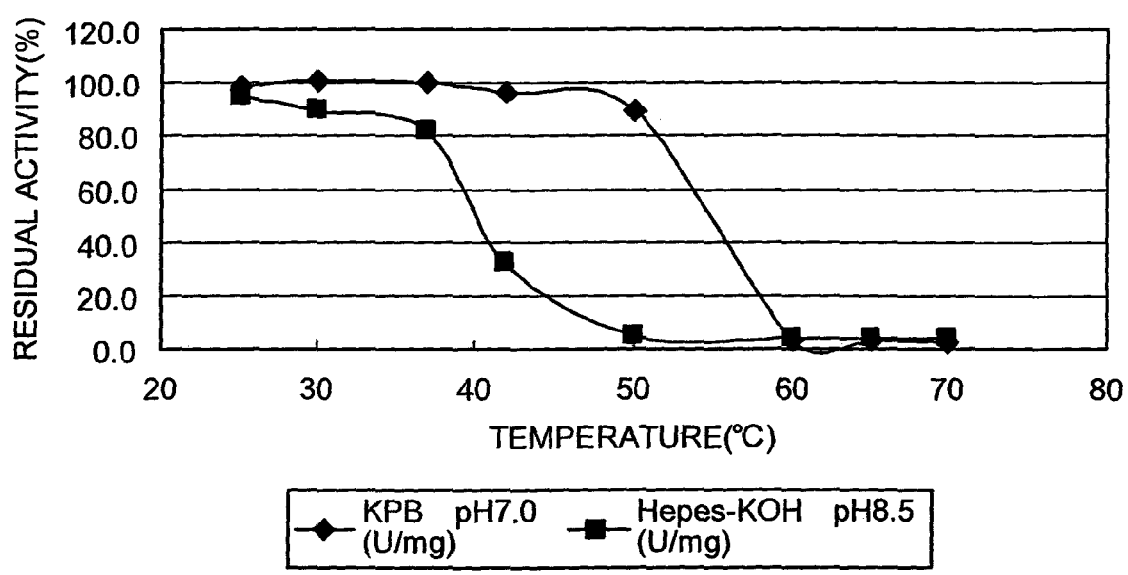
FIG. 5 presents a graph showing results of measuring temperature stability of SpALD.

After the SpALD was incubated in 100 mM potassium phosphate buffer (pH 7.0) and 100 mM Hepes-KOH buffer (pH 8.5) at 25 to 70° C. for 30 min, a residual activity was measured under the primary measurement condition. The results are shown in FIG. 5.

(4) Optimal pH

Figure 6:
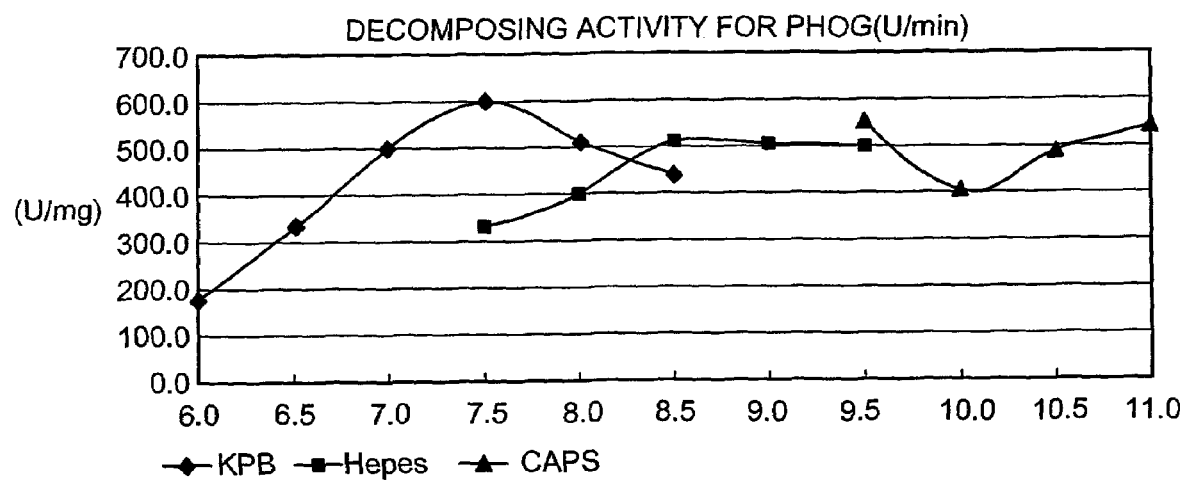
FIG. 6 presents a graph showing reaction optimal pH of SpALD in an aldol degradation activity.

A PHOG-degrading activity at 30° C. was measured by a colorimetric method (FIG. 6). As a result, it was shown that the optimal pH of a PHOG retro-aldol cleavage reaction was around pH 7.5.

Figure 7:
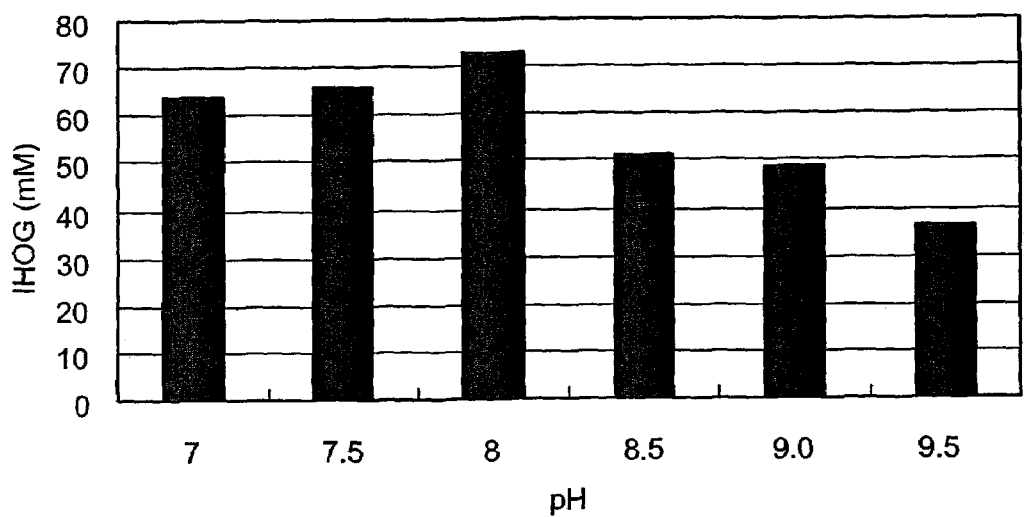
FIG. 7 presents a graph showing reaction optimal pH of SpALD in an aldol condensation activity.

An IHOG synthetic activity using 300 mM IPA and 750 mM pyruvic acid as the substrates was measured at each pH (reaction condition: 100 mM Hepes-KOH (pH 8.5), 300 mM IPA, 750 mM PA, 1 mM $MgCl_2$, 37° C., 16 h). Values obtained by subtracting an amount of produced IHOG without the enzyme from an amount of produced IHOG with the enzyme are shown in FIG. 7. As a result, it was shown that the optimal pH of the IHOG aldol condensation by SpALD was around pH 8.0.

Example 9

Synthesis of IHOG by SpALD

One platinum loop of microbial cells of *E. coli*/ptrpSpALD cultivated in LB-amp agar plate at 37° C. for 16 hours was inoculated 12 of 500 mL flasks containing 50 mL of the LB-amp medium. Then, the shaking culture was conducted at 37° C. for 16 hours. Microbial cells were harvested from the obtained culture by the centrifugation, suspended in and washed with the buffer A (20 mM Hepes-KOH, pH 7.6), and subsequently centrifuged again to recover the microbial cells. Microbial cells (wet microbial cell weight: about 3 g) collected by the centrifugation were suspended in 300 mL of a reaction mixture of the following composition.

IHOG synthetic reaction mixture: 50 mM Hepes-KOH (pH 8.5), 300 mM indole pyruvic acid, 750 mM pyruvic acid sodium salt, 1 mM $MgCl_2$, 5 mM potassium phosphate buffer (pH 8.5). (adjusted to pH 8.5 with 6N KOH)

The reaction mixture in which the microbial cells had been suspended was bubbled with the argon gas, and thereafter the reaction was performed under the argon gas atmosphere. The reaction was performed with stirring at 37° C. for 20 hours. After the completion of the reaction, 300 mL of the aldol reaction mixture was obtained by centrifuging to remove the microbial cells.

Example 10

Oximation of Aldol Reaction Mixture and Isolation of 4R-IHOG-Oxime

As a pH value was maintained at 9 with an aqueous solution of 8N sodium hydroxide, 18.8 g (270 mmol) of hydroxylamine hydrochloride was added to the aldol reaction mixture obtained in Example 9, which was then stirred at 25° C. for 3 hours and 10° C. overnight. An concentration of IHOG-oxime in the obtained reaction mixture was quantitatively determined by the HPLC analysis. As a result, 25 mmol of 4-hydroxy-4-(3-indolylmethyl)-2-hydroxyiminoglutaric acid (IHOG-oxime) was produced in the reaction mixture. The asymmetry at position 4 was analyzed, and it was confirmed that 21.4 mmol of 4R-IHOG-oxime and 3.6 mmol of 4S-IHOG-oxime were produced. Thus, the 4R-isomer had been preferentially produced at an optical purity of 71.3% e.e.

The pH value of the obtained reaction mixture was adjusted to 2 using concentrated hydrochloric acid, and organic matters were extracted with ethyl acetate. An organic layer was concentrated to yield residue. To the residue, 12 mL of 28% aqueous ammonia and 25 mL of water were added, and crystallization was performed by adding 138 mL of 2-propanol to yield 9.76 g (wet weight) of diammonium salt of 4-hydroxy-4-(3-indolylmethyl)-2-hydroxyiminoglutaric acid as crystal. The yielded crystal was dissolved in 60 mL of water, then 50 mL of 2-propanol was added at 50° C., and further 150 mL of 2-propanol was dripped over 3 hours at 50° C. Then, 5.38 g (15.8 mmol) of IHOG-oxime diammonium salt was yielded by filtering the yielded crystal and drying it under reduced pressure. The asymmetry at position 4 of the yielded crystal was analyzed, and the optical purity as the 4R isomer was 99.0% e.e. Thus, 4R-IHOG-oxime ammonium salt with high purity could be isolated and yielded by crystallizing from 2-propanol.

Example 11

Production of 4R-Monatin by Chemical Reduction of 4R-IHOG-Oxime

The ammonium salt of (4R)-4-hydroxy-4-(3-indolylmethyl)-2-hydroxyiminoglutaric acid (5.38 g, 15.8 mmol) obtained in Example 10 was dissolved in 60 mL of 28% aqueous ammonia, 2.84 g of 5% rhodium carbon (50% hydrate product) was added thereto, and the reaction was conducted at room temperature under a hydrogen pressure of 1 MPa. After 17 hours, a catalyst was filtered out (0.2 μm filter), and 1.04 g (7.5 mmol) of potassium carbonate was dissolved in the filtrate. The dissolved solution was concentrated, and 20 mL of ethanol was added to 15.4 g of the yielded concentrate, which was then stirred at 25° C. Further 30 mL of ethanol was dripped thereto over 3 hours, which was then stirred at 25° C. for 17 hours.

The resulting wet crystal (2.93 g) was dissolved in 4 mL of water, 8 mL of ethanol was added at 35° C., and then 17 mL of ethanol was dripped over 3 hours at 35° C. This resulting ethanol solution was cooled to 10° C. over 4 hours, and stirred at 10° C. for one hour. The resulting wet crystal (2.30 g) was dried under reduced pressure to yield the objective substance, 1.99 g of (2R,4R)-monatin K salt. The optical purity of the obtained monatin was 99.6% d.e.

$^1$HNMR (400 MHz, D$_2$O) δ:2.06 (dd, J=11.8, 15.3 Hz, 1H), 2.67 (dd, J=2.0, 15.2 Hz, 1H), 3.08 (d, J=14.4 Hz, 1H), 3.28 (d, J=14.4 Hz, 1H), 3.63 (dd, J=2.2, 12.2 Hz, 1H), 7.12-7.16 (m, 1H), 7.20-7.24 (m, 2H), 7.48-7.49 (m, 1H), 7.71-7.73 (m, 1H).

ESI-MS Calculated value: $C_{14}H_{16}N_2O_{5=292.29}$, Analytical value: 291.28 [M-H]$^-$

Example 12

Improvement of IHOG Synthesis by SpALD

One platinum loop of microbial cells of *E. coli*/ptrpSpALD cultivated in LB-amp agar plate at 37° C. for 16 hours was inoculated 12 of 500 mL flasks containing 50 mL of the LB-amp medium. Then, the shaking culture was conducted at 37° C. for 16 hours. Microbial cells were collected from the obtained culture by the centrifugation, suspended in and washed with the buffer A (20 mM Hepes-KOH, pH 7.6), and subsequently centrifuged again to recover the microbial cells. The microbial cells (wet weight: about 3 g) prepared by the centrifugation were suspended in 300 mL of the reaction mixture of the following composition.

IHOG synthetic reaction mixture: 50 mM phosphate buffer (pH 8.7), 300 mM indole pyruvic acid, 600 mM pyruvic acid sodium salt, 0.1 mM MgCl$_2$. (adjusted to pH 8.5 with 6N KOH)

The suspension in which the microbial cells had been suspended was bubbled with the argon gas, and thereafter the reaction was performed under the argon gas atmosphere. The reaction was conducted with stirring at 37° C. for 20 hours. After the completion of the reaction, 300 mL of the aldol reaction mixture was obtained following centrifugation to remove the microbial cells. The resulting reaction mixture was oximated in the same manner as in Example 10, and subsequently produced IHOG was quantitatively determined by HPLC. As a result, 63.6 mM of 4R-IHOG with an optical purity of 92.2% e.e. was produced, indicating that using SpALD could enhance the 4R selectivity.

Example 13

Cloning of Aldolase Gene (Buald) from C24 Strain (*Burkholderia* sp. AJ110371 Strain) and Large-Scale Expression Thereof in *E. coli*

A gene encoding 4R-IHOG aldolase (BuALD) was obtained from C24 strain among enriched microbial cells collected and found to have the 4R-IHOG aldolase activity in Example 1. The buald gene was ligated to ptrp4 to express on a large scale in *E. coli* JM109.

(1) Preparation of Chromosomal DNA

C24 strain (*Burkholderia* sp. AJ11037 strain) was cultivated using 50 mL of CM2G medium at 30° C. overnight (pre-cultivation). A mass cultivation was conducted using 5 mL of this culture as an inoculum and using 50 mL of the bouillon medium. After cultivating until a logarithmic growth late phase, 50 mL of the culture was subjected to the centrifugation (12000×g, 4° C., 15 min) to collect microbial cells. Using these microbial cells, chromosomal DNA was prepared in accordance with standard methods.

(2) Acquisition of Buald Gene by Southern Analysis and Colony Hybridization

The buald gene was obtained using a DNA fragment encoding the full-length SpALD gene as a probe by Southern analysis and colony hybridization. Using the primers (SEQ ID NOS:10 and 11) shown in Table 9, the full-length spald gene was amplified by PCR from the chromosomal DNA of C77 strain (*Sphingomonas* sp. AJ110329 strain). A DNA probe was made using the amplified fragment, and was labeled by the use of DIG High Prime (supplied from Roche Diagnostics) and by incubating at 37° C. overnight in accordance with instructions. The Southern analysis was conducted by completely digesting 1 μg of the chromosomal DNA prepared from C24 strain with various restriction enzymes, electrophoresing on 0.8% agarose gel, blotting onto a nylon membrane, and then performing following steps in accordance with the manual.

Hybridization was conducted using DIG Easy Hyb (supplied from Roche Diagnostics), prehybridization was performed at 50° C. for one hour, and subsequently the probe was added to perform the overnight hybridization. Bands were detected using DIG Nucleotide Detection Kit. As a result, a PstI/SmaI fragment of about 2.3 kbp that had strongly hybridized with the probe of the PCR fragment was detected. Subsequently, this PstI/BamHI fragment was obtained by the colony hybridization. The chromosomal DNA (20 μg) was treated with PstI/SmaI, and subjected to the agarose gel electrophoresis to obtain a fragment of about 2.3 kbp. This was ligated to pUC18, and the library was made in *E. coli* JM109. Colonies were transferred onto a nylon membrane filter (Hybond-N, supplied from Amersham), and alkali modification, neutralization and fixation were given thereto. The hybridization was performed using DIG Easy Hyb. The filter was immersed in the buffer, and prehybridized at 42° C. for one hour. Subsequently, the labeled probe was added and then hybridization was performed at 42° C. for 16 hours. After washing with SSC, the colony that hybridized with the probe was detected using DIG Nucleotide Detection Kit (supplied from Roche Diagnostics). As a result, the clone that had strongly hybridized with the probe was obtained.

The nucleotide sequence of the plasmid DNA harvested from the obtained clone was determined, and consequently it was demonstrated that the plasmid DNA had the nucleotide sequence of SEQ ID NO:11. Thus, the objective full-length buald gene was obtained.

(3) Construction of Aldolase Gene-Expressing Plasmid ptrpBuALD and Expression Thereof in *E. coli*

A fragment amplified using the primers (SEQ ID NOS:19 and 20) shown in Table 10 from the chromosomal DNA of C24 strain (*Burkholderia* sp. AJ110371 strain) was digested with NdeI/PstI, and inserted into NdeI/PstI site of pTrp4 to construct a plasmid ptrpBuALD. This plasmid expresses the aldolase gene composed of the amino acid sequence of SEQ ID NO:15 obtained by translating the nucleotide sequence from ATG at No. 531 as the translation initiation codon to No. 1385 in the nucleotide sequence of SEQ ID NO:14.

TABLE 10

Primer sequences for construction of ptrpBuALD

| | |
|---|---|
| C24ALD5' Nde: (SEQ ID NO. 19) | ATC CAT ATG TCC AAC ATT CGC CTC AAC AGC (30 MER) |
| C24ALD3' Pst: (SEQ ID NO. 20) | CGC CTG CAG TCA GTA GCC AGC CAT ATC GCG CGC (33 MER) |

E. coli JM109 was transformed with the constructed expression plasmid, and one platinum loop of the resulting transformant was inoculated to 50 mL of LB medium containing 100 μg/mL ampicillin and shaken at 37° C. for 16 hours. After the cultivation, microbial cells were harvested from 1 mL of the resulting culture, washed and suspended in 1 mL of 20 mM Hepes-KOH (pH 7.6), and microbial cells were disrupted ultrasonically. A supernatant was obtained by centrifuging a disruption suspension at 15000 rpm for 10 min to use as a crude enzyme solution.

The aldolase activity was measured using the crude enzyme solution. The aldolase activity was measured as the aldole cleavage activity using PHOG as the substrate under the following conditions.

Reaction conditions: 50 mM Hepes-KOH (pH 8.5), 2 mM PHOG, 0.25 mM NADH, 0.2 mM KPi, 1 mM $MgCl_2$, 16 U/mL lactate dehydrogenase, 3 μL of enzyme per 600 μL of reaction mixture, 30° C., the absorbance at 340 nm was measured.

As a result, no aldolase activity was detected in E. coli transformed with pTrp4 (control) whereas 231 U/mg protein of the aldolase activity was detected in the strain transformed with ptrpBuALD. This confirmed that the objective aldolase gene was certainly cloned and that the plasmid of BuALD was constructed with high expression.

Example 14

Purification of Recombinant Aldolase Enzyme Derived from C24 Strain (*Burkholderia* sp. AJ 110371 Strain)

Recombinant BuALD was purified from a soluble fraction of E. coli which had resulted in high expression of the aldolase (BuALD) derived from C24 strain (*Burkholderia* sp. AJ110371 strain) as follows. The aldolase activity was measured as the aldole cleavage activity using PHOG as the substrate under the following conditions.

Reaction conditions: 50 mM Hepes-KOH (pH 8.5), 2 mM PHOG, 0.25 mM NAD, 1 mM $MgCl_2$, 16 U/mL lactate dehydrogenase, 3 μL of enzyme per 600 μL of reaction mixture, 30° C., the absorbance at 340 nm was measured.

(1) Preparation of Soluble Fraction

One platinum loop of microbial cells of E. coli/ptrpBuALD cultivated in LB-amp agar plate at 37° C. for 16 hours was inoculated 10 of 500 mL flasks containing 50 mL of the LB-amp medium. Then, the shake culture was conducted at 37° C. for 16 hours. Microbial cells were harvested from the obtained culture by the centrifugation, suspended in and washed with the buffer A (20 mM Hepes-KOH, pH 7.6), and subsequently centrifuged again to recover the microbial cells. The obtained washed microbial cells were suspended in 20 mL of the buffer A, and disrupted ultrasonically at 4° C. for 30 min. Microbial cell debris was removed by centrifuging a disruption suspension (×8000 rpm, 10 min, twice), and the resulting supernatant was used as a crude extraction fraction.

(2) Anion Exchange Chromatography: Q-Sepharose FF

The soluble fraction (20 mL) obtained above was applied on an anion exchange chromatography column Q-Sepharose FF 26/10 (supplied from Pharmacia, CV=20 mL) pre-equilibrated with the buffer A to absorb proteins to the carrier. Proteins that had not been absorbed to the carrier (unabsorbed proteins) were washed out using the buffer A. Subsequently, an absorbed proteins were eluted by linearly changing a KCl concentration from 0 M to 0.7 M (total 140 mL). A PHOG aldolase activity was measured at each eluted fraction, and consequently a peak of the PHOG aldolase activity was detected in the fraction corresponding to about 0.35 M.

(3) Hydrophobic Chromatography: Phenyl Sepharose HP HR 16/10

A solution in which the aldolase activity had been detected was dialyzed against buffer B (20 mM Hepes-KOH, 1 M ammonium sulfate, pH 7.6) at 4° C. overnight, and filtered through a filter with a pore size of 0.45 μm. The obtained filtrate was applied on a hydrophobic chromatography column, Phenyl Sepharose HP HR 16/10 (supplied from Pharmacia) pre-equilibrated with the buffer B. This procedure allowed the aldolase to absorb to the carrier.

Unabsorbed proteins onto the carrier were washed out using the buffer B, and then the aldolase was eluted with a linear gradient of the concentration of ammonium sulfate from 1 M to 0 M. The aldolase activity was measured for each eluted fraction, and the aldolase activity was detected in eluted positions where the concentration of ammonium sulfate was about 0.4 to 0.5 M.

(4) Gel Filtration Chromatography: Sephadex 200 HP 16/60

Fractions containing the aldolase were gathered, dialyzed against the buffer A, and filtered through the filter with a pore size of 45 μm. The obtained filtrate was concentrated using an ultrafiltration membrane, centriprep 10. The obtained concentrated solution was applied on a gel filtration Sephadex 200 HP 16/60 (supplied from Pharmacia) pre-equilibrated with buffer C (20 mM Hepes-KOH, 0.1 M KCl, pH 7.6), and eluted at a flow rate of 1 mL/min. This procedure allowed the aldolase to be eluted in fractions of about 66 mL.

(5) Anion Exchange Chromatography: Mono Q HR 5/5

The obtained fraction was filtered through the filter with a pore size of 0.45 μm. The obtained filtrate was applied on an anion exchange chromatography column Mono-Q HR 5/5 (supplied from Pharmacia) pre-equilibrated with the buffer A. This procedure allowed the aldolase to absorb to the carrier. Unabsorbed proteins were washed out with the buffer A, and subsequently the protein was eluted with a linear gradient of the concentration of KCl from 0 mM to 700 mM (total 24 mL). The aldolase activity was measured for each fraction, and the aldolase activity was detected in the eluted positions where the concentration of KCl was about 0.4 M.

The fractions purified by the above column chromatography were subjected to SDS-PAGE, and then a single band at a position corresponding to about 30 kDa was detected by CBB staining. The obtained solution of recombinant BuALD was dialyzed against the buffer A at 4° C. overnight. This allowed production of 1.5 mL of the solution containing 1241 U/mL of BuALD.

Example 15

Enzymological Characters of BuALD

The followings were investigated using the BuALD prepared in Example 14.

Primary measurement conditions: 50 mM Hepes-KOH (pH 8.5), 2 mM PHOG, 5 mM $MgCl_2$, 16 U/mL lactate dehydrogenase, the decreased of the absorbance at 340 nm was measured at 30° C.

(1) Kinetics Constant Using PHOG as Substrate

Figure 8A:
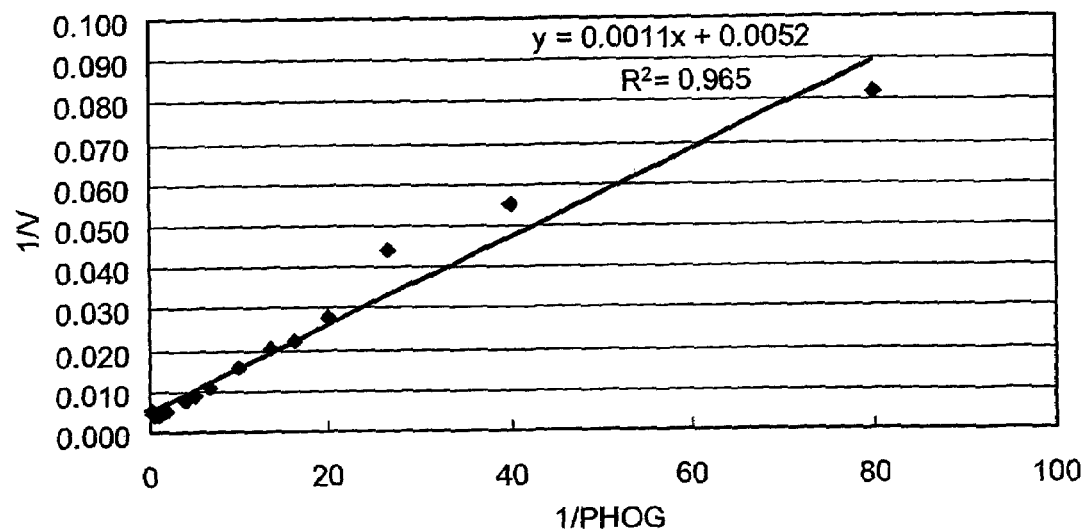
FIG. 8A presents a graph showing reaction rates of BuALD using PHOG as a substrate.
Figure 8B:
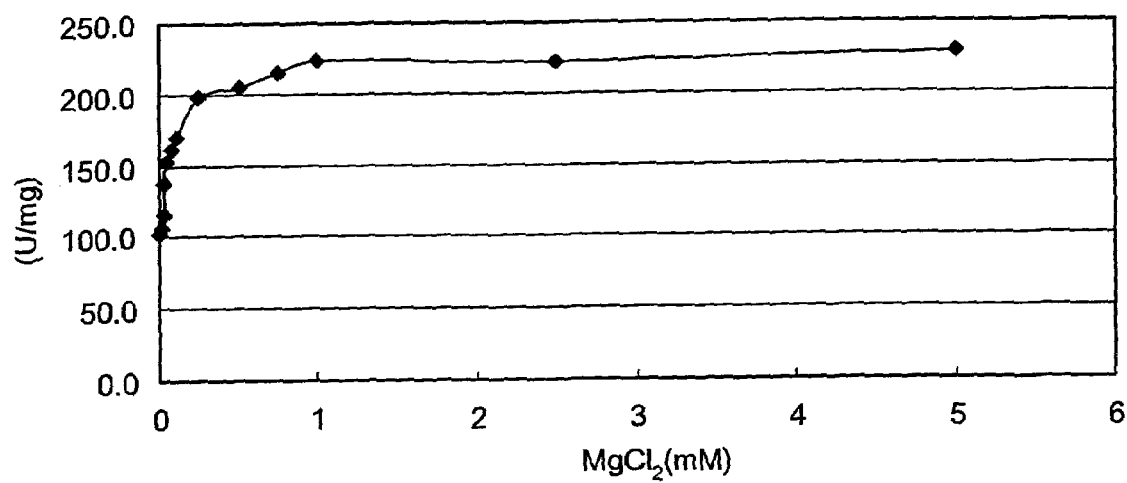
FIG. 8B presents a graph showing reaction rates of BuALD versus MgCl$_2$ concentrations.

From the results shown in FIGS. 8A and 8B, the following was determined: Vmax (for PHOG)=483 μmol/min/mg, Km (for PHOG)=0.66 mM, Km (for $MgCl_2$)=0.021 mM. No increase of the aldolase activity by the addition of KPB solution was observed.

(2) pH Stability

Figure 9:
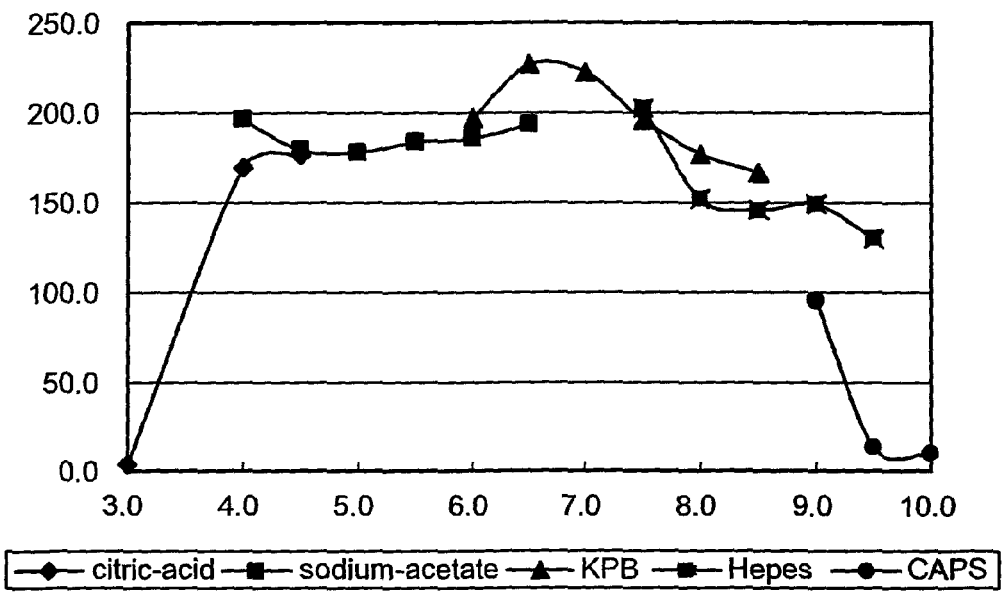
FIG. 9 presents a graph showing results of measuring pH stability of BuALD.

The pH stability in the range of pH 3 to 10 was measured. Buffers used for the measurement were as follows. Sodium citrate buffer (pH 3, 4, 4.5), sodium acetate buffer (pH 4, 4.5, 5, 5.5, 6, 6.5), potassium phosphate buffer (pH 6, 6.5, 7, 7.5, 8, 8.5), Hepes-KOH buffer (pH 7.5, 8, 8.5, 9, 9.5), CAPS-NAOH buffer (pH 9, 9.5, 10). After the BuALD was incubated in 100 mM of each buffer at 37° C. for 30 min, the residual activity was measured under the primary measurement condition. The results are shown in FIG. 9.

(3) Temperature Stability

Figure 10:
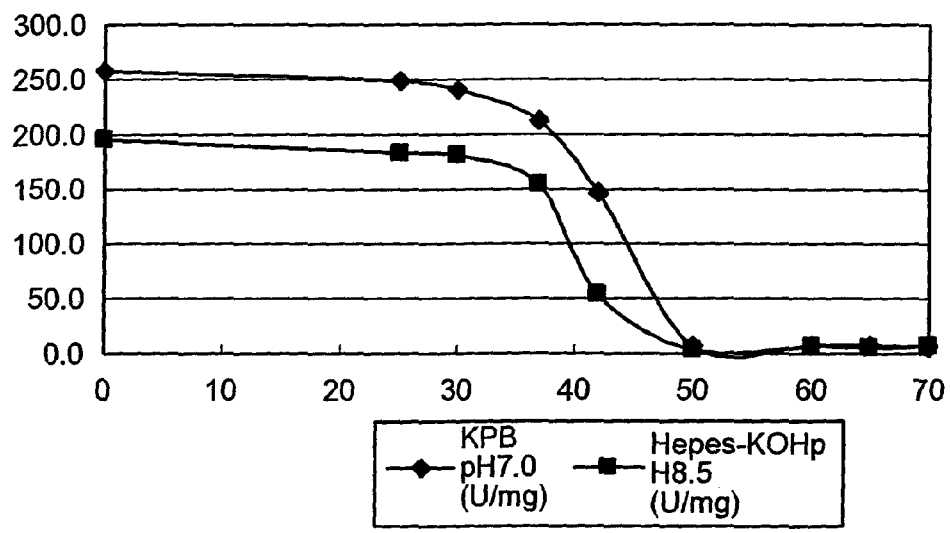
FIG. 10 presents a graph showing results of measuring temperature stability of BuALD.

After the BuALD was incubated in 100 mM potassium phosphate buffer (pH 7.0) and 100 mM Hepes-KOH buffer (pH 8.5) at 25 to 70° C. for 30 min, the residual activity was measured under the primary measurement condition. The results are shown in FIG. 10.

Example 16

Synthesis and Oximation of IHOG by BuALD and SpALD

One platinum loop of microbial cells of *E. coli* JM109/ptrpBuALD or *E. coli* JM109/ptrpSpALD cultivated in LB-amp agar plate at 37° C. for 16 hours was inoculated 4 of 500 mL flasks containing 50 mL of the LB-amp medium. Then, the shaking culture was conducted at 37° C. for 16 hours. Microbial cells were harvested from the obtained culture by the centrifugation, suspended in and washed with the buffer A (20 mM Hepes-KOH, pH 7.6), and subsequently centrifuged again to recover the microbial cells. Microbial cells (wet microbial cell weight: about 1 g) prepared by the centrifugation were suspended in 100 mL of the reaction mixture of the following composition.

IHOG synthetic reaction mixture: 50 mM KPB (pH 8.0), 300 mM indole pyruvic acid, 600 mM pyruvic acid sodium salt, 0.1 mM $MgCl_2$. (adjusted to pH 8.0 with 6N KOH)

The reaction mixture in which the microbial cells had been suspended was bubbled with the argon gas, and subsequently, the reaction was conducted with stirring at 37° C. for 18 hours. After the completion of the reaction, about 100 mL of the aldol reaction mixture was obtained by centrifugation for removing the microbial cells.

As the pH value was maintained at 9 with an aqueous solution of 6N sodium hydroxide, 6.25 g (90 mmol) of hydroxylamine hydrochloride was added to about 96 mL of the aldol reaction mixture obtained, which was then stirred at 25° C. for 6 hours and 110° C. overnight. An amount of IHOG-oxime in the obtained reaction mixture was quantitatively determined by the HPLC analysis. As a result (Table 11), in both BuALD group and SpALD group, 4R-IHOG-oxime was preferentially produced.

TABLE 11

| | 4R-IHOG (mM) | 4S-IHOG (mM) | 4R yield (%) | 4R e.e. (%) |
|---|---|---|---|---|
| BuALD | 70.6 | 12.4 | 23.5 | 70.2 |
| SpALD | 71.4 | 2.1 | 23.8 | 94.3 |

Example 17

Cloning of Aldolase Gene (SpALD2) from C43 Strain (*Sphingomonas* sp. AJ110372 Strain) and Large-Scale Expression Thereof in *E. coli*

A gene encoding 4R-IHOG aldolase (SpALD2) was obtained from C43 strain that was selected from bacteria in enriched culture and was found to have the 4R-IHOG aldolase activity in Example 1. The spald2 gene was ligated to ptrp4 to express on a large scale in *E. coli* JM109.

(1) Preparation of Chromosomal DNA

C43 strain (*Sphingomonas* sp. AJ110372 strain) was cultivated using 50 mL of CM2G medium at 30° C. overnight (pre-cultivation). A main cultivation was conducted using 5 mL of this pre-cultivation as an inoculum and using 50 mL of the broth medium. After cultivating until a logarithmic growth late phase, 50 mL of the culture was subjected to the centrifugation (12000×g, 4° C., 15 min) to collect microbial cells. Using these microbial cells, chromosomal DNA was prepared in accordance with standard methods.

(2) Acquisition of spald2 Gene by Southern Analysis and Colony Hybridization

The spald2 gene was obtained using a DNA fragment encoding the full-length SpALD gene as a probe by Southern analysis and colony hybridization. Using the primers (SEQ ID NOS:10 and 11) shown in Table 9, the full-length spald gene was amplified by PCR from the chromosomal DNA of C77 strain (*Sphingomonas* sp. AJ110329 strain). A DNA probe was made using the amplified fragment, and was labeled by the use of DIG High Prime (supplied from Roche Diagnostics) and by incubating at 37° C. overnight in accordance with instructions. The Southern analysis was conducted by completely digesting 1 μg of the chromosomal DNA prepared from C43 strain with various restriction enzymes, electrophoresing on 0.8% agarose gel, blotting onto a nylon membrane, and then performing following steps in accordance with the manual.

Hybridization was performed using DIG Easy Hyb (supplied from Roche Diagnostics), prehybridization was conducted at 50° C. for one hour, and subsequently the probe was added to perform the overnight hybridization. Bands were detected using DIG Nucleotide Detection Kit. As a result, a PstI fragment of about 3 kbp that had strongly hybridized to the probe of the PCR fragment was detected. Subsequently, this PstI fragment was obtained by the colony hybridization. The chromosomal DNA (20 μg) was treated with PstI, and subjected to the agarose gel electrophoresis to recover a fragment of about 3 kbp. This was ligated to pUC118, and the library was made in *E. coli* JM109. Colonies were transferred onto a nylon membrane filter (Hybond-N, supplied from Amersham), and alkali modification, neutralization and fixation were given thereto. The hybridization was performed using DIG Easy Hyb. The filter was immersed in the buffer, and prehybridized at 42° C. for one hour. Subsequently, the labeled probe was hybridized at 42° C. for 16 hours. After washing with SSC, the colony that had hybridized with the probe was detected using DIG Nucleotide Detection Kit (supplied from Roche Diagnostics). As a result, the clone that had strongly hybridized with the probe was obtained.

The nucleotide sequence of the plasmid DNA recovered from the obtained clone was determined, and consequently it was demonstrated that the plasmid DNA had the nucleotide sequence of SEQ ID NO:12. Thus, the objective full-length spald2 gene was obtained.

(3) Construction of Aldolase Gene-Expressing Plasmid pUCSpALD2 and Expression Thereof in *E. coli*

A fragment amplified using the primers (SEQ ID NOS:21 and 22) shown in Table 12 from the chromosomal DNA of *Sphingomonas* sp. C43 strain was digested with EcoRI/PstI, and inserted into EcoRI/PstI site of pUC18 to construct a plasmid pUCSpALD2. This plasmid expresses the aldolase gene composed of the amino acid sequence of SEQ ID NO:13 obtained by translating the nucleotide sequence from ATG at No. 399 as the translation initiation codon to No. 1253 in the nucleotide sequence of SEQ ID NO:12.

TABLE 12

Primer sequences for construction of pUCSpALD2

| | |
|---|---|
| SpALD2_Eco: (SEQ ID NO. 21) | CCG GAA TTC CAT GAA GGA ATG ATC TGA GAT GAC C (34 mer) |
| SpALD2_ter_Pst: (SEQ ID NO. 22) | AAA AAC TGC AGC TAG TAG CCC GCC AGT TCG CGA CCC (36 mer) |

*E. coli* JM109 was transformed with the constructed expression plasmid, and one platinum loop of the resulting transformant was inoculated to 50 mL of LB medium containing 100 μg/mL ampicillin and 0.1 mM Isopropyl-b-D-thiogalactopyranoside (IPTG) and shaken at 37° C. for 16 hours. After the completion of the cultivation, microbial cells were collected from 1 mL of the resulting culture, washed, suspended in 1 mL of 20 mM Hepes-KOH (pH 7.6), and microbial cells were disrupted ultrasonically. A supernatant was obtained by centrifuging a disruption suspension at 15000 rpm for 10 min to use as a crude enzyme solution.

The aldolase activity was measured using the crude enzyme solution. The aldolase activity was measured as the aldole cleavage activity using PHOG as the substrate under the following conditions.

Reaction conditions: Hepes-KOH (pH 8.5), 2 mM PHOG, 0.25 mM NADH, 1 mM $MgCl_2$, 16 U/mL lactate dehydrogenase, 3 μL of enzyme per 600 μL of reaction mixture, 30° C., the absorbance at 340 nm was measured.

As a result of measuring, no aldolase activity was detected in *E. coli* (control) transformed with pUC18 whereas 33.6 U/mg protein of the aldolase activity was detected in the strain transformed with pUCSpALD2. This confirmed certain cloning the objective gene for aldolase as well as the construction of the plasmid with high expression of SpALD2.

Example 18

Synthesis of IHOG and IHOG-Oxime by SpALD2

One platinum loop of microbial cells of *E. coli* JM109/pCUSpALD2 cultivated in LB-amp agar plate at 37° C. for 16 hours was inoculated 4 of 500 mL flasks containing 50 mL of the LB medium containing 100 μg/mL ampicillin and 0.1 mM IPTG. Then, the shaking culture was conducted at 34° C. for 16 hours. Microbial cells were harvested from the obtained culture by the centrifugation, suspended in and washed with the buffer A (20 mM Hepes-KOH, pH 7.6), and subsequently centrifuged again to collect the microbial cells. Microbial cells (wet microbial cell weight: about 1 g) prepared by the centrifugation were suspended in 100 mL of the reaction mixture of the following composition.

IHOG synthetic reaction mixture: 50 mM KPB (pH 8.0), 300 mM indole pyruvic acid, 600 mM pyruvic acid sodium salt, 0.1 mM $MgCl_2$. (adjusted to pH 8.0 with 6N KOH)

The reaction mixture in which the microbial cells had been suspended was bubbled with the argon gas, and subsequently, the reaction was conducted with stirring at 37° C. for 18 hours. After the completion of the reaction, about 100 mL of the aldol reaction mixture was obtained by centrifuging to remove the microbial cells. An aqueous solution (5.95 mL, 90 mmol) of 50% hydroxylamine was added to about 96 mL of the aldol reaction mixture obtained, which was then stirred at 25° C. for 6 hours and 10° C. overnight. An amount of IHOG-oxime in the obtained reaction mixture was quantitatively determined by the HPLC analysis. As a result, 3.84 mmol of 4R-IHOG-oxime and 0.15 mmol of 4S-IHOG-oxime were produced, indicating that the 4R-isomer was preferentially produced at an optical purity of 92.4% e.e.

Reference Example 1

Synthesis of 4-hydroxy-4-(3-indolylmethyl)-2-ketoglutaric acid (IHOG)

Indole-3-pyruvic acid (7.50 g, 35.8 mmol, content 97.0% by weight) and 14.18 (107.4 mmol) g of oxaloacetic acid were added and dissolved in 64.45 mL of water in which 18.91 g (286.5 mmol, content 85% by weight) had been dissolved. This mixed solution was stirred at 35° C. for 24 hours.

Further, 40.0 mL of 3N hydrochloric acid was added to neutralize (pH 7.0), and 153.5 g of a neutralized reaction mixture was obtained. In this neutralized mixture, 5.55 g of 4-hydroxy-4-(3-indolylmethyl)-2-ketoglutaric acid was contained, and a yield (versus indole pyruvic acid) was 53.3%.

Water was added to this neutralized mixture to make 168 mL, which was then passed through a resin column filled with 840 mL of a synthetic absorbent (DIAION-SP207, supplied from Mitsubishi Chemical Corporation). An aqueous solution containing 3.04 g of 4-hydroxy-4-(3-indolylmethyl)-2-ketoglutaric acid with high purity was obtained by passing purified water at a flow rate of 23.5 mL per min and collecting 1.73 to 2.55 (L/L-R), and the yield (versus an applied amount onto the resin) was 54.7%.

(NMR Measurement)

$^1$H-NMR (400 MHz, $D_2O$): 3.03 (d, 1H, J=14.6 Hz), 3.11 (d, 1H, J=14.6 Hz), 3.21 (d, 1H, J=18.1 Hz), 3.40 (d, 1H, J=18.1 Hz), 7.06-7.15 (m, 3H), 7.39 (d, 1H, J=7.8 Hz), 7.66 (d, 1H, J=7.8 Hz).

$^{13}$C-NMR (100 MHz, $D_2O$): δ5.43, 47.91, 77.28, 109.49, 112.05, 119.44, 119.67, 121.91, 125.42, 128.41, 136.21, 169.78, 181.43, 203.58

Reference Example 2

Synthesis of 4-phenylmethyl-4-hydroxy-2-ketoglutaric acid (PHOG)

Phenyl pyruvic acid (5.0 g, 30.5 mmol) and 12.1 g (91.4 mmol) of oxaloacetic acid were added to 25 mL of aqueous solution in which 13.8 g of potassium hydroxide (purity 85%) had been dissolved, and reacted at room temperature for 72 hours. A pH value of the reaction mixture was adjusted to 2.2 using concentrated hydrochloric acid, and the reaction mixture was extracted with ethyl acetate. An organic layer was washed with saturated aqueous NaCl solution, dried on magnesium sulfate anhydrate, and then concentrated to yield residue. The residue was recrystallized from ethyl acetate and toluene to yield 2.8 g (11.3 mmol) of 4-phenylmethyl-4-hydroxy-2-ketoglutaric acid as crystal.

(NMR Measurement)
$^1$H NMR (D$_2$O) δ: 2.48 (d, J=14.4 Hz, 0.18H), 2.60 (d, J=14.4 Hz, 0.18H), 2.85-3.30 (m, 3.64H), 7.17-7.36 (m, 5H)

(Molecular Weight Measurement)
ESI-MS Calculated value C$_{12}$H$_{12}$O$_6$=252.23, Analyzed value 251.22 (MH$^-$)

Reference Example 3

Production of 4-hydroxy-4-(3-indolylmethyl)-2-hydroxyiminoglutaric acid

Indole-3-pyruvic acid (73.8 g, 352 mmol) was added to and dissolved in 917 g of an aqueous solution of 1.6 wt % sodium hydroxide. A temperature of the reaction mixture was maintained at 35° C. As the pH value was maintained at 11.1 using an aqueous solution of 30% sodium hydroxide, 310.2 g (1761 mmol) of an aqueous solution of 50% pyruvic acid was dripped over 2 hours. The reaction was further continued for 4.5 hours to yield a reaction mixture containing 4-hydroxy-4-(3-indolylmethyl)-2-ketoglutaric acid. As the pH value was maintained at 7 with the addition of the aqueous solution of 30% sodium hydroxide, 367.2 g (2114 mmol) of an aqueous solution of 40% hydroxylamine hydrochloride was added thereto, and stirred at 5° C. for 17.5 hours. The pH value of the reaction mixture was adjusted to 2 using concentrated hydrochloric acid, and organic matters were extracted with ethyl acetate. An organic layer was washed with saturated aqueous NaCl solution, and concentrated to yield residue. The residue was recrystallized from 60 mL of 28% aqueous ammonia and 350 mL of 2-propanol to yield 43.4 g of diammonium salt of 4-hydroxy-4-(3-indolylmethyl)-2-hydroxyiminoglutaric acid (142 mmol, yield 40% versus indole-3-pyruvic acid) as crystal.

Reference Example 4

Production of (R)-(+)-1-phenylethylamine salt of (4S)-4-hydroxy-4-(3-indolylmethyl)-2-hydroxyiminoglutaric acid Ammonium salt (44.7 g, 0.131 mol) of 4-hydroxy-4-(3-indolylmethyl)-2-hydroxyiminoglutaric acid was dissolved in 500 mL of water at 25° C., and subsequently the pH value of the aqueous solution was adjusted to 2 with 25.5 g of 36% hydrochloric acid. The acidic solution was subject to extraction with 1300 mL of ethyl acetate, and the ethyl acetate solution was washed with 200 mL of saturated aqueous NaCl solution. An aqueous solution (500 mL) of sodium carbonate (13.9 g, 0.131 mol) was added to the resulting ethyl acetate solution, and stirred to separate an alkali aqueous solution from ethyl acetate. The pH value of the resulting alkali aqueous solution was adjusted to 2 by adding 23.1 g of 36% hydrochloric acid. (R)-(+)-1-Phenylethylamine (6.99 g, 57.6 mmol) was dripped into the resulting acidic aqueous solution, and stirred at 25° C. for one hour. The yielded crystal was filtered, and dried under reduced pressure to yield 21.8 g (47.8 mmol) of (R)-(+)-1-phenylethylamine salt of (4S)-4-hydroxy-4-(3-indolylmethyl)-2-hydroxyiminoglutaric acid (yield: 72.7%, optical purity: 87.4%).

(NMR Measurement)
$^1$H-NMR (400 MHz, DMSO-d$_6$) δ:1.48 (d, 3H, J=6.8 Hz), 2.63 (d, 1H, J=14.0 Hz), 2.70 (d, 1H, J=14.0 Hz), 2.90 (d, 1H, J=14.1 Hz), 3.06 (d, 1H, J=14.1 Hz), 4.40 (q, 1H, J=6.8 Hz), 6.91-7.54 (m, 10H)

Reference Example 5

Production of (S)-(−)-1-phenylethylamine salt of (4R)-4-hydroxy-4-(3-indolylmethyl)-2-hydroxyiminoglutaric acid (S)-(−)-1-Phenylethylamine (7.12 g, 58.7 mmol) was further dripped in the crystal filtrate obtained in Reference Example 4, and stirred at 25° C. for one hour. The yielded crystal was filtered, and dried under reduced pressure to yield 23.8 g (53.3 mol) of (S)-(−)-1-phenylethylamine salt of (4R)-4-hydroxy-4-(3-indolylmethyl)-2-hydroxyiminoglutaric acid (yield: 81.1%, optical purity: 92.1%).

Reference Example 6

(1) Production of ammonium salt of (4S)-4-hydroxy-4-(3-indolylmethyl)-2-hydroxyiminoglutaric acid At 25° C., 21.8 g (51.0 mmol) of (R)-(+)-1-phenylethylamine salt of (4S)-4-hydroxy-4-(3-indolylmethyl)-2-hydroxyiminoglutaric acid was added to 200 mL of water and 18.5 g of 28% aqueous ammonia, and dissolved therein, and then 200 mL of toluene was added thereto and stirred. An aqueous layer obtained by separating the layers was heated to 60° C., and 900 mL of 2-propanol was dripped thereto over 2 hours. This 2-propanol aqueous solution was cooled to 10° C. over 5 hours, and then stirred at 10° C. for 10 hours. The yielded crystal was filtered, and dried under reduced pressure to yield 14.75 g of ammonium salt of (4S)-4-hydroxy-4-(3-indolylmethyl)-2-hydroxyiminoglutaric acid (yield: 85.1%, optical purity: 99.0%).

Melting point: 205° C. (degradation)
Specific optical rotation: [α]$^{20}_D$+13.4 (c=1.00, H$_2$O)

(2) Production of ammonium salt of (4R)-4-hydroxy-4-(3-indolylmethyl)-2-hydroxyiminoglutaric acid In the same way as in the aforementioned Reference Example, 16.2 g of ammonium salt of (4R)-4-hydroxy-4-(3-indolylmethyl)-2-hydroxyiminoglutaric acid (yield: 89.3%, optical purity: 99.9%) was obtained from 23.8 g (53.3 mmol) of (R)-(+)-1-phenylethylamine salt of (4R)-4-hydroxy-4-(3-indolylmethyl)-2-hydroxyiminoglutaric acid.

Specific optical rotation: [α]$^{20}_D$−13.6 (c=1.00, H$_2$O)

Reference Example 7

Production of (2R,4R)-Monatin

Ammonium salt of (4R)-4-hydroxy-4-(3-indolylmethyl)-2-hydroxyiminoglutaric acid (13.2 g, 38.7 mmol) obtained in Reference Example 6 was dissolved in 135 mL of 28% aqueous ammonia, 6.93 g of 5% rhodium carbon (50% aqueous article) was added, and the reaction was performed at 25° C. under hydrogen pressure of 1 MPa. After 24 hours, a catalyst was filtered out (0.2 μm filter), and 2.54 g (18.4 mmol) of potassium carbonate was dissolved in the filtrate. The dissolved solution was concentrated, 20 mL of water and 45 mL of ethanol were added to 32.7 g of the concentrate, and stirred at 25° C. Further 60 mL of ethanol was dripped over 3 hours, and then crystallization was conducted by stirring at 25° C. for 20 hours. The obtained wet crystal (9.78 g) was dissolved in 12 mL of water, 24 mL of ethanol was added, and then 51 mL of ethanol was further dripped over 3 hours. This ethanol solution was cooled to 15° C. over 4 hours, and then stirred at 15° C. for 10 hours. The yielded wet crystal (7.08 g) was dried under reduced pressure to give 5.7 g of the objective potassium salt of (2R,4R)-monatin.

As described in the above, by the use of the aldolase of the present invention, it becomes possible to produce IHOG and PHOG with optical selectivity. The aldolase of the present invention enables to efficiently introduce the asymmetry in the step of the aldol condensation reaction in the synthetic route of monatin, and may be used suitably for the production of optically active IHOG and monatin.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What we claims is:

1. A method for producing (4R)-4-(indole-3-ylmethyl)-4-hydroxy-2-oxoglutaric acid (4R-IHOG) of formula (1) or a salt thereof:

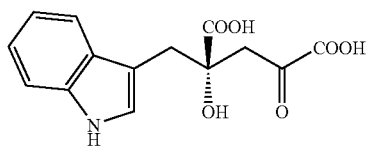

(1)

comprising:
reacting indole-3-pyruvic acid with pyruvic acid or oxaloacetic acid in the presence of a protein or a microorganism containing said protein to produce 4R-IHOG having an optical purity of at least 70%, wherein said protein is selected from the group consisting of:
(a) a protein comprising the amino acid sequence of SEQ ID NO: 15, and
(b) a protein that is at least 95% sequence identical to the protein of SEQ ID NO: 15 and has 4R-aldolase activity.

2. The method according to claim 1,
wherein said protein is obtained from a microorganism selected from bacteria belonging to the genus *Burkholderia*.

3. The method according to claim 2,
wherein the microorganism is *Burkholderia* sp. AJ110371 strain.

4. A method for producing 4R-monatin or a salt thereof comprising:
reacting indole-3-pyruvic acid with pyruvic acid or oxaloacetic acid in the presence of a protein or a microorganism containing said protein to preferentially produce 4R-IHOG, wherein said protein is selected from the group consisting of:
(a) a protein comprising the amino acid sequence of SEQ ID NO: 15, and
(b) a protein that is at least 95% sequence identical to the protein of SEQ ID NO: 15 and has 4R-aldolase activity; and
converting a carbonyl group of 4R-IHOG or the salt thereof to an amino group to produce 4R-monatin of formula (2) or the salt thereof having an optical purity of 4R-monatin or the salt thereof of at least 90%,

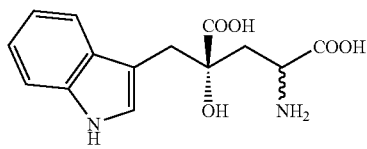

(2)

wherein a bond of a wavy line represents that both R- and S-configurations are included.

5. The method according to claim 4, wherein said converting is by enzymatic amination of said carbonyl group to an amino group and wherein the enzyme for said enzymatic amination is an aminotransferase or a dehydrogenase.

6. The method according to claim 4, wherein said converting comprises,
reacting 4-(indole-3-ylmethyl)-4-hydroxy-2-oxoglutaric acid with an amine compound of formula (3) or a salt thereof:

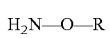 (3)

wherein R represents a hydrogen atom, an alkyl, aryl or aralkyl group, under neutral or alkali conditions to produce 4-hydroxy-4-(3-indolylmethyl)-2-hydroxyiminoglutaric acid (IHOG-oxime) of formula (4) or the salt thereof:

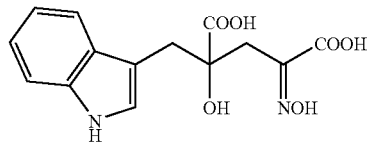

(4)

crystallizing a 4R-isomer of the produced IHOG-oxime or the salt thereof;
reducing the crystallized 4R-isomer to produce 4R-monatin or the salt thereof with an optical purity of at least 90%.

7. The method according to claim 6,
wherein the amine compound of formula (3) is at least one amine compound selected from the group consisting of hydroxylamine, methoxyamine and benzyloxyamine.

8. The method according to claim 6,
wherein the 4R-isomer of IHOG-oxime or the salt thereof is reduced in the presence of hydrogen and a hydrogenated catalyst.

9. The method according to claim 6,
wherein (2R,4R)-monatin is recovered by said crystallizing.

10. The method according to claim 6,
wherein said crystallizing is performed with a crystallization solvent selected from the group consisting of water, an alcohol solvent and an aqueous alcohol solvent.

11. The method according to claim 4,
wherein said protein used in the method is obtained from a microorganism selected from bacteria belonging to the genus *Burkholderia*.

12. The method according to claim 11,
wherein the microorganism *Burkholderia* sp. AJ110371 strain.

13. The method according to claim 1, wherein said protein is a protein comprising the amino acid sequence of SEQ ID NO: 15.

14. The method according to claim 1, wherein said protein is a protein at least 95% sequence identical to the protein of SEQ ID NO: 15 and has 4R-aldolase activity.

15. The method according to claim 4, wherein said protein is a protein comprising the amino acid sequence of SEQ ID NO: 15.

16. The method according to claim 4, wherein said protein is a protein at least 95% sequence identical to the protein of SEQ ID NO: 15 and has 4R-aldolase activity.

17. A method for producing (4R)-4-(indole-3-ylmethyl)-4-hydroxy-2-oxoglutaric acid (4R-IHOG) of formula (1) or a salt thereof:

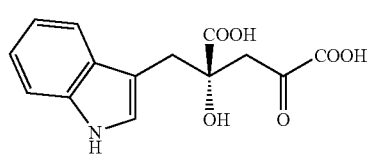

(1)

comprising:
reacting indole-3-pyruvic acid with pyruvic acid or oxaloacetic acid in the presence of a protein or a microorganism containing said protein to produce 4R-IHOG having an optical purity of at least 70%,
wherein said protein is selected from the group consisting of:
(a) a protein that is at least 85% sequence identical to the protein of SEQ ID NO: 15 and has 4R-aldolase activity and said protein has the core sequence of SEQ ID NO: 23, and
(b) a protein encoded by a polynucleotide that hybridizes with a polynucleotide consisting of a nucleotide sequence which is the full length complement of nucleotides 531 to 1385 of SEQ ID NO: 14 under stringent conditions, wherein said stringent conditions are 0.1× and 0.1 SDS at 65° C., wherein said protein has 4R-aldolase activity.

18. The method according to claim 17, wherein said protein is at least 85% sequence identical to the protein of SEQ ID NO: 15 and has 4R-aldolase activity and said protein has the core sequence of SEQ ID NO: 23.

19. The method according to claim 17, wherein said protein is encoded by a polynucleotide that hybridizes with a polynucleotide consisting of a nucleotide sequence which is the full length complement of nucleotides 531 to 1385 of SEQ ID NO: 14 under stringent conditions, wherein said stringent conditions are 0.1×SSC and 0.1 SDS at 65° C., wherein said protein has 4R-aldolase activity.

20. The method according to claim 17,
wherein said protein is obtained from a microorganism selected from bacteria belonging to the genus *Burkholderia*.

21. The method according to claim 20,
wherein the microorganism is *Burkholderia* sp. AJ110371 strain.

22. A method for producing 4R-monatin or a salt thereof comprising:
reacting indole-3-pyruvic acid with pyruvic acid or oxaloacetic acid in the presence of a protein or a microorganism containing said protein to preferentially produce 4R-IHOG, wherein said protein is selected from the group consisting of:
(a) a protein that is at least 85% sequence identical to the protein of SEQ ID NO: 15 and has 4R-aldolase activity and said protein has the core sequence of SEQ ID NO: 23, and
(b) a protein encoded by a polynucleotide that hybridizes with a polynucleotide consisting of a nucleotide sequence which is the full length complement of nucleotides 531 to 1385 of SEQ ID NO: 14 under stringent conditions, wherein said stringent conditions are 0.1× SSC and 0.1 SDS at 65° C., wherein said protein has 4R-aldolase activity; and converting a carbonyl group of 4R-IHOG of formula (2) or the salt thereof to an amino group to produce 4R-monatin or the salt thereof having an optical purity of 4R-monatin or the salt thereof of at least 90%,

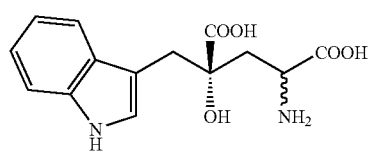

(2)

wherein a bond of a wavy line represents that both R- and S-configurations are included.

23. The method according to claim 22, wherein said protein is at least 85% sequence identical to the protein of SEQ ID NO: 15 and has 4R-aldolase activity and said protein has the core sequence of SEQ ID NO: 23.

24. The method according to claim 22, wherein said protein is encoded by a polynucleotide that hybridizes with a polynucleotide consisting of a nucleotide sequence which is the full length complement of nucleotides 531 to 1385 of SEQ ID NO: 14 under stringent conditions, wherein said stringent conditions are 0.1×SSC and 0.1 SDS at 65° C., wherein said protein has 4R-aldolase activity.

25. The method according to claim 22,
wherein said converting is by enzymatic amination of said carbonyl group to an amino group and wherein the enzyme for said enzymatic amination is an aminotransferase or a dehydrogenase.

26. The method according to claim 22, wherein said converting comprises,
reacting 4-(indole-3-ylmethyl)-4-hydroxy-2-oxoglutaric acid with an amine compound of formula (3) or a salt thereof:

wherein R represents a hydrogen atom, an alkyl, aryl or aralkyl group,
under neutral or alkali conditions to produce 4-hydroxy-4-(3-indolylmethyl)-2-hydroxyiminoglutaric acid (IHOG-oxime) of formula (4) or the salt thereof:

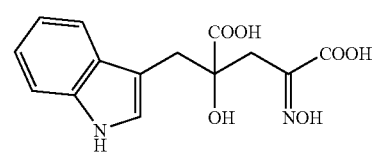

(4)

crystallizing a 4R-isomer of the produced IHOG-oxime or the salt thereof;
reducing the crystallized 4R-isomer to produce 4R-monatin or the salt thereof with an optical purity of at least 90%.

27. The method according to claim 26,
wherein the amine compound of formula (3) is at least one amine compound selected from the group consisting of hydroxylamine, methoxyamine and benzyloxyamine.

28. The method according to claim 26,
wherein the 4R-isomer of IHOG-oxime or the salt thereof is reduced in the presence of hydrogen and a hydrogenated catalyst.

29. The method according to claim 26,
wherein (2R,4R)-monatin is recovered by said crystallizing.

30. The method according to claim 26,
wherein said crystallizing is performed with a crystallization solvent selected from the group consisting of water, an alcohol solvent and an aqueous alcohol solvent.

31. The method according to claim 22,
wherein said protein used in the method is obtained from a microorganism selected from bacteria belonging to the genus *Burkholderia*.

32. The method according to claim 31,
wherein the microorganism is *Burkholderia* sp. AJ110371 strain.

* * * * *